(12) United States Patent
Fu et al.

(10) Patent No.: US 12,391,642 B2
(45) Date of Patent: *Aug. 19, 2025

(54) TETRAHYDRO-1H-CYCLOPENTA[CD]INDENE DERIVATIVES AS HYPOXIA INDUCIBLE FACTOR-2(ALPHA) INHIBITORS

(71) Applicant: NIKANG THERAPEUTICS, INC., Wilmington, DE (US)

(72) Inventors: Jiping Fu, Danville, CA (US); Yan Lou, Dallas, TX (US); Yigang He, Newark, DE (US)

(73) Assignee: NiKang Therapeutics, Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/351,283

(22) Filed: Jul. 12, 2023

(65) Prior Publication Data
US 2023/0373909 A1 Nov. 23, 2023

Related U.S. Application Data

(63) Continuation of application No. 17/670,423, filed on Feb. 11, 2022, now Pat. No. 11,753,366, which is a continuation of application No. 17/218,129, filed on Mar. 30, 2021, now Pat. No. 11,267,782, which is a continuation of application No. 16/851,018, filed on Apr. 16, 2020, now abandoned.

(60) Provisional application No. 62/946,191, filed on Dec. 10, 2019, provisional application No. 62/836,019, filed on Apr. 18, 2019.

(51) Int. Cl.
C07C 255/54 (2006.01)
A61K 31/277 (2006.01)
A61K 31/4412 (2006.01)
A61K 45/06 (2006.01)
A61P 1/16 (2006.01)
A61P 9/12 (2006.01)
A61P 11/00 (2006.01)
A61P 35/00 (2006.01)
C07C 49/747 (2006.01)
C07C 225/20 (2006.01)
C07C 255/50 (2006.01)
C07C 311/07 (2006.01)
C07C 313/06 (2006.01)
C07D 213/63 (2006.01)
C07D 213/65 (2006.01)
C07D 233/60 (2006.01)

(52) U.S. Cl.
CPC ............ C07C 255/54 (2013.01); A61P 35/00 (2018.01); C07C 313/06 (2013.01); C07D 213/63 (2013.01); C07D 233/60 (2013.01); A61K 45/06 (2013.01); C07C 2603/10 (2017.05); C07C 2603/97 (2017.05)

(58) Field of Classification Search
CPC ... C07C 255/54; C07C 255/50; C07C 313/06; C07C 2603/10; C07C 2603/97; C07C 2603/40; C07C 49/747; C07C 211/42; C07C 225/20; C07C 311/07; A61K 45/06; A61K 31/277; A61K 31/4412; A61P 35/00; A61P 29/00; A61P 1/16; A61P 11/00; A61P 9/12; C07D 213/63; C07D 213/65; C07D 233/60; C07B 2200/05; C07B 2200/07; C07B 2200/13
See application file for complete search history.

(56) References Cited

U.S. PATENT DOCUMENTS

| 6,133,279 | A | 10/2000 | Cynshi et al. |
|---|---|---|---|
| 9,908,845 | B2 | 3/2018 | Dixon et al. |
| 10,098,878 | B2 | 10/2018 | Bruick et al. |
| 10,155,726 | B2 | 12/2018 | Wehn et al. |
| 10,278,942 | B2 | 5/2019 | Josey et al. |
| 11,267,782 | B2 | 3/2022 | Fu et al. |
| 11,420,936 | B2 | 8/2022 | Fu et al. |
| 11,634,382 | B2 | 4/2023 | Fu et al. |
| 11,753,366 | B2 | 9/2023 | Fu et al. |
| 2012/0316204 | A1 | 12/2012 | Shalwitz et al. |
| 2016/0362390 | A1 | 12/2016 | Wehn et al. |
| 2019/0048421 | A1 | 2/2019 | Kim et al. |
| 2019/0282535 | A1 | 9/2019 | Josey et al. |
| 2020/0361855 | A1 | 11/2020 | Fu et al. |
| 2021/0347729 | A1* | 11/2021 | Fu .................. C07C 313/06 |
| 2021/0380536 | A1 | 12/2021 | Fu et al. |

(Continued)

FOREIGN PATENT DOCUMENTS

WO WO 2005/118580 A2 12/2005
WO WO 2006/094292 A2 9/2006
(Continued)

OTHER PUBLICATIONS

International Search Report and Written Opinion for PCT/US2020/028579 mailed Aug. 3, 2020, 10 pages.
(Continued)

Primary Examiner — Sun Jae Yoo
(74) Attorney, Agent, or Firm — Squire Patton Boggs (US) LLP

(57) ABSTRACT

The present disclosure provides certain tetrahydro-1H-cyclopenta[cd]indene compounds that are Hypoxia Inducible Factor 2α (HIF-2α) inhibitors and are therefore useful for the treatment of diseases treatable by inhibition of HIF-2α. Also provided are pharmaceutical compositions containing such compounds and processes for preparing such compounds.

19 Claims, No Drawings

(56) References Cited

U.S. PATENT DOCUMENTS

| | | |
|---|---|---|
| 2022/0054451 A1 | 2/2022 | Fu et al. |
| 2022/0274914 A1 | 9/2022 | Fu et al. |
| 2022/0380302 A1* | 12/2022 | Fu .................... A61P 35/00 |
| 2023/0115881 A1 | 4/2023 | Cook et al. |
| 2023/0202970 A1 | 6/2023 | Fu et al. |

FOREIGN PATENT DOCUMENTS

| | | |
|---|---|---|
| WO | WO 2013/013609 A1 | 1/2013 |
| WO | WO 2015/035223 A1 | 3/2015 |
| WO | WO 2015/095048 A1 | 6/2015 |
| WO | WO 2016/144825 A1 | 9/2016 |
| WO | WO 2018/031680 A1 | 2/2018 |
| WO | WO 2019/052133 A1 | 3/2019 |
| WO | WO 2019/191227 A1 | 10/2019 |
| WO | WO 2020/055883 A1 | 3/2020 |
| WO | WO 2020/081695 A1 | 4/2020 |
| WO | WO 2020/214853 A1 | 10/2020 |
| WO | WO 2021/016280 A1 | 1/2021 |
| WO | WO/2021/212062 A1 | 10/2021 |
| WO | WO 2022/086822 A1 | 4/2022 |
| WO | WO 2023/064305 A1 | 4/2023 |
| WO | WO 2023/069372 A1 | 4/2023 |

OTHER PUBLICATIONS

U.S. Appl. No. 17/503,176, filed Oct. 15, 2021.
Claims of U.S. Appl. No. 17/686,385, filed Mar. 3, 2022.
Renal-Cancer-Cure, 2021, https://www.cancer.gov/types/kidney/hp/kidney-treatment-pdg#::text=Renal%20cell%20cancer%2C%20also%20called,or%20degree%20of%20tunnor%20dissennination.
Renal-Cancer-Prevention, 2021, https://www.cancer.org/cancer/kidney-cancer/causes-risksprevention/prevention.htnnl.
Renal-Carcinoma, 2021, https://ascopost.conn/news/february-2020/oral-hif2a-inhibitor-for-advanced-clear-cell-renal-cell-carcinonna/.
Wehn et al., "Design and Activity of Specific Hypoxia-Inducible Factor 2# (HIF-2#) Inhibitors for the Treatment of Clear Cell Renal Cell Carcinoma: Discovery of Clinical Candidate (S)-3-((2,2-difluoro-1-hydroxy-7-(methylsulfonyl)-2,3-dihydro-1H-inden-4-yl)oxy)-5-fluorobenzonitrile (PT2385)", J. Med. Chem., DOI: 10.1021/acs.jmedchem.8b01196 Publication Date (Web): Oct. 5, 2018.
Xu et al., "3-[(1S,2S,3R)-2,3-Difluoro-1-hydroxy-7-methylsulfonyl-indan-4-yl]oxy-5-fluoro-benzonitrile (PT2977), a Hypoxia-Inducible Factor 2# (HIF-2#) Inhibitor for the Treatment of Clear Cell Renal Cell Carcinoma", J. Med. Chem., DOI: 10.1021/acs.jmedchem.9b00719, Publication Date (Web): Jun. 24, 2019.
Byrn S; The 17th Revision of the Japanese Pharmacopoeia, Mar. 7, 2016, pp. 71-74; Pharmaceutical Solids: A Strategic Approach to Regulatory Considerations, Pharmaceutical Research, United States, Kluwer Academic Publishers, Jul. 1, 1995, vol. 12, No. 7, pp. 945-954.

* cited by examiner

TETRAHYDRO-1H-CYCLOPENTA[CD]INDENE DERIVATIVES AS HYPOXIA INDUCIBLE FACTOR-2(ALPHA) INHIBITORS

CROSS REFERENCE TO RELATED APPLICATIONS

This application is a Continuation of U.S. patent application Ser. No. 17/670,423 filed Feb. 11, 2022, which is a Continuation of U.S. patent application Ser. No. 17/218,129 filed Mar. 30, 2021, which is a Continuation of U.S. patent application Ser. No. 16/851,018 filed Apr. 16, 2020, which claims the benefit of U.S. Provisional Application No. 62/836,019 filed Apr. 18, 2019, and U.S. Provisional Application No. 62/946,191 filed Dec. 10, 2019; the entireties of which are herein incorporated by reference.

FIELD OF THE DISCLOSURE

The present disclosure provides certain tetrahydro-1H-cyclopenta[cd]indene compounds that are Hypoxia Inducible Factor 2α (HIF-2α) inhibitors and are therefore useful for the treatment of diseases treatable by inhibition of HIF-2α. Also provided are pharmaceutical compositions containing such compounds and processes for preparing such compounds.

BACKGROUND

Hypoxia is as an important regulator of both physiological and pathological processes, including various types of cancer, liver disease such as nonalcoholic steatohepatitis (NASH), inflammatory disease such as inflammatory bowel disease (IBD), pulmonary diseases such as pulmonary arterial hypertension (PAH), and iron load disorders.

Hypoxia is well-known to drive cancer progression and is associated with poor patient prognosis, resistance to chemotherapy and radiation treatment. With the progress over the past several decades in elucidating molecular mechanisms that enable cellular adaptation to chronic oxygen deprivation, there is a strong interest in developing drugs that can effectively block the hypoxic response pathway in tumors. Among signaling modules, involved in the hypoxic response, that have been explored as therapeutic targets for treating cancer, HIF-α proteins continue to draw interest as they offer the possibility to broadly inhibit downstream hypoxia effects within both tumor and tumor microenvironment. Thus, directly targeting HIF-α proteins offers an exciting opportunity to attack tumors on multiple fronts (see Keith, et al. Nature Rev. Cancer 12:9-22, 2012).

Hypoxia-Inducible Factors (HIF-1α and HIF-2α) are key transcription factors in the hypoxia pathway, therefore serve as attractive targets for therapeutic intervention. The half-life of HIF-α proteins is tightly regulated by the oxidative status within the cell. Under normoxic conditions, HIF-specific prolyl-hydroxylases (PHD) hydroxylates specific proline residues on the HIF proteins, which is then recognized by the tumor suppressor von Rippel-Lindau (VHL). The binding of VHL further recruits E3 ubiquition-ligase complex that targets HIF-α proteins for proteasome mediated degradation. Under hypoxic conditions, when PHDs are inhibited as they require oxygen to be functional, HIF-α proteins accumulate and enter the nucleus to actively drive gene expression. In addition, genetic mutations of the VHL gene which result in loss of VHL function lead to constitutively active HIF-α proteins independent of oxygen levels. Upon activation, these transcription factors stimulate the expression of genes that collectively regulate anaerobic metabolism, angiogenesis, cell proliferation, cell survival, extracellular matrix remodeling, pH homeostasis, amino acid and nucleotide metabolism, and genomic instability.

Both HIF-1α and HIF-2α dimerize with HIF-1β (also named as ARNT: aryl hydrocarbon receptor nuclear translocator) and the dimer subsequently binds to hypoxia response elements (HRE) on target genes. The expression of HIF-1β is independent of oxygen levels or VHL status, thus, transcriptional activity of the complex is primarily controlled by the availability of the HIF-α proteins. HIF-1α and HIF-2α differ in their tissue distribution, sensitivity to hypoxia, timing of activation and target gene specificity (Hu, et al. Mol. Cell Biol. 23:9361-9374, 2003 and Keith, et al. Nature Rev. Cancer 12:9-22, 2012). Whereas HIF-1α mRNA is ubiquitously expressed, the expression of HIF-2α mRNA is found predominantly in kidney fibroblasts, hepatocytes and intestinal lumen epithelial cells. Neither HIF-α is detected in normal tissue with the exception of HIF-2α, which is expressed in macrophages (see Talks, et al. Am. J. Pathol. 157:411-421, 2000). In response to hypoxia, HIF-1α exhibits a transient, acute transcriptional response. In contrast, HIF-2α presents a more prolonged transcriptional effect. Furthermore, HIF-2α has greater transcriptional activity than HIF-1 α under moderately hypoxic conditions like those encountered in end capillaries (see Holmquist-Menge/bier, et al. Cancer Cell 10:413-423, 2006). Although some hypoxia-regulated genes are regulated by both HIF-1α and HIF-2α, certain genes are only responsive to a specific HIF-α protein. For example, lactate dehydrogenase A (LDHA), phosphoglycerate kinase (PGK) and pyruvate dehydrogenase kinase 1 (PDK1) are mostly controlled by HIF-1α, while Oct-4 and erythropoietin (EPO) are exclusively regulated by HIF-2α.

In general, the relative contributions of HIF-α proteins on gene transcription are both cell type specific, and disease specific. In fact, there are reports supporting the HIF-α proteins playing conflicting roles in tumorigenesis. One example is the regulation of HIF-α on MYC, which is an important transcription factor and frequently overexpressed in human cancers. It has been shown that HIF-2α activation increases MYC transcription activity, while HIF-1α inhibits MYC activity. As a result, in MYC driven tumors, HIF-2α inhibition decreased proliferation whereas HIF-la inhibition increased growth (see Gordan, et al. Cancer Cell 11:335-347, 2007 and Koshiji et al. EMBO J. 23:1949-1956, 2004). Therefore, identification of small molecules that specifically inhibit HIF-2α activity is desirable. In addition, HIF-2α is demonstrated to be a key driver of Clear Cell Renal Cell Carcinoma (ccRCC) with VHL deficiency and several other pseudohypoxic tumors including but not limited to glioblastoma, neuroblastoma, somatostatinomas, leiomyomas/leiomyosarcomas, polycythaemia and retinal abnormalities etc. Thus, an HIF-2α inhibitor will offer therapeutic benefits with limited toxicity than a pan-HIF-α inhibitor.

In addition to a direct role in regulating growth-promoting genes in tumor cells (e.g. ccRCC), HIF-2α also mediates the immunosuppressive effect of hypoxia on the tumor microenvironment. Expression of HIF-2α has been detected in cells of the myeloid lineage, and accumulation of HIF-2α protein has been readily detected in various human cancers (see Talks K L, et al. Am J Pathol. 2000; 157(2):411-421). Overexpression of HIF-2α in tumor-associated macrophages (TAMs) is associated with high-grade human tumors and is correlated with poor prognosis. Mechanistically, HIF-2α promotes the polarization of macrophages to the immunosuppressive M2 phenotype and enhances migration and invasion of tumor-associated macrophages (see Imtiyaz H Z et al. J Clin Invest. 2010; 120(8):2699-2714). Furthermore, HIF-2α can indirectly promote additional immunosuppressive pathways (e.g. adenosine and arginase etc.) by modulating the expression of key signaling regulators such as adenosine A2B/A2A receptors and arginase. These data suggest that HIF-2α may be a potential therapeutic target for treating a broader range of inflammatory disorders and cancer as a single agent or in combination with other therapeutic agents e.g., immunotherapies.

Because of the roles of HIF-α proteins in regulating physiological response to the change of oxygen levels, they have been causally associated with many hypoxia-related pathological processes in addition to cancer. Inflammatory bowel disease (IBD) is a chronic relapsing inflammatory disease of the intestine. Normally, the intestines maintain a dynamic and rapid fluctuation in cellular oxygen tension, with the tips of the epithelial villi being hypoxic and the base of the epithelial villi better oxygenated. A dysregulated epithelial oxygen tension plays a role in intestinal inflammation and resolution in IBD (see Shah Y. M., Molecular and Cellular Pediatrics, 2016 December; 3 (1): 1). Even though HIF-1α and HIF-2α can bind to the same canonical HREs, multiple studies have demonstrated that HIF-1α and HIF-2α regulate distinct subset of genes, leading to contrasting effect in symptoms of IBD. HIF-1α in intestinal epithelial cells is widely recognized as a major protective factor in IBD (see Karhausen J, et al. J Clin Invest. 2004; 114(8):1098-1106; Furuta G T, et al. J Exp Med. 2001; 193(9):1027-1034). However, HIF-2α activation contributes to IBD through multiple mechanisms, including directly regulating a number of pro-inflammatory cytokines such as tumor necrosis factor-α to drive inflammation, and indirectly disrupting intestine barrier integrity through increasing the turnover of tight junction protein occluding (see Xue X, et al. Gastroenterology. 2013; 145 (4): 831-841; Glover L E, et al. Proc Natl Acad Sci USA. 2013; 110(49):19820-19825). Therefore, in IBD, a HIF-2α inhibitor holds promise of suppressing chronic activation of HIF-2α to revert the pro-inflammatory response and increase the intestinal barrier integrity.

With the growing epidemic of obesity and metabolic syndrome, NASH is becoming a common chronic liver disease and limited therapeutic options are available. A recent study has demonstrated a positive correlation between intestinal HIF-2α signaling with body-mass index and hepatic toxicity, with further animal model study supporting the causality of this correlation (see Xie C, et al. Nat Med. 2017 November; 23(11):1298-1308.). Thus, targeting intestinal HIF-2α represents a novel therapeutic strategy for NASH.

PAH is a life-threatening disease with very poor prognosis. Progressive pulmonary vascular remodeling, characterized by concentric pulmonary arterial wall thickening and obliterative intimal lesions, is one of the major causes for the elevation of pulmonary vascular resistance (PVR) and pulmonary arterial pressure (PAP) in patients with PAH (see Aggarwal S, et al. Compr Physiol. 2013 July; 3(3):1011-34). Recently, HIF-2α is found to contribute to the process of hypoxic pulmonary vascular remodeling, reduced plasticity of the vascular bed, and ultimately, debilitating PAH (see Andrew S., et al. Proc Natl Acad Sci USA. 2016 Aug. 2; 113(31):8801-8806, Tang H, et al. Am J Physiol Lung Cell Mol Physiol. 2018 Feb. 1; 314(2):L256-L275.). These studies have offered new insight into the role of pulmonary endothelial HIF-2α in regulating the pulmonary vascular response to hypoxia, and offer a much-needed intervention therapeutics strategy by targeting HIF-2.

Iron is an essential nutrient that is required for oxygen delivery and serves as a cofactor in many key enzymatic and redox reactions. HIF-2α regulates the expression of key genes that contribute to iron absorption, which, when disrupted, leads to iron load disorders. For example, an elegant study with mice lacking HIF-2α in the intestinal epithelium showed HIF-2α knockout results in a significant decrease in the duodenal levels of Dmt1, Dcytb and FPN mRNAs, all important genes in iron transport and absorption. More importantly, these effects were not compensated by HIF-1α (see Mastrogiannaki M, et al. J Clin Invest. 2009; 119(5): 1159-1166). Thus, a small molecule that targets HIF-2 α holds potential of improving iron homeostasis in patients with iron disorders. Therefore, identification of small molecules that inhibit HIF-2α activity is desirable. The present disclosure fulfills this and related needs.

SUMMARY

In a first aspect, provided is a compound of Formula (IA):

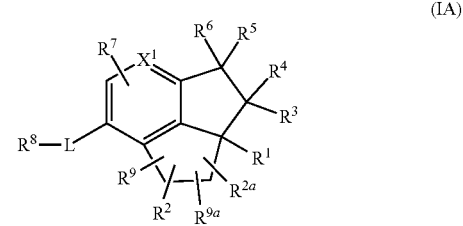

(IA)

wherein:
X$^1$ is CH or N;
R$^1$ is hydroxy, halo, amino, —OP(O)(OH)$_2$, —OCH$_2$OP(O)(OH)$_2$, —OCOR$^{10}$, —OCOOR$^{11}$, —OCONR$^{12}$R$^{13}$, —OCHR$^{14}$OCOR$^{15}$ or —OCHR$^{14}$OCOOR$^{15a}$ where R$^{10}$, R$^{11}$, and R$^{15}$ and R$^{15a}$ are independently alkyl or alkyl substituted with amino, carboxy or hydroxy, R$^{12}$ and R$^{13}$ are independently hydrogen, alkyl, or alkyl substituted with amino, carboxy or hydroxy or R$^{12}$ and R$^{13}$ together with the nitrogen atom to which they are attached form optionally substituted heterocyclyl, and each R$^{14}$ is hydrogen, alkyl, or haloalkyl;
R$^2$ is hydrogen, deuterium, alkyl, halo, haloalkyl, alkenyl, or alkynyl;
R$^{2a}$ is hydrogen, halo, or deuterium;
R$^3$ and R$^4$ are independently hydrogen, deuterium, alkyl, cycloalkyl, halo, haloalkyl, hydroxyalkyl, or alkoxyalkyl; or
R$^3$ and R$^4$ together with the carbon to which they are attached form >C(=O), 3 to 6 membered cycloalkylene, or 4 to 6 membered optionally substituted heterocyclylene;
R$^5$ is hydrogen, deuterium, alkyl, halo, haloalkyl, hydroxy, or alkoxy;
R$^6$ is hydrogen, deuterium, alkyl, cycloalkyl, or halo; or
R$^5$ and R$^6$ together with the carbon to which they are attached form >C(=O), alkyldienyl, 3 to 6 membered cycloalkylene, or 4 to 6 membered optionally substituted heterocyclylene; provided R$^5$ and R$^6$ and R$^3$ and R$^4$ together with the carbon to which they are attached do not form >C(=O), cycloalkylene or optionally substituted 4 to 6 membered heterocyclylene simultaneously;

$R^7$ is hydrogen, deuterium, alkyl, alkoxy, cyano, halo, haloalkyl, or haloalkoxy;

L is a bond, S, SO, $SO_2$, O, CO, or $NR^{16}$ where $R^{16}$ is hydrogen or alkyl;

$R^8$ is alkyl, haloalkyl, hydroxyalkyl, alkoxyalkyl, aminoalkyl, cycloalkyl, cycloalkenyl, bicyclic cycloalkyl, oxocycloalkenyl, cycloalkylalkyl, aryl, aralkyl, heterocyclyl, spirocycloalkyl, spiroheterocyclyl, heterocyclylalkyl, heteroaryl, or heteroaralkyl wherein aryl or heteroaryl, each by itself or as part of aralkyl or heteroaralkyl, or heterocyclyl by itself or as part of heterocyclylalkyl is substituted with $R^a$, $R^b$, $R^c$, $R^g$ and $R^h$ wherein $R^a$, $R^b$, and Re are independently selected from hydrogen, deuterium, alkyl, haloalkyl, haloalkyloxy, alkoxy, hydroxy, halo, cyano, hydroxyalkyl, alkoxyalkyl, aminoalkyl, alkenyl, alkynyl, alkylidenyl, optionally substituted aryl, optionally substituted heteroaryl, and optionally substituted heterocyclyl and $R^g$ and $R^h$ are independently selected from hydrogen, deuterium, and halo; and $R^9$ is hydrogen, alkyl, cycloalkyl, hydroxy, alkoxy, cyano, halo, haloalkyl, haloalkoxy, alkylsulfoxide, alkylsulfonyl, or heteroaryl wherein the heteroaryl is optionally substituted with $R^d$, $R^e$, and $R^f$ independently selected from hydrogen, alkyl, haloalkyl, alkoxy, hydroxy, halo, and cyano; or when $R^9$ and $R^2$ are attached to the same carbon atom, $R^9$ and $R^2$ can combine to form oxo, alkyldienyl, 3 to 6 membered cycloalkylene, or 4 to 6-membered heterocyclylene;

$R^{9a}$ is hydrogen, halo, or deuterium;

a pharmaceutically acceptable salt thereof.

In a first embodiment of the first aspect, provided is a compound of Formula (I):

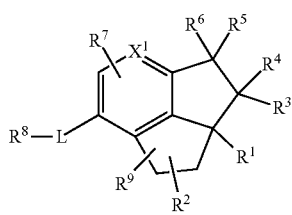

(I)

wherein:

$X^1$ is CH or N;

$R^1$ is hydroxy, halo, amino, —OP(O)(OH)$_2$, —OCH$_2$OP(O)(OH)$_2$, —OCOR$^{10}$, —OCOOR$^{11}$, —OCONR$^{12}$R$^{13}$, —OCHR$^{14}$OCOR$^{15}$ or —OCHR$^{14}$OCOOR$^{15a}$ where $R^{10}$, $R^{11}$, and $R^{15}$ and $R^{15a}$ are independently alkyl or alkyl substituted with amino, carboxy or hydroxy, $R^{12}$ and $R^{13}$ are independently hydrogen, alkyl, or alkyl substituted with amino, carboxy or hydroxy or $R^{12}$ and $R^{13}$ together with the nitrogen atom to which they are attached form optionally substituted heterocyclyl, and each $R^{14}$ is hydrogen, alkyl, or haloalkyl;

$R^2$ is hydrogen, deuterium, alkyl, halo, haloalkyl, alkenyl, or alkynyl;

$R^3$ and $R^4$ are independently hydrogen, deuterium, alkyl, cycloalkyl, halo, haloalkyl, hydroxyalkyl, or alkoxyalkyl; or $R^3$ and $R^4$ together with the carbon to which they are attached form >C(=O), 3 to 6 membered cycloalkylene, or 4 to 6 membered optionally substituted heterocyclylene;

$R^5$ is hydrogen, deuterium, alkyl, halo, haloalkyl, hydroxy, or alkoxy;

$R^6$ is hydrogen, deuterium, alkyl, cycloalkyl, or halo; or $R^5$ and $R^6$ together with the carbon to which they are attached form 3 to 6 membered cycloalkylene or 4 to 6 membered optionally substituted heterocyclylene; provided $R^5$ and $R^6$ and $R^3$ and $R^4$ together with the carbon to which they are attached do not form cycloalkylene or optionally substituted 4 to 6 membered heterocyclylene simultaneously;

$R^7$ is hydrogen, deuterium, alkyl, alkoxy, cyano, halo, haloalkyl, or haloalkoxy;

L is a bond, S, SO, $SO_2$, O, CO, or $NR^{16}$ where $R^{16}$ is hydrogen or alkyl;

$R^8$ is alkyl, haloalkyl, hydroxyalkyl, alkoxyalkyl, aminoalkyl, cycloalkyl, cycloalkenyl, bicyclic cycloalkyl, oxocycloalkenyl, cycloalkylalkyl, aryl, aralkyl, heterocyclyl, spirocycloalkyl, spiroheterocyclyl, heterocyclylalkyl, heteroaryl, or heteroaralkyl wherein aryl or heteroaryl, each by itself or as part of aralkyl or heteroaralkyl, or heterocyclyl by itself or as part of heterocyclylalkyl is substituted with $R^a$, $R^b$, and $R^c$ independently selected from hydrogen, alkyl, haloalkyl, haloalkyloxy, alkoxy, hydroxy, halo, cyano, hydroxyalkyl, alkoxyalkyl, aminoalkyl, alkenyl, alkynyl, alkylidenyl, optionally substituted aryl, optionally substituted heteroaryl, and optionally substituted heterocyclyl; and $R^9$ is hydrogen, alkyl, cycloalkyl, hydroxy, alkoxy, cyano, halo, haloalkyl, haloalkoxy, alkylsulfoxide, alkylsulfonyl, or heteroaryl wherein the heteroaryl is optionally substituted with $R^d$, $R^e$, and $R^f$ independently selected from hydrogen, alkyl, haloalkyl, haloalkoxy, alkoxy, hydroxy, halo, and cyano; or when $R^9$ and $R^2$ are attached to the same carbon atom, $R^9$ and $R^2$ can combine to form oxo, alkyldienyl, 3 to 6 membered cycloalkylene, or 4 to 6-membered heterocyclylene;

a pharmaceutically acceptable salt thereof.

In a second aspect, this disclosure is directed to a method of treating a disease treatable by inhibition of HIF2α in a patient, preferably the patient is in need of such treatment, which method comprises administering to the patient, preferably a patient in need of such treatment, a therapeutically effective amount of a compound of Formula (IA) or (I) (or any of the embodiments thereof described herein) or a pharmaceutically acceptable salt thereof.

In one embodiment of the second aspect, the disease is cancer such as renal cancer, glioblastoma (see PNAS 2017, 114, E6137-E6146), renal cell carcinoma, neuroblastoma, pheochromocytomas and paragangliomas (see European Journal of Cancer 2017, 86, 1-4), somatostatinomas, hemangioblastomas, gastrointestinal stromal tumors (GIST), pituitary tumors, leiomyomas, leiomyosarcomas, polycythaemia or retinal tumors. In another embodiment, non-cancer diseases that could benefit from Hif-2α inhibition include VHL (von Hippel-Lindau) disease (see Oncotarget, 2015, 6, 23036-23037), PAH (pulmonary artery hypertension) (see Mol. Cell. Biol. 2016, 36, 1584-1594), reflux esophagitis (see Current Opinion in Pharmacology 2017, 37:93-99), hepatic steatosis (see Nature Medicine 2017, 23, 1298-1308), NASH, inflammatory disease such as inflammatory bowel disease (see Nature Reviews gastroenterology &

Hepatology 2017, 14, 596), autoimmune disease such as Graft-versus-Host-Disease (see Blood, 2015, 126, 1865), or iron overload.

In a third aspect, the disclosure is directed to a pharmaceutical composition comprising a compound of Formula (IA) or (I) (or any of the embodiments thereof described herein) or a pharmaceutically acceptable salt thereof; and a pharmaceutically acceptable excipient.

In a fourth aspect, the disclosure is directed to a compound of Formula (IA) or (I), (or any embodiments thereof described herein) or a pharmaceutically acceptable salt thereof for use as a medicament. In one embodiment, the compound Formula (I) (and any embodiments thereof described herein) or a pharmaceutically acceptable salt, is useful for the treatment of one or more of diseases disclosed in the second aspect above.

In a fifth aspect provided is the use of a compound of Formula (IA) or (I) or a pharmaceutically acceptable salt thereof (and any embodiments thereof disclosed herein) in the manufacture of a medicament for treating a disease in a patient in which the activity of HIF2α contributes to the pathology and/or symptoms of the disease. In one embodiment the disease is one or more of diseases disclosed in the second aspect above.

In a sixth aspect provided is a method of inhibiting HIF2α which method comprises contacting HIF2× with a compound of Formula (IA) or (I) (or any of the embodiments thereof described herein) or a pharmaceutically acceptable salt thereof; or contacting HIF2α with a pharmaceutical composition comprising a compound of Formula (IA) or (I) (or any of the embodiments thereof described herein) or a pharmaceutically acceptable salt thereof; and a pharmaceutically acceptable excipient.

In any of the aforementioned aspects involving the treatment of cancer, are further embodiments comprising administering the compound of Formula (IA) or (I) or a pharmaceutically acceptable salt thereof (or any embodiments thereof disclosed herein) in combination with at least one additional anticancer agent such as an EGFR inhibitor gefitinib, erlotinib, afatinib, icotinib, neratinib, rociletinib, cetuximab, panitumumab, zalutumumab, nimotuzumab, or matuzumab. In another embodiment, the compound of Formula (IA) or (I) (and any embodiments thereof described herein) or a pharmaceutically acceptable salt thereof is administered in combination with a HER2/neu inhibitor including lapatinib, trastuzumab, and pertuzumab. In another embodiment, the compound of Formula (IA) or (I) (and any embodiments thereof described herein) or a pharmaceutically acceptable salt thereof is administered in combination with a PI3k/mTOR inhibitor including idelalisib, buparlisib, BYL719, and LY3023414. In another embodiment, the compound of Formula (IA) or (I) (and any embodiments thereof described herein) or a pharmaceutically acceptable salt thereof is administered in combination with a VEGF inhibitor such as bevacizumab, and/or a multi-tyrosine kinase inhibitors such as sorafenib, sunitinib, pazopanib, and cabozantinib. In another embodiment, the compound of Formula (IA) or (I) (and any embodiments thereof described herein) or a pharmaceutically acceptable salt thereof is administered in combination with a an immunotherapeutic agents such as PD-1 and PD-L1 inhibitors, CTLA4 inhibitors, IDO inhibitors, TDO inhibitors, A2A agonists, A2B agonists, STING agonists, RIG-1 agonists, Tyro/Axl/Mer inhibitors, glutaminase inhibitors, arginase inhibitors, CD73 inhibitors, CD39 inhibitors, TGF-β inhibitors, IL-2, interferon, PI3K-γ inhibitors, CSF-1R inhibitors, GITR agonists, OX40 agonists, TIM-3 antagonists, LAG-3 antagonists, CAR-T therapies, and therapeutic vaccines. When combination therapy is used, the agents can be administered simultaneously or sequentially.

In an seventh aspect, provided is a process of making a compound of Formula (IA) where $R^9$ is hydroxy and $X^1$, $R^2$ is hydrogen, $R^1$, $R^3$ to $R^8$, L, $R^{2a}$ and $R^{9a}$ are as defined in the first aspect above, i.e. Formula (IA-1):

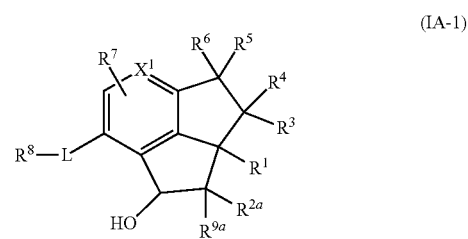

(IA-1)

comprising treating a compound of Formula (IA) where $R^2$ and $R^9$ together with the carbon atom to which they are attached form >C(=O) and $X^1$, $R^1$, $R^3$ to $R^8$, L, $R^{2a}$ and $R^{9a}$ are as defined in the first aspect above, i.e. Formula (IA-2):

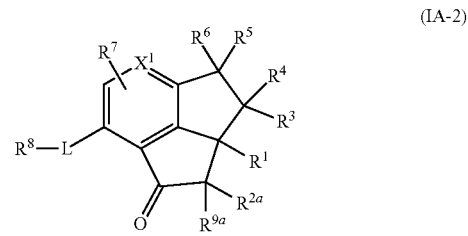

(IA-2)

with a suitable reducing agent.

In a first embodiment of the seventh aspect, in each of the compounds of Formula (IA-1) and (IA-2), $X^1$ is CH, $R^1$ is hydroxy, $R^3$, $R^4$, $R^5$, and $R^6$ are fluoro, and $R^7$, $R^{2a}$ and $R^{9a}$ are hydrogen, L is O, and $R^8$ is 3-cyano-5-fluorophenyl.

In a ninth aspect, provided is a process of making a compound of Formula (IA) where $R^2$ is hydrogen, $R^9$ is fluoro and $X^1$, $R^1$, $R^3$ to $R^8$, L, $R^{2a}$ and $R^{9a}$ are as defined in the first aspect above, i.e. Formula (IA-3):

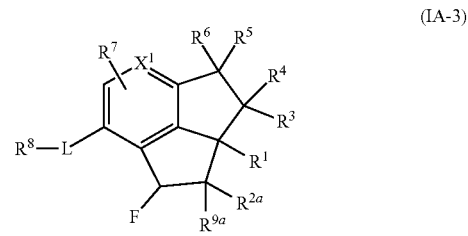

(IA-3)

comprising treating a compound of Formula (I) where $R^2$ hydrogen and $R^9$ is hydroxy, and $X^1$, $R^1$, $R^3$ to $R^8$, L, $R^{2a}$ and $R^{9a}$ are as defined in the first aspect above i.e. Formula (IA-1):

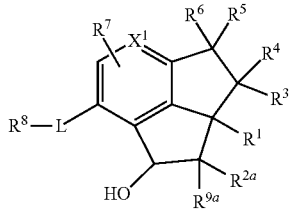

(IA-1)

with a suitable fluorinating agent.

In a first embodiment of the ninth aspect, in each of the compounds of Formula (IA-3) and (IA-1), $X^1$ is CH, $R^1$ is hydroxy, $R^3$, $R^4$, $R^5$, and $R^6$ are fluoro, and $R^7$, $R^{2a}$ and $R^{9a}$ are hydrogen, L is O, and $R^8$ is 3-cyano-5-fluorophenyl.

DETAILED DESCRIPTION

Definitions

Unless otherwise stated, the following terms used in the specification and claims are defined for the purposes of this Application and have the following meaning:

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, butyl, pentyl, and the like. It will be recognized by a person skilled in the art that the term "alkyl" may include "alkylene" groups.

"Alkylene" means a linear saturated divalent hydrocarbon radical of one to six carbon atoms or a branched saturated divalent hydrocarbon radical of three to six carbon atoms unless otherwise stated e.g., methylene, ethylene, propylene, 1-methylpropylene, 2-methylpropylene, butylene, pentylene, and the like.

"Alkenyl" means a linear monovalent hydrocarbon radical of two to six carbon atoms or a branched monovalent hydrocarbon radical of three to six carbon atoms containing a double bond, e.g., propenyl, butenyl, and the like.

"Alkyldienyl" is alkenyl as defined above that is attached via the terminal divalent carbon. For example, in the compound below:

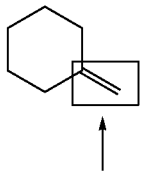

the alkyldienyl group is enclosed by the box which is indicated by the arrow.

"Haloalkyldienyl" is alkyldienyl that is substituted with one or two halo, each group as defined herein.

"Alkynyl" means a linear monovalent hydrocarbon radical of two to six carbon atoms or a branched monovalent hydrocarbon radical of three to six carbon atoms containing a triple bond, e.g., propynyl, butynyl, and the like.

"Alkylthio" means a —SR radical where R is alkyl as defined above, e.g., methylthio, ethylthio, and the like.

"Alkylsulfonyl" means a —SO$_2$R radical where R is alkyl as defined above, e.g., methylsulfonyl, ethylsulfonyl, and the like.

"Alkylsulfoxide" means a —SOR radical where R is alkyl as defined above, e.g., methylsulfoxide, ethylsulfoxide, and the like.

"Amino" means a —NH$_2$.

"Alkylamino" means a —NHR radical where R is alkyl as defined above, e.g., methylamino, ethylamino, propylamino, or 2-propylamino, and the like.

"Aminoalkyl" means a linear monovalent hydrocarbon radical of one to six carbon atoms or a branched monovalent hydrocarbon radical of three to six carbons substituted with-NR'R" where R' and R" are independently hydrogen, alkyl, haloalkyl, hydroxyalkyl, alkoxyalkyl, or alkylcarbonyl, each as defined herein, e.g., aminomethyl, aminoethyl, methylaminomethyl, and the like.

"Alkoxy" means a -OR radical where R is alkyl as defined above, e.g., methoxy, ethoxy, propoxy, or 2-propoxy, n-, iso-, or tert-butoxy, and the like.

"Alkoxyalkyl" means a linear monovalent hydrocarbon radical of one to six carbon atoms or a branched monovalent hydrocarbon radical of three to six carbons substituted with at least one alkoxy group, such as one or two alkoxy groups, as defined above, e.g., 2-methoxyethyl, 1-, 2-, or 3-methoxypropyl, 2-ethoxyethyl, and the like.

"Alkoxycarbonyl" means a —C(O)OR radical where R is alkyl as defined above, e.g., methoxycarbonyl, ethoxycarbonyl, and the like.

"Alkylcarbonyl" means a —C(O)R radical where R is alkyl as defined herein, e.g., methylcarbonyl, ethylcarbonyl, and the like.

"Aryl" means a monovalent monocyclic or bicyclic aromatic hydrocarbon radical of 6 to 10 ring atoms e.g., phenyl or naphthyl.

"Aralkyl" means a -(alkylene)-R radical where R is aryl as defined above, e.g., benzyl, phenethyl, and the like.

"Bicyclic cycloalkyl" means a fused bicyclic saturated monovalent hydrocarbon radical of six to ten carbon atoms, and is optionally substituted with one or two substituents independently selected from alkyl, halo, alkoxy, hydroxy, and cyano. Examples include, but are not limited to, decalin, octahydro-1H-indene, and the like.

"Cycloalkyl" means a monocyclic saturated monovalent hydrocarbon radical of three to ten carbon atoms optionally substituted with one or two substituents independently selected from alkyl, alkyldienyl, halo, alkoxy, hydroxy, cyano, haloalkyldienyl and cyanoalkyl. Examples include, but are not limited to, cyclopropyl, cyclobutyl, cyclopentyl, cyclohexyl, 1-cyanocycloprop-1-yl, 1-cyanomethylcycloprop-1-yl, 3-fluorocyclohexyl, and the like. Cycloalkyl may include cycloalkylene as defined herein.

"Cycloalkylalkyl" means a -(alkylene)-R radical where R is cycloalkyl as defined above, e.g., cyclopropylmethyl, cyclohexylmethyl, and the like.

"Cycloalkylene" means a divalent cycloalkyl, as defined above, unless stated otherwise.

"Cycloalkenyl" means a monocyclic monovalent hydrocarbon radical of three to ten carbon atoms containing one or two double bond(s) optionally substituted with one or two substituents independently selected from alkyl, halo, alkoxy, hydroxy, cyano, and cyanoalkyl. Examples include, but are not limited to, cyclopropenyl, cyclobutenyl, cyclopentenyl, or cyclohexenyl, and the like.

"Oxocycloalkenyl" means a monocyclic monovalent hydrocarbon radical of three to ten carbon atoms containing one or two double bond(s) and an oxo group, and is optionally substituted with one or two substituents independently selected from alkyl, halo, alkoxy, hydroxy, cyano, and cyanoalkyl. Examples include, but are not limited to, 3-oxo-cyclohex-1-enyl, and the like.

"Cyanoalkyl" means a linear monovalent hydrocarbon radical of one to six carbon atoms or a branched monovalent hydrocarbon radical of three to six carbons substituted with cyano e.g., cyanomethyl, cyanoethyl, and the like.

"Carboxy" means —COOH.

"Dialkylamino" means a —NRR' radical where R and R' are alkyl as defined above, e.g., dimethylamino, methylethylamino, and the like.

"Disubstituted amino" means a —NRR' radical where R and R' are independently alkyl, haloalkyl, hydroxyalkyl, alkoxyalkyl, or alkylcarbonyl, each as defined herein, e.g., dimethylamino, ethylmethylamino, bis-hydroxyethylamino, bis-methoxyethylamino, diethylaminoethylamino, and the like.

"Halo" means fluoro, chloro, bromo, or iodo, preferably fluoro or chloro.

"Haloalkyl" means alkyl radical as defined above, which is substituted with one or more halogen atoms, e.g., one to five halogen atoms, such as fluorine or chlorine, including those substituted with different halogens, e.g., —CH$_2$Cl, —CF$_3$, —CHF$_2$, —CH$_2$CF$_3$, —CF$_2$CF$_3$, —CF(CH$_3$)$_2$, and the like. When the alkyl is substituted with only fluoro, it can be referred to in this Application as fluoroalkyl.

"Haloalkoxy" means a-OR radical where R is haloalkyl as defined above e.g., —OCF$_3$, —OCHF$_2$, and the like. When R is haloalkyl where the alkyl is substituted with only fluoro, it is referred to in this Application as fluoroalkoxy.

"Hydroxyalkyl" means a linear monovalent hydrocarbon radical of one to six carbon atoms or a branched monovalent hydrocarbon radical of three to six carbons substituted with one or two hydroxy groups, provided that if two hydroxy groups are present they are not both on the same carbon atom. Representative examples include, but are not limited to, hydroxymethyl, 2-hydroxy-ethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Heterocyclyl" means a saturated or unsaturated monovalent monocyclic group of 4 to 8 ring atoms in which one or two ring atoms are heteroatom selected from N, O, or S (O) n, where n is an integer from 0 to 2, the remaining ring atoms being C, unless stated otherwise. Additionally, one or two ring carbon atoms in the heterocyclyl ring can optionally be replaced by a-CO-group. More specifically the term heterocyclyl includes, but is not limited to, pyrrolidino, piperidino, homopiperidino, 2-oxopyrrolidinyl, 2-oxopiperidinyl, morpholino, piperazino, tetrahydro-pyranyl, thiomorpholino, and the like. When the heterocyclyl ring is unsaturated it can contain one or two ring double bonds provided that the ring is not aromatic. When the heterocyclyl group contains at least one nitrogen atom, it is also referred to herein as heterocycloamino and is a subset of the heterocyclyl group.

"Heterocyclylalkyl" or "heterocycloalkyl" means a -(alkylene)-R radical where R is heterocyclyl ring as defined above e.g., tetraydrofuranylmethyl, piperazinylmethyl, morpholinylethyl, and the like.

"Heterocyclylene" means a divalent heterocyclyl, as defined above, unless stated otherwise. When heterocyclene contains 4, 5, or 6 rings atoms, it may be referred to herein as 4 to 6 membered heterocyclylene.

"Heteroaryl" means a monovalent monocyclic or bicyclic aromatic radical of 5 to 10 ring atoms, unless otherwise stated, where one or more, (in one embodiment, one, two, or three), ring atoms are heteroatom selected from N, O, or S, the remaining ring atoms being carbon. Representative examples include, but are not limited to, pyrrolyl, thienyl, thiazolyl, imidazolyl, furanyl, indolyl, isoindolyl, oxazolyl, isoxazolyl, benzothiazolyl, benzoxazolyl, quinolinyl, isoquinolinyl, pyridinyl, pyrimidinyl, pyrazinyl, pyridazinyl, triazolyl, tetrazolyl, and the like. As defined herein, the terms "heteroaryl" and "aryl" are mutually exclusive. When the heteroaryl ring contains 5- or 6 ring atoms it is also referred to herein as 5- or 6-membered heteroaryl.

"Heteroarylene" means a divalent heteroaryl radical as defined above.

"Heteroaralkyl" means a -(alkylene)-R radical where R is heteroaryl as defined above, e.g., pyridinylmethyl, and the like. When the heteroaryl ring in heteroaralkyl contains 5- or 6 ring atoms it is also referred to herein as 5- or 6-membered heteroaralkyl.

The phrase "R$^2$ and R$^9$ are attached to the ring carbon atom that is meta to the ring carbon attached to R$^1$" means the R$^2$ and R$^9$ are located as indicated below:

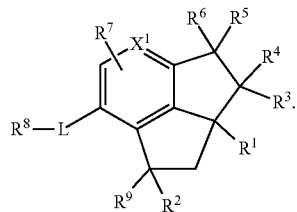

The term "oxo," as used herein, alone or in combination, refers to =(O).

When needed, any definition herein may be used in combination with any other definition to describe a composite structural group. By convention, the trailing element of any such definition is that which attaches to the parent moiety. For example, the composite group alkoxyalkyl means that an alkoxy group attached to the parent molecule through an alkyl group.

The present disclosure also includes protected derivatives of compounds of Formula (IA) or (I). For example, when compounds of Formula (IA) or (I) contain groups such as hydroxy, carboxy, thiol or any group containing a nitrogen atom(s), these groups can be protected with suitable protecting groups. A comprehensive list of suitable protective groups can be found in T.W. Greene, *Protective Groups in Organic Synthesis*, 5$^{th}$ Ed., John Wiley & Sons, Inc. (2014), the disclosure of which is incorporated herein by reference in its entirety. The protected derivatives of compounds of the present disclosure can be prepared by methods well known in the art.

The present disclosure also includes polymorphic forms of compounds of Formula (IA) or (I) or a pharmaceutically acceptable salt thereof. Polymorphs are different crystalline forms of a compound that differ in arrangements of the molecules of that compound in a crystal lattice. Therefore, a single compound may give riese to a variety of polymorphic forms. The polymorphs of a compound usually have different melting points, solubilities, densities and optical properties. Polymorphic forms of a compound can be distinguished by a number of techniques such as X-ray diffractometry, IR or Raman spectroscopy.

The term "prodrug" refers to a compound that is made more active in vivo. Certain compounds of Formula (IA) or (I) may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds of Formula (IA) or (I) are structurally modified forms of the compound that readily undergo chemical changes under physiological conditions to provide the active compound. Prodrugs are often useful because, in some situations, they may be easier to administer than the compound, or parent drug. They may, for instance, be bioavailable by oral administration whereas the parent drug is not. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound of Formula (IA) or (I).

A "pharmaceutically acceptable salt" of a compound means a salt that is pharmaceutically acceptable and that possesses the desired pharmacological activity of the parent compound. Such salts include:

acid addition salts, formed with inorganic acids such as hydrochloric acid, hydrobromic acid, sulfuric acid, nitric acid, phosphoric acid, and the like; or formed with organic acids such as formic acid, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It is understood that the pharmaceutically acceptable salts are non-toxic. Additional information on suitable pharmaceutically acceptable salts can be found in *Remington's Pharmaceutical Sciences*, 17th ed., Mack Publishing Company, Easton, PA, 1985, which is incorporated herein by reference in its entirety.

The compounds of Formula (IA) or (I) may have asymmetric centers. Compounds of Formula (IA) or (I) containing an asymmetrically substituted atom may be isolated in optically active or racemic forms. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. All chiral, diastereomeric, all mixtures of chiral or diasteromeric forms, and racemic forms are within the scope of this disclosure, unless the specific stereochemistry or isomeric form is specifically indicated. It will also be understood by a person of ordinary skill in the art that when a compound is denoted as (R) stereoisomer, it may contain the corresponding (S) stereoisomer as an impurity and vice versa.

Certain compounds of Formula (IA) or (I) can exist as tautomers and/or geometric isomers. All possible tautomers and cis and trans isomers, as individual forms and mixtures thereof are within the scope of this disclosure. Additionally, as used herein the term alkyl includes all the possible isomeric forms of said alkyl group albeit only a few examples are set forth. Furthermore, when the cyclic groups such as aryl, heteroaryl, heterocyclyl are substituted, they include all the positional isomers albeit only a few examples are set forth. Furthermore, all hydrates of a compound of Formulae (IA) and (I) are within the scope of this disclosure.

The compounds of Formula (IA) or (I) may also contain unnatural amounts of isotopes at one or more of the atoms that constitute such compounds. Unnatural amounts of an isotope may be defined as ranging from the amount found in nature to an amount 100% of the atom in question. that differ only in the presence of one or more isotopically enriched atoms. Exemplary isotopes that can be incorporated into a compound of Formula (IA) or (I) (and any embodiment thereof disclosed herein including specific compounds) include isotopes of hydrogen, carbon, nitrogen, oxygen, phosphorus, sulfur, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$, and $^{125}I$, respectively. Isotopically-labeled compounds (e.g., those labeled with $^{3}H$ and $^{14}C$) can be useful in compound or substrate tissue distribution assays. Tritiated (i.e., $^{3}H$) and carbon-14 (i.e., $^{14}C$) isotopes can be useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements). In some embodiments, in compounds disclosed herein, including in Table 1 below one or more hydrogen atoms are replaced by $^{2}H$ or $^{3}H$, or one or more carbon atoms are replaced by $^{13}C$- or $^{14}C$-enriched carbon. Positron emitting isotopes such as $^{15}O$, $^{13}N$, $^{11}C$, and $^{15}F$ are useful for positron emission tomography (PET) studies to examine substrate receptor occupancy. Isotopically labeled compounds can generally be prepared by following procedures analogous to those disclosed in the Schemes or in the Examples herein, by substituting an isotopically labeled reagent for a non-isotopically labeled reagent.

Certain structures provided herein are drawn with one or more floating substituents. Unless provided otherwise or otherwise clear from the context, the substituent(s) may be present on any atom of the ring to which it is attached, where chemically feasible and valency rules permitting. For example, in the structure:

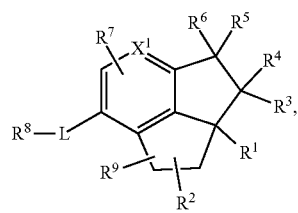

the R⁷ substituent can replace any hydrogen on the benzo portion of the tricyclic ring, including the hydrogen of CH when X¹ is CH.

"Optionally substituted aryl" means aryl that is optionally substituted with one, two, or three substituents independently selected from alkyl, hydroxyl, cycloalkyl, carboxy, alkoxycarbonyl, hydroxy, alkoxy, alkylthio, alkylsulfonyl, amino, alkylamino, dialkylamino, halo, haloalkyl, haloalkoxy, and cyano.

"Optionally substituted heteroaryl" means heteroaryl as defined above that is optionally substituted with one, two, or three substituents independently selected from alkyl, alkylthio, alkylsulfonyl, hydroxyl, cycloalkyl, carboxy, alkoxycarbonyl, hydroxy, alkoxy, halo, haloalkyl, haloalkoxy, amino, alkylamino, dialkylamino, and cyano.

"Optionally substituted heterocyclyl" means heterocyclyl as defined above that is optionally substituted with one, two, or three substituents independently selected from alkyl, alkylthio, alkylsulfonyl, hydroxyl, cycloalkyl, carboxy, alkoxycarbonyl, hydroxy, hydroxyalkyl, alkoxy, alkoxyalkyl, aminoalkyl, halo, haloalkyl, haloalkoxy, and cyano, unless stated otherwise.

"Optionally substituted heterocyclylene" is divalent optionally substituted heterocyclyl as defined above.

A "pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient.

"Spirocycloalkyl" means a saturated bicyclic ring having 6 to 10 ring carbon atoms wherein the rings are connected through only one atom, the connecting atom is also called the spiroatom, most often a quaternary carbon ("spiro carbon"). The spirocycloalkyl ring is optionally substituted with one or two substituents independently selected from alkyl, halo, alkoxy, hydroxy, and cyano. Representative examples include, but are not limited to, spiro[3.3]heptane, spiro[3.4]octane, spiro[3.5]nonane, spiro[4.4]nonane (1:2:1: 1), and the like.

"Spiroheterocyclyl" means a saturated bicyclic ring having 6 to 10 ring atoms in which one, two, or three ring atoms are heteroatom selected from N, O, or S (O) n, where n is an integer from 0 to 2, the remaining ring atoms being C and the rings are connected through only one atom, the connecting atom is also called the spiroatom, most often a quaternary carbon ("spiro carbon"). The spiroheterocyclyl ring is optionally substituted with one, two, or three substituents independently selected from alkyl, alkylthio, alkylsulfonyl, hydroxyl, cycloalkyl, carboxy, alkoxycarbonyl, hydroxy, hydroxyalkyl, alkoxy, alkoxyalkyl, aminoalkyl, halo, haloalkyl, haloalkoxy, and cyano. Representative examples include, but are not limited to, 2,6-diazaspiro[3.3]heptane, 2,6-diazaspiro[3.4]octane, 2-azaspiro[3.4]octane, 2-azaspiro [3.5]nonane, 2,7-diazaspiro[4.4]nonane, and the like.

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass ±10%, preferably ±5%, the recited value and the range is included.

The phrase "heteroaryl wherein the heteroaryl is optionally substituted with $R^d$, $R^e$, and $R^f$ independently selected from hydrogen, alkyl, haloalkyl, haloalkoxy, alkoxy, hydroxy, halo, and cyano" in the definition of $R^9$ in Formula (I) (and similar phrases used to define other groups in Formula (I)) is intended to cover heteroaryl that is unsubstituted and heteroaryl that is substituted with $R^d$, $R^e$, and $R^f$.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a disease or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease;

(2) inhibiting the disease, i.e., arresting or reducing the development of the disease or its clinical symptoms; or (3) relieving the disease, i.e., causing regression of the disease or its clinical symptoms.

A "therapeutically effective amount" means the amount of a compound of the present disclosure or a pharmaceutically acceptable salt thereof that, when administered to a patient for treating a disease, is sufficient to affect such treatment for the disease. The "therapeutically effective amount" will vary depending on the compound, the disease and its severity and the age, weight, etc., of the mammal to be treated.

The terms "inhibiting" and "reducing," or any variation of these terms in relation of HIF-2a, includes any measurable decrease or complete inhibition to achieve a desired result. For example, there may be a decrease of about, at most about, or at least about 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of HIF-2α activity compared to normal.

EMBODIMENTS

In further embodiments 1-30 below, the present disclosure includes:

1A. In embodiment 1A, the compound of Formula (IA):

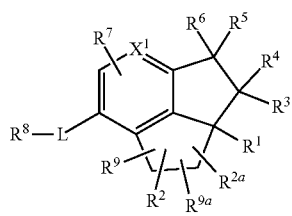

as described in the first aspect of the Summary above. In a subembodiment of embodiment 1A, $R^{2a}$ and $R^{9a}$ are independently hydrogen or deuterium.

1. In embodiment 1, the compound of Formula (I):

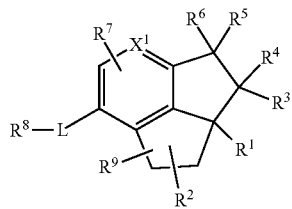

is as described in the first embodiment of the aspect in the Summary above.

In a first subembodiment of embodiment 1A or 1 or subembodiment within embodiment 1A, the compound of Formula (IA) or (I), or a pharmaceutical salt thereof, is wherein $R^1$ is hydroxy.

In a second subembodiment of embodiment 1A or 1 or subembodiment within embodiment 1A, the compound of Formula (IA) or (I), or a pharmaceutical salt thereof, is wherein $R^1$ is amino or halo, preferably $R^1$ is amino.

In a third subembodiment of embodiment 1A or 1 or subembodiment within embodiment 1A, the compound of Formula (IA) or (I), or a pharmaceutical salt thereof, is wherein $R^1$ is —OCOR$^{10}$, —OCOOR$^{11}$, —OCONR$^{12}$R$^{13}$, —OCHR$^{14}$OCOR$^{15}$ or —OCHR$^{14}$OCOOR$^{15a}$ where $R^{10}$, $R^{11}$, $R^{15}$, and $R^{15a}$ are as defined in the Summary.

In a fourth subembodiment of embodiment 1A or 1 or subembodiment within embodiment 1A, the compound of Formula (IA) or (I), or a pharmaceutical salt thereof, is wherein $R^1$ is -OP(O)(OH)$_2$, or —OCH$_2$OP(O)(OH)$_2$.

In a fifth subembodiment of embodiment 1A or 1 or subembodiment within embodiment 1A, and subembodiments contained therein (i.e. first, second, third, and fourth subembodiments above), the compounds of Formula (IA) or (I), or a pharmaceutical salt thereof, are those wherein $R^6$ is halo, preferably $R^6$ is fluoro.

In a sixth subembodiment of embodiment 1A or 1 or subembodiment within embodiment 1A, and subembodiments contained therein (i.e. first, second, third, and fourth subembodiments), the compounds of Formula (IA) or (I), or a pharmaceutical salt thereof, are those wherein $R^6$ is alkyl, preferably $R^6$ is methyl.

In a seventh subembodiment of embodiment 1A or 1 or subembodiment within embodiment 1A, and subembodiments contained therein (i.e. first, second, third, and fourth subembodiments), the compounds of Formula (IA) (I), or a pharmaceutical salt thereof, are those wherein $R_6$ is hydrogen or deuterium.

In an eighth subembodiment of embodiment 1A or 1 or subembodiment within embodiment 1A, and subembodiments contained therein (i.e. first, second, third, and fourth subembodiments), the compounds of Formula (1A) or (I), or a pharmaceutical salt thereof, are those wherein Reis cycloalkyl, preferably $R^6$ is cyclopropyl, cyclobutyl, cyclopentyl, or cyclohexyl.

In a ninth subembodiment of embodiment 1A or 1 or subembodiment within embodiment 1A, and subembodiments contained therein (i.e. first, second, third, fourth, fifth, six, seventh, and eighth subembodiments above), the compounds of Formula (IA) or (I), or a pharmaceutical salt thereof, are those wherein $R^5$ is halo or haloalkyl, preferably $R^5$ is difluoromethyl or trifluoromethyl.

In a tenth subembodiment of embodiment 1A or 1 or subembodiment within embodiment 1A, and subembodiments contained therein (i.e. first, second, third, fourth, fifth, six, seventh, and eighth subembodiments above), the compounds of Formula (IA) or (I), or a pharmaceutical salt thereof, are those wherein $R^5$ is alkyl, preferably $R^5$ is methyl or ethyl.

In an eleventh subembodiment of embodiment 1A or 1 or subembodiment within embodiment 1A, and subembodiments contained therein (i.e. first, second, third, fourth, fifth, six, seventh, and eighth subembodiments), the compounds of Formula (IA) or (I), or a pharmaceutical salt thereof, are those wherein $R^5$ is hydrogen or alkoxy.

In a twelfth subembodiment of embodiment 1A or 1 or subembodiment within embodiment 1A, and subembodiments contained therein (i.e. first, second, third, and fourth subembodiments), the compounds of Formula (IA) or (I), or a pharmaceutical salt thereof, are those wherein $R^5$ and $R^6$ together with the carbon to which they are attached form 3 to 6 membered cycloalkylene, preferably $R^5$ and $R^6$ together with the carbon to which they are attached form cyclopropylene, cyclobutylene, or cyclopentylene each optionally substituted with one or two fluoro.

In a thirteenth subembodiment of embodiment 1A or 1 or subembodiment within embodiment 1A, and subembodiments contained therein (i.e. first, second, third, and fourth subembodiments), the compounds of Formula (IA) or (I), or a pharmaceutical salt thereof, are those wherein $R^5$ and $R^6$ together with the carbon to which they are attached form 4 to 6 membered optionally substituted heterocyclylene, preferably $R^5$ and $R^6$ together with the carbon to which they are attached form

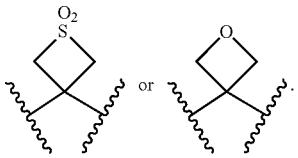 [SMILES: *C1(*)CS(=O)(=O)C1 ; *C1(*)COC1]

In a fourteenth subembodiment of embodiment 1A or 1 or subembodiment within embodiment 1A, and subembodiments contained therein (i.e. first to eleventh subembodiments), the compounds of Formula (IA) or (I), or a pharmaceutical salt thereof, are those wherein $R^3$ and $R^4$ are independently halo.

In a fifteenth subembodiment of embodiment 1A or 1 or subembodiment within embodiment 1A, and subembodiments contained therein (i.e. first to eleventh subembodiments), the compounds of Formula (IA) or (I), or a pharmaceutical salt thereof, are those wherein $R^3$ is halo and $R^4$ is hydrogen.

In a sixteenth subembodiment of embodiment 1A or 1 or subembodiment within embodiment 1A, and subembodiments contained therein (i.e. first to fifteenth subembodiments), the compounds of Formula (IA) or (I), or a pharmaceutical salt thereof, are those wherein $X^1$ is CH or $CR^7$.

In a seventeenth subembodiment of embodiment 1A or 1 or subembodiment within embodiment 1A, and subembodiments contained therein (i.e. first to fifteenth subembodiments), the compounds of Formula (IA) or (I), or a pharmaceutical salt thereof, are those wherein $X^1$ is N.

2A. In embodiment 2A, the compound of embodiment 1A or a pharmaceutically acceptable salt thereof, has the structure of formula (IIa1) or (IIb1):

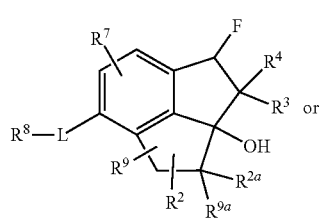
(IIa1)

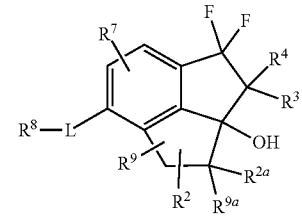
(IIb1)

In a first subembodiment of embodiment 2A the compound or subembodiment within embodiment 1A, or a pharmaceutically acceptable salt thereof, has the structure of formula (IIa1). In a second subembodiment of embodiment 2A the compound or a pharmaceutically acceptable salt thereof, has the structure of formula (IIb1).

2Aa. In embodiment 2Aa, the compound of embodiment 1A or subembodiment within embodiment 1A, or a pharmaceutically acceptable salt thereof, has the structure of formula (IIa1') or (IIb1')

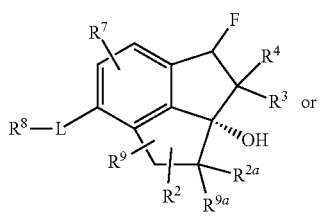
(IIa1')

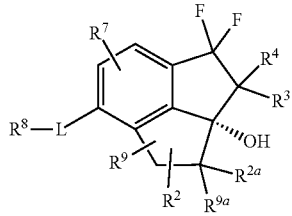
(IIb1')

In a first subembodiment of embodiment 2Aa the compound or a pharmaceutically acceptable salt thereof, has the structure of formula (IIa1'). In a second subembodiment of embodiment 2Aa the compound or a pharmaceutically acceptable salt thereof, has the structure of formula (IIb1').

2. In embodiment 2, the compound of embodiment 1 or a pharmaceutically acceptable salt thereof, has the structure of formula (IIa) or (IIb):

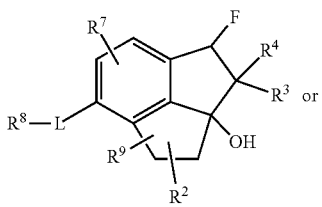
(IIa)

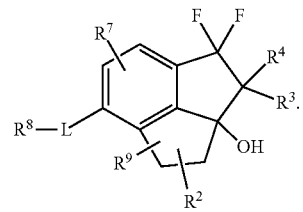
(IIb)

In a first subembodiment of embodiment 2 the compound or a pharmaceutically acceptable salt thereof, has the structure of formula (IIa). In a second subembodiment of embodiment 2 the compound or a pharmaceutically acceptable salt thereof, has the structure of formula (IIb).

2a. In embodiment 2a, the compound of embodiment 1 or a pharmaceutically acceptable salt thereof, has the structure of formula (IIa') or (IIb'):

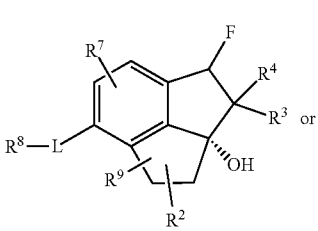
(IIa')

(IIb')

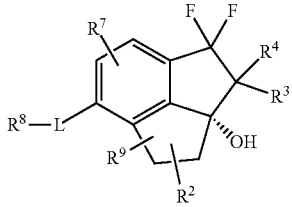

In a first subembodiment of embodiment 2a the compound or a pharmaceutically acceptable salt thereof, has the structure of formula (IIa'). In a second subembodiment of embodiment 2a the compound or a pharmaceutically acceptable salt thereof, has the structure of formula (IIb').

3A. In embodiment 3A, the compound of embodiment 1A or subembodiment within embodiment 1A, or a pharmaceutically acceptable salt thereof, has the structure of formula (IIIa1) or (IIIb1):

(IIIa1)

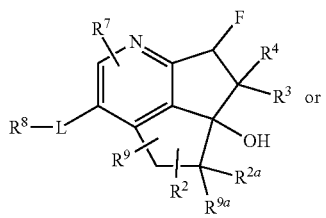

(IIIb1)

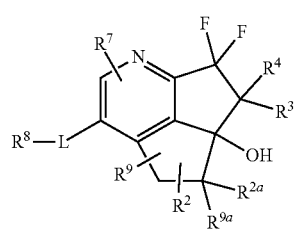

In a first subembodiment of embodiment 3A the compound or a pharmaceutically acceptable salt thereof, has the structure of formula (IIIa1). In a second subembodiment of embodiment 3A the compound or a pharmaceutically acceptable salt thereof, has the structure of formula (IIIb1).

3Aa. In embodiment 3Aa, the compound of embodiment 1A or a pharmaceutically acceptable salt thereof, has the structure of formula (IIIa1') or (IIIb1'):

(IIIa1')

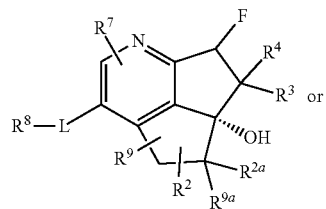

(IIIb1')

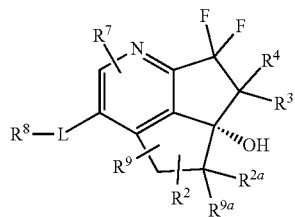

In a first subembodiment of embodiment 3 Aa the compound or a pharmaceutically acceptable salt thereof, has the structure of formula (IIIa1'). In a second subembodiment of embodiment 3 Aa the compound or a pharmaceutically acceptable salt thereof, has the structure of formula (IIIb1').

3. In embodiment 3, the compound of embodiment 1 or a pharmaceutically acceptable salt thereof, has the structure of formula (IIIa) or (IIIb):

(IIIa)

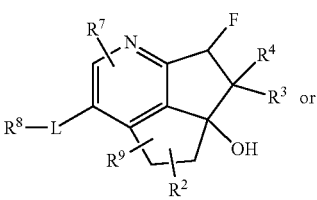

(IIIb)

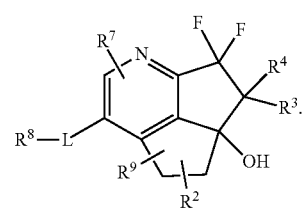

In a first subembodiment of embodiment 3, wherein the compound or a pharmaceutically acceptable salt thereof, has the structure of formula (IIIa). In a second subembodiment of embodiment 3, the compound or a pharmaceutically acceptable salt thereof, has the structure of formula (IIIb).

3a. In embodiment 3a, the compound of embodiment 1 or a pharmaceutically acceptable salt thereof, has the structure of formula (IIIa') or (IIIb'):

(IIIa')

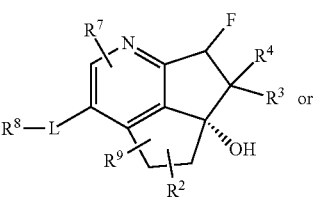

(IIIb')

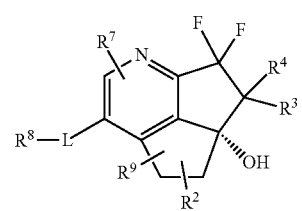

In a first subembodiment of embodiment 3a, the compound or a pharmaceutically acceptable salt thereof, has the structure of formula (IIIa'). In a second subembodiment of embodiment 3a, the compound or a pharmaceutically acceptable salt thereof, has the structure of formula (IIIb').

4. In embodiment 4, the compound of embodiment 1 or a pharmaceutically acceptable salt thereof, has the structure of formula (IVa) or (IVb):

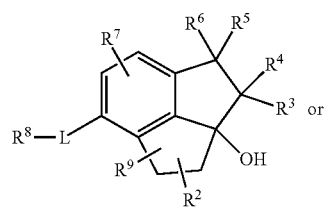

(IVa)

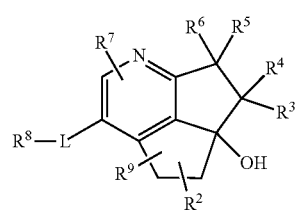

(IVb)

where $R^5$ and $R^6$ together with the carbon to which they are attached form 3 to 6 membered cycloalkylene, preferably cyclopropylene, cyclobutylene or cyclopentylene optionally substituted with one or two fluoro. In a first subembodiment of embodiment 4, the compound or a pharmaceutically acceptable salt thereof, has the structure of formula (IVa). In a second subembodiment of embodiment 4, the compound or a pharmaceutically acceptable salt thereof, has the structure of formula (IVb).

5. In embodiment 5, the compound of embodiment 1 or a pharmaceutically acceptable salt thereof, has the structure of formula (Va) or (Vb):

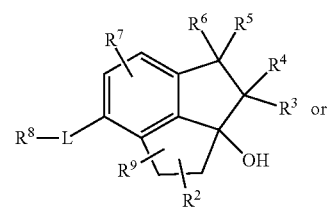

(Va)

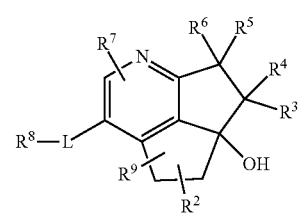

(Vb)

where $R^5$ and $R^6$ together with the carbon to which they are attached form 4 to 6 membered optionally substituted heterocyclylene, preferably $R^5$ and $R^6$ together with the carbon to which they are attached form

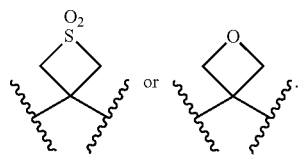 [SMILES: *C1(*)CS(=O)(=O)C1 ; *C1(*)COC1]

In a first subembodiment of embodiment 5, the compound or a pharmaceutically acceptable salt thereof, has the structure of formula (Va). In a second subembodiment of embodiment 5, the compound or a pharmaceutically acceptable salt thereof, has the structure of formula (Vb).

6. In embodiment 6, the compound of embodiment 1 or a pharmaceutically acceptable salt thereof, has the structure of formula (VIa) or (VIb):

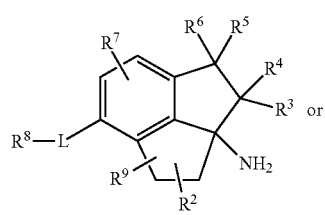

(VIa)

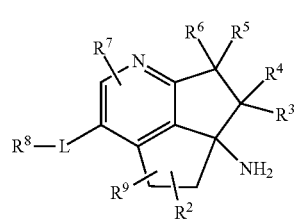

(VIb)

where $R^5$ and $R^6$ together with the carbon to which they are attached form 3 to 6 membered cycloalkylene, preferably cyclopropylene, cyclobutylene or cyclopentylene optionally substituted with one or two fluoro. In a first subembodiment of embodiment 6, the compound or a pharmaceutically acceptable salt thereof, has the structure of formula (VIa). In a second subembodiment of embodiment 6, the compound or a pharmaceutically acceptable salt thereof, has the structure of formula (VIb).

7A. In embodiment 7A, the compound of embodiment 1A or a pharmaceutically acceptable salt thereof, has the structure of formula (VIIa1) or (VIIb1):

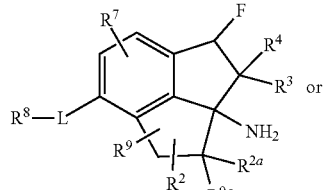

(VIIa1)

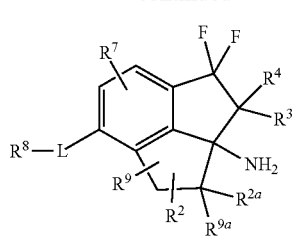

(VIIb1)

In a first subembodiment of embodiment 7A the compound or a pharmaceutically acceptable salt thereof, has the structure of formula (VIIa1). In a second subembodiment of embodiment 7A the compound or a pharmaceutically acceptable salt thereof, has the structure of formula (VIIb1).

7. In embodiment 7, the compound of embodiment 1 or a pharmaceutically acceptable salt thereof, has the structure of formula (VIIa) or (VIIb):

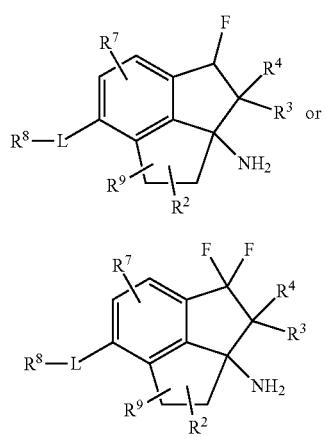

In a first subembodiment of embodiment 7, the compound or a pharmaceutically acceptable salt thereof, has the structure of formula (VIIa). In a second subembodiment of embodiment 7, the compound or a pharmaceutically acceptable salt thereof, has the structure of formula (VIIb).

8. In embodiment 8, the compound of any one of embodiments 1A to 7 and subembodiments contained therein (e.g., subembodiment within embodiment 1A, subembodiments first to seventeenth of embodiment 1A and/or 1 and subembodiments of embodiments 2A to 7) or a pharmaceutically acceptable salt thereof, are where one of $R^3$ and $R^4$ is halo, preferably fluoro. In a first subembodiment, $R^3$ is fluoro and $R^4$ is hydrogen.

9. In embodiment 9, the compound of any one of embodiments 1A to 7 and subembodiments contained therein (e.g., subembodiment within embodiment 1A, subembodiments first to seventeenth of embodiment 1A and/or 1 and subembodiments of embodiments 2A to 7) or a pharmaceutically acceptable salt thereof, are where $R^3$ and $R^4$ are halo, preferably $R^3$ and $R^4$ are fluoro.

10. In embodiment 10, the compound of any one of embodiments 1A to 9 and subembodiments contained therein (e.g., subembodiment within embodiment 1A, subembodiments first to seventeenth of embodiment 1A and/or 1 and subembodiments of embodiments 2A to 9) or a pharmaceutically acceptable salt thereof, is wherein L is O, S, SO, $SO_2$, or NH. In a first subembodiment of embodiment 10, L is O. In a second subembodiment of embodiment 10, L is S. In a third subembodiment of embodiment 10, L is NH. In a fourth subembodiment of embodiment 10, L is SO or $SO_2$.

11. In embodiment 11, the compound of any one of embodiments 1A to 10 and subembodiments contained therein (e.g., subembodiment within embodiment 1A, subembodiments first to seventeenth of embodiment 1A and/or 1 and subembodiments of embodiments 2A to 10) or a pharmaceutically acceptable salt thereof, is wherein $R^8$ is cycloalkyl, cycloalkenyl, bicyclic cycloalkyl, oxocycloalkenyl, cycloalkylalkyl, aryl, aralkyl, heterocyclyl, spirocycloalkyl, spiroheterocyclyl, heterocyclylalkyl, heteroaryl, or heteroaralkyl wherein aryl or heteroaryl, each by itself or as part of aralkyl or heteroaralkyl, or heterocyclyl by itself or as part of heterocyclylalkyl is substituted with $R^a$, $R^b$, and $R^c$ independently selected from hydrogen, alkyl, haloalkyl, haloalkyloxy, alkoxy, hydroxy, halo, cyano, hydroxyalkyl, alkoxyalkyl, aminoalkyl, alkenyl, alkynyl, alkylidenyl, optionally substituted aryl, optionally substituted heteroaryl, and optionally substituted heterocyclyl.

12A. In embodiment 12A, the compound of any one of embodiments 1A, 2A, 2Aa, 3A, 3Aa, 7A, and 8 to 10 and subembodiments contained therein or a pharmaceutically acceptable salt thereof, is wherein $R^8$ is phenyl substituted with $R^a$, $R^b$, $R^c$, $R^g$ and $R^h$ wherein $R^a$, $R^b$, and $R^c$ are independently selected from hydrogen, deuterium, alkyl, haloalkyl, haloalkyloxy, alkoxy, hydroxy, halo, cyano, hydroxyalkyl, alkoxyalkyl, aminoalkyl, optionally substituted aryl, optionally substituted heteroaryl, and optionally substituted heterocyclyl and $R^g$ and $R^h$ are independently selected from hydrogen, deuterium, and halo. In a first subembodiment of embodiment 12A, $R^a$, $R^b$, and $R^c$ are independently selected from hydrogen, deuterium, alkyl, alkoxy, hydroxy, halo, haloalkyl, haloalkoxy, and cyano. In a second subembodiment of embodiment 12A, $R^a$, $R^b$, and $R^o$ are independently selected from hydrogen, deuterium, methyl, methoxy, hydroxy, chloro, fluoro, cyano, difluoromethyl, trifluoromethyl, difluoromethoxy, and trifluoromethoxy and $R^g$ and $R^h$ are independently hydrogen or deuterium. In a third subembodiment of embodiment 12A, $R^8$ is 3-chloro-5-fluorophenyl, 3,5-difluorophenyl, 3-fluoro-5-methoxyphenyl, 3-cyano-5-fluorophenyl, 3-chloro-5-cyanophenyl, 3-cyano-5-methylphenyl, 3-chloro-4-fluorophenyl, 3-chloro-5-fluorophenyl, 3-fluoro-5-methylphenyl, 3-cyanophenyl, 3-trifluoromethylphenyl, 3,4-dichlorophenyl, 3-chloro-2-methylphenyl, 3,5-dichlorophenyl, 3,5-dimethylphenyl, 2-chloro-6-methylphenyl, 2,6-difluorophenyl, 3,4,5-trifluorophenyl, 3,4-difluorophenyl, 4-fluoro-3-methylphenyl, 3-cyano-4-fluorophenyl, 3-cyano-5-difluoromethylphenyl or 3-cyano-5-fluoro-2,4,6-trideuteriophenyl. In a fourth subembodiment of embodiment 12A, $R^8$ is 3-cyano-5-fluorophenyl or 3-cyano-5-fluoro-2,4,6-trideuteriophenyl.

12. In embodiment 12, the compound of any one of embodiments 2, 2a, 3, 3a to 6, and 7 to 10 and subembodiments contained therein (e.g., subembodiments first to seventeenth of embodiment 1 and subembodiments of embodiments 2, 2a,3, 3a to 6 and 7 to 10) or a pharmaceutically acceptable salt thereof, is wherein $R^8$ is phenyl substituted with $R^a$, $R^b$, and $R^c$ independently selected from hydrogen, alkyl, haloalkyl, haloalkyloxy, alkoxy, hydroxy, halo, cyano, hydroxyalkyl, alkoxyalkyl, aminoalkyl, optionally substituted aryl, optionally substituted heteroaryl, and optionally substituted heterocyclyl. In a first subembodiment of embodiment 12, $R^a$, $R^b$, and $R^c$ are independently selected from hydrogen, alkyl, alkoxy, hydroxy, halo, haloalkyl, haloalkoxy, and cyano. In a second subembodiment of embodiment 12, $R^a$, $R^b$, and $R^c$ are independently selected from hydrogen, methyl, methoxy, hydroxy, chloro, fluoro, cyano, difluoromethyl, trifluoromethyl, difluoromethoxy, and trifluoromethoxy. In a third subembodiment of embodiment 12, $R^8$ is 3-chloro-5-fluorophenyl, 3,5-difluorophenyl, 3-fluoro-5-methoxyphenyl, 3-cyano-5-fluorophenyl, 3-chloro-5-cyanophenyl, 3-cyano-5-methylphenyl, 3-chloro-4-fluorophenyl, 3-chloro-5-fluorophenyl, 3-fluoro-5-methylphenyl, 3-cyanophenyl, 3-trifluoromethylphenyl, 3,4-dichlorophenyl, 3-chloro-2-methylphenyl, 3,5-dichlorophenyl, 3,5-dimethylphenyl, 2-chloro-6-methylphenyl, 2,6-difluorophenyl, 3,4,5-trifluorophenyl, 3,4-difluorophenyl, 4-fluoro-3-methylphenyl, 3-cyano-4-fluorophenyl, or 3-cyano-5-difluoromethylphenyl. In a fourth subembodiment of embodiment 12, $R^8$ is 3-cyano-5-fluorophenyl.

13. In embodiment 13, the compound of any one of embodiments 1A to 10 and subembodiments contained therein (e.g., subembodiment within embodiment 1A, subembodiments first to seventeenth of embodiment 1A and/or 1 and subembodiments of embodiments 2A to 10) or a pharmaceutically acceptable salt thereof, is wherein $R^8$ is cycloalkyl or cycloalkylalkyl each optionally substituted with one or two substituents independently selected from alkyl, halo, alkoxy, cyano, alkyldienyl, haloalkyldienyl, and hydroxy. In a first subembodiment of embodiment 13, $R^8$ is cyclopropylmethyl, cyclopropylethyl, cyclobutylmethyl, cyclobutylethyl, cyclopentylmethyl, cyclopentylethyl, or cyclohexylmethyl, each optionally substituted with one or two substituents independently selected from alkyl, halo, alkoxy, cyano, and hydroxy. In a second subembodiment of embodiment 13, $R^6$ is cyclopropylmethyl, cyclopropylethyl, cyclobutylmethyl, cyclobutylethyl, cyclopentylmethyl, cyclopentylethyl, or cyclohexylmethyl, each substituted with one or two substituents independently selected from hydrogen, methyl, methoxy, cyano, and fluoro, preferably $R^8$ is cyclopropylmethyl, 1-cyanocyclopropylmethyl, cyclobutylmethyl, 2-fluorocyclopropylmethyl, or 1-cyanocyclobutylmethyl. In a third subembodiment of embodiment 13, $R^8$ is cyclopropyl, cyclobutyl, cyclopentyl, or cyclohexyl, each optionally substituted with one or two substituents independently selected from alkyl, halo, alkoxy, cyano, and hydroxy. In a fourth subembodiment of embodiment 13, $R^8$ is cyclopropyl, cyclobutyl, cyclopentyl, or cyclohexyl, each optionally substituted with one or two substituents independently selected from methyl, cyano, methoxy, and fluoro, preferably, $R^8$ is cyclobutyl, 3-fluorocyclobutyl, 3,3-difluorocyclobutyl, 3-cyanocyclobutyl, 3-fluorocyclohexyl, or 3-cyano-3-methylcyclobutyl.

14. In embodiment 14, the compound of any one of embodiments 1A to 10 and subembodiments contained therein (e.g., subembodiment within embodiment 1A, subembodiments first to seventeenth of embodiment 1A and/or 1 and subembodiments of embodiments 2A to 10) or a pharmaceutically acceptable salt thereof, is wherein $R^8$ is heteroaryl substituted with $R^a$, $R^b$, and $R^c$ independently selected from hydrogen, alkyl, haloalkyl, haloalkyloxy, alkoxy, hydroxy, halo, cyano, hydroxyalkyl, alkoxyalkyl, aminoalkyl, optionally substituted aryl, optionally substituted heteroaryl, and optionally substituted heterocyclyl. In a first subembodiment of embodiment 14, $R^8$ is 5- or 6-membered heteroaryl e.g., pyridyl, pyridazinyl, pyrimidinyl, thienyl, furanyl, thiazolyl, oxazolyl, imidazolyl, or pyrazinyl, each substituted with $R^a$, $R^b$, and $R^c$ wherein $R^a$ and $R^b$ are independently selected from hydrogen, alkyl, alkoxy, hydroxy, halo, haloalkyl, haloalkoxy, and cyano and $R^c$ is selected from hydrogen, alkyl, halo, haloalkyl, and haloalkoxy. In a second subembodiment of embodiment 14, $R^8$ is pyridin-3-yl, pyridin-2-yl, pyridazin-3-yl, pyridazin-4-yl, pyrimidin-5-yl, pyrimidin-2-yl, thien-2-yl, furan-2-yl, thiazol-5-yl, oxazol-5-yl, imidazol-5-yl, furan-3-yl, thien-3-yl, thiazol-4-yl, pyridin-4-yl, oxazol-2-yl, imidazol-2-yl, pyridin-2-yl, pyrazin-2-yl or thiazol-2-yl, each substituted with $R^a$, $R^b$, and $R^c$ wherein $R^a$ and $R^b$ are independently selected from hydrogen, methyl, methoxy, hydroxy, chloro, fluoro, difluoromethyl, trifluoromethyl, difluoromethoxy, and trifluoromethoxy and $R^e$ is selected from hydrogen, methyl, cyano, chloro, fluoro, difluoromethyl, trifluoromethyl, difluoromethoxy, and trifluoromethoxy. In a third subembodiment of embodiment 14, $R^8$ is 5-cyanopyridin-3-yl, 5-chloropyridin-3-yl, or 5-fluoropyridin-3-yl.

15. In embodiment 15, the compound of any one of embodiments 1A to 10 and subembodiments contained therein (e.g., subembodiment within embodiment 1A, subembodiments first to seventeenth of embodiment 1A and/or 1 and subembodiments of embodiments 2A to 10) or a pharmaceutically acceptable salt thereof, is wherein $R^8$ is bicyclic heteroaryl substituted with $R^a$, $R^b$, and $R^c$, wherein $R^a$ and $R^b$ are independently selected from hydrogen, alkyl, alkoxy, hydroxy, halo, haloalkyl, haloalkoxy, and cyano and $R^c$ is selected from hydrogen, alkyl, halo, haloalkyl, haloalkoxy, hydroxyalkyl, alkoxyalkyl, and aminoalkyl.

16. In embodiment 16, the compound of any one of embodiments 1A to 10 and subembodiments contained therein (e.g., subembodiment within embodiment 1A, subembodiments first to seventeenth of embodiment 1A and/or 1 and subembodiments of embodiments 2A to 10) or a pharmaceutically acceptable salt thereof, is wherein $R^8$ is heterocyclyl, wherein heterocyclyl is substituted with $R^a$, $R^b$, and $R^c$ wherein $R^a$ and $R^b$ are independently selected from hydrogen, alkyl, alkoxy, hydroxy, halo, haloalkyl, haloalkoxy, and cyano and $R^e$ is hydrogen, alkyl, halo, haloalkyl, haloalkoxy, hydroxyalkyl, alkoxyalkyl, or aminoalkyl. In a first subembodiment of embodiment 18, $R^8$ is tetrahydrofuranyl, tetrahydropyranyl, or oxetanyl, each independently substituted with $R^a$ and $R^b$ wherein $R^a$ and $R^b$ are independently selected from hydrogen, methyl, and fluoro.

17. In embodiment 17, the compound of any one of embodiments 1A to 10 and subembodiments contained therein (e.g., or subembodiment within embodiment 1A, subembodiments first to seventeenth of embodiment 1A and/or 1 and subembodiments of embodiments 2A to 10) or a pharmaceutically acceptable salt thereof, is wherein $R^8$ is spiroheterocyclyl. In one embodiment, the spiroheterocyclyl ring contains at least one nitrogen atom. In a second embodiment, the spiroheterocyclyl ring contains at least one oxygen atom.

18. In embodiment 18, the compound of any one of embodiments 1A to 17 and subembodiments contained therein (e.g., subembodiment within embodiment 1A, subembodiments first to seventeenth of embodiment 1A and/or 1 and subembodiments of embodiments 2A to 17) or a pharmaceutically acceptable salt thereof, is wherein $R^7$ is hydrogen, methyl, ethyl, methoxy, fluoro, trifluoromethyl or trifluoromethoxy. In a first subembodiment, $R^7$ is hydrogen.

19. In embodiment 19, the compound of any one of embodiments 1A to 18 and subembodiments contained therein (e.g., subembodiment within embodiment 1A, subembodiments first to seventeenth of embodiment 1A and/or 1 and subembodiments of embodiments 2A to 18) or a pharmaceutically acceptable salt thereof, is wherein $R^2$ is hydrogen, fluoro, methyl or ethyl. In a first subembodiment, $R^2$ is hydrogen. In a second subembodiment, $R^2$ is methyl. In a third subembodiment, $R^2$ is fluoro.

20. In embodiment 20, the compound of any one of embodiments 1A to 19 and subembodiments contained therein (e.g., subembodiment within embodiment 1A, subembodiments first to seventeenth of embodiment 1A and/or 1 and subembodiments of embodiments 2A to 19) or a pharmaceutically acceptable salt thereof, is wherein $R^9$ is hydrogen, alkyl, halo, hydroxy, or alkoxy. In a first subembodiment of embodiment 20, $R^9$ is hydrogen, methyl, methoxy, or fluoro.

21. In embodiment 21, the compound of any one of embodiments 1A to 20 and subembodiments contained therein (e.g., subembodiment within embodiment 1A, subembodiments first to seventeenth of embodiment 1A and/or 1 and subembodiments of embodiments 2A to 20) or a pharmaceutically acceptable salt thereof, is wherein $R^2$ and $R^9$ are attached to the same carbon atom. In a first subembodiment of embodiment 21, $R^2$ and $R^9$ are attached to the ring carbon atom that is meta to the ring carbon attached to $R^1$.

22A. In embodiment 22A, the compound of any one of embodiments 1A, 2A, 2Aa, 3A, 3Aa, 7A, 8 to 10, 12A and 13 to 18 and subembodiments contained therein or a pharmaceutically acceptable salt thereof, is wherein $R^2$ and $R^9$ are attached to the ring carbon atom that is meta to the ring carbon attached to $R^1$ and wherein $R^2$ is hydrogen or deuterium and $R^9$ is hydrogen, methyl, or fluoro.

22B. In embodiment 22B, the compound of embodiment 22A and subembodiments contained therein or a pharmaceutically acceptable salt thereof, is wherein $R^2$ is hydrogen or deuterium and $R^9$ is fluoro.

22C. In embodiment 22C, the compound of embodiment 22A and 22B and subembodiments contained therein or a pharmaceutically acceptable salt thereof, is wherein $R^{2a}$ and $R^{9a}$ are independently hydrogen, deuterium, or fluoro, preferably hydrogen or fluoro, more preferably hydrogen.

22. In embodiment 22, the compound of any one of embodiments 1A to 18 and 22C and subembodiments contained therein or a pharmaceutically acceptable salt thereof, is wherein $R^2$ and $R^9$ are attached to the same carbon atom and together with the carbon atom to which they are attached form $>C(=O)$. In a first subembodiment of embodiment 22, $R^2$ and $R^9$ are attached to the ring carbon atom that is meta to the ring carbon attached to $R^1$.

23. In embodiment 23, the compound of any one of embodiments 1A to 18 and 22C and subembodiments contained therein or a pharmaceutically acceptable salt thereof, is wherein $R^2$ and $R^9$ are attached to the same carbon atom and together with the carbon atom to which they are attached form 3 to 6 membered cycloalkylene. In a first subembodiment of embodiment 23, $R^2$ and $R^9$ are attached to the same carbon atom and together with the carbon atom to which they are attached form cyclopropene. In a first subembodiment of embodiment 23, $R^2$ and $R^9$ are attached to the ring carbon atom that is meta to the ring carbon attached to $R^1$.

24. In embodiment 24, the compound of any one of embodiments 1A to 18 and 22C and subembodiments contained therein or a pharmaceutically acceptable salt thereof, is wherein $R^2$ and $R^9$ are attached to the same carbon atom and together with the carbon atom to which they are attached form 4 to six membered heterocyclylene. In a first subembodiment of embodiment 23, $R^2$ and $R^9$ are attached to the same carbon atom and together with the carbon atom to which they are attached form oxetan-4-yl. In a first subembodiment of embodiment 24, $R^2$ and $R^9$ are attached to the ring carbon atom that is meta to the ring carbon attached to $R^1$.

25. In embodiment 25, the compound of any one of embodiments 1A to 18 and subembodiments contained therein or a pharmaceutically acceptable salt thereof, is wherein $R^2$ and $R^9$ are attached to the same carbon atom and together with the carbon atom to which they are attached form alkyldienyl, preferably vinydienyl. In a first subembodiment of embodiment 22, $R^2$ and $R^9$ are attached to the ring carbon atom that is meta to the ring carbon attached to $R^1$.

26. In embodiment 26, the compound of any one of embodiments 1A, 2A, 2Aa, 12A, 13 to 20 and subembodiments contained therein or a pharmaceutically acceptable salt thereof is a compound of formula (VIIIa1) or (VIIIb1):

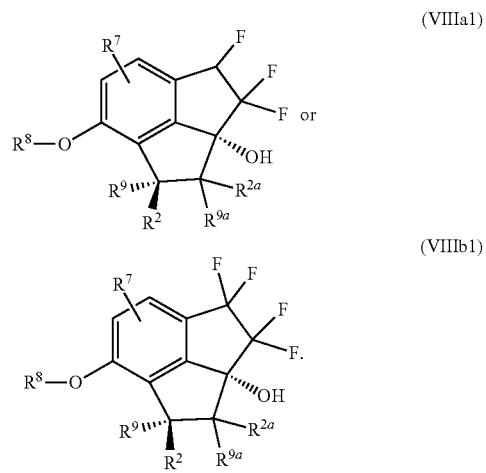

In one embodiment the compound has formula (VIIIb1).

27. In embodiment 27, the compound of embodiment 26 and subembodiment contained therein or a pharmaceutically acceptable salt thereof is wherein $R^2$ is hydrogen or deuterium and $R^9$ is hydrogen, fluoro, or methyl, preferably fluoro, and $R^{2a}$ and $R^{9a}$ are independently hydrogen, deuterium, or fluoro. In a first subembodiment of embodiment 26, $R^{2a}$ and $R^{9a}$ are independently hydrogen or deuterium. In a second subembodiment of embodiment 26, $R^{2a}$ and $R^{9a}$ are independently hydrogen or fluoro.

28. In embodiment 28, the compound of any one of embodiments 1, 2, 2a, and 12 to 20 and subembodiments contained therein or a pharmaceutically acceptable salt thereof is a compound of formula (VIIIa) or (VIIIb):

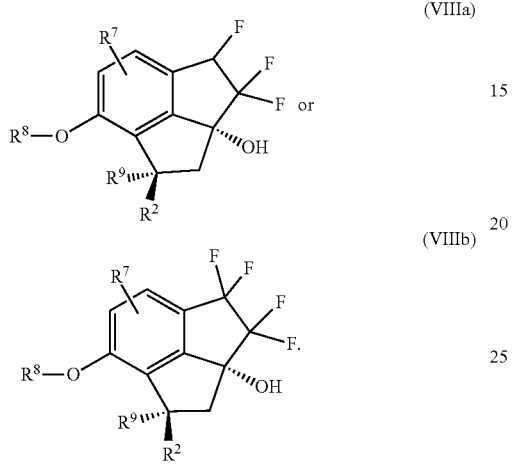

In one embodiment the compound has formula (VIIIb).

29. In embodiment 29, the compound of embodiment 28 and subembodiment contained therein or a pharmaceutically acceptable salt thereof is wherein $R^2$ is hydrogen and $R^9$ is hydrogen, fluoro, or methyl.

30. In embodiment 30, the compound of any one of embodiments 26 to 29 and subembodiment contained therein or a pharmaceutically acceptable salt thereof is wherein $R^7$ is hydrogen and $R^8$ is 3-cyano-5-fluorophenyl or 3-cyano-5-fluoro-2,4,6-trideuteriophenyl.

It is understood that the embodiments and subembodiments set forth above include all combination of embodiments and subembodiments listed therein. For example, $R^9$ listed in seventh sub-embodiment of embodiment 20, can independently be combined with one or more of the embodiments 1A-30 and/or subembodiments contained therein.

In further embodiment 40 to 99, the present disclosure includes:

40. A compound of Formula (IA):

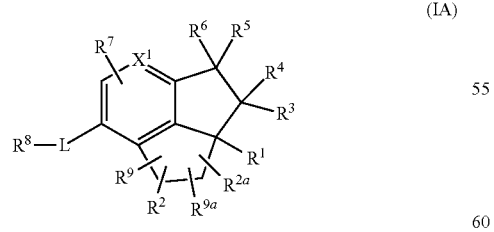

wherein:

$X^1$ is CH or N;

$R^1$ is hydroxy, halo, amino, —OP(O)(OH)$_2$, —OCH$_2$OP(O)(OH)$_2$, —OCOR$^{10}$, —OCOOR$^{11}$, —OCONR$^{12}$R$^{13}$, —OCHR$^{14}$OCOR$^{15}$ or —OCHR$^{14}$OCOOR$^{15a}$ where $R^{10}$, $R^{11}$, and $R^{15}$ and $R^{15a}$ are independently alkyl or alkyl substituted with amino, carboxy or hydroxy, $R^{12}$ and $R^{13}$ are independently hydrogen, alkyl, or alkyl substituted with amino, carboxy or hydroxy or $R^{12}$ and $R^{13}$ together with the nitrogen atom to which they are attached form optionally substituted heterocyclyl, and each $R^{14}$ is hydrogen, alkyl, or haloalkyl;

$R^2$ is hydrogen, deuterium, alkyl, halo, haloalkyl, alkenyl, or alkynyl;

$R^{2a}$ is hydrogen or deuterium;

$R^3$ and $R^4$ are independently hydrogen, deuterium, alkyl, cycloalkyl, halo, haloalkyl, hydroxyalkyl, or alkoxyalkyl; or $R^3$ and $R^4$ together with the carbon to which they are attached form >C(=O), 3 to 6 membered cycloalkylene, or 4 to 6 membered optionally substituted heterocyclylene;

$R^5$ is hydrogen, deuterium, alkyl, halo, haloalkyl, hydroxy, or alkoxy;

$R^6$ is hydrogen, deuterium, alkyl, cycloalkyl, or halo; or $R^5$ and $R^6$ together with the carbon to which they are attached form >C(=O), alkyldienyl, 3 to 6 membered cycloalkylene, or 4 to 6 membered optionally substituted heterocyclylene; provided $R^5$ and $R^6$ and $R^3$ and $R^4$ together with the carbon to which they are attached do not form >C(=O), cycloalkylene or optionally substituted 4 to 6 membered heterocyclylene simultaneously;

$R^7$ is hydrogen, deuterium, alkyl, alkoxy, cyano, halo, haloalkyl, or haloalkoxy;

L is a bond, S, SO, SO$_2$, O, CO, or NR$^{16}$ where $R^{16}$ is hydrogen or alkyl;

$R^8$ is alkyl, haloalkyl, hydroxyalkyl, alkoxyalkyl, aminoalkyl, cycloalkyl, cycloalkenyl, bicyclic cycloalkyl, oxocycloalkenyl, cycloalkylalkyl, aryl, aralkyl, heterocyclyl, spirocycloalkyl, spiroheterocyclyl, heterocyclylalkyl, heteroaryl, or heteroaralkyl wherein aryl or heteroaryl, each by itself or as part of aralkyl or heteroaralkyl, or heterocyclyl by itself or as part of heterocyclylalkyl is substituted with $R^a$, $R^b$, $R^c$, $R^g$ and/or $R^h$ wherein $R^a$, $R^b$, and $R^c$ are independently selected from hydrogen, deuterium, alkyl, haloalkyl, haloalkyloxy, alkoxy, hydroxy, halo, cyano, hydroxyalkyl, alkoxyalkyl, aminoalkyl, alkenyl, alkynyl, alkylidenyl, optionally substituted aryl, optionally substituted heteroaryl, and optionally substituted heterocyclyl and $R^g$ and $R^h$ are independently selected from hydrogen, deuterium, and halo; and $R^9$ is hydrogen, alkyl, cycloalkyl, hydroxy, alkoxy, cyano, halo, haloalkyl, haloalkoxy, alkylsulfoxide, alkylsulfonyl, or heteroaryl wherein the heteroaryl is optionally substituted with $R^d$, $R^e$, and $R^f$ independently selected from hydrogen, alkyl, haloalkyl, haloalkoxy, alkoxy, hydroxy, halo, and cyano; or when $R^9$ and $R^2$ are attached to the same carbon atom, $R^9$ and $R^2$ can combine to form oxo, alkyldienyl, 3 to 6 membered cycloalkylene, or 4 to 6-membered heterocyclylene;

$R^{9a}$ is hydrogen or deuterium;

a pharmaceutically acceptable salt thereof.

41. A compound of Formula (I):

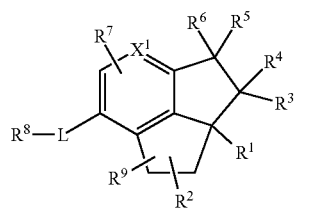

(I)

wherein:
- $X^1$ is CH or N;
- $R^1$ is hydroxy, halo, amino, —OP(O)(OH)$_2$, —OCH$_2$OP(O)(OH)$_2$, —OCOR$^{10}$, —OCOOR$^{11}$, —OCONR$^{12}$R$^{13}$, —OCHR$^{14}$OCOR$^{15}$ or —OCHR$^{14}$OCOOR$^{15a}$ where $R^{10}$, $R^{11}$, $R^{15}$, and $R^{15a}$ are independently alkyl or alkyl substituted with amino, carboxy or hydroxy, $R^{12}$ and $R^{13}$ are independently hydrogen, alkyl, or alkyl substituted with amino, carboxy or hydroxy or $R^{12}$ and $R^{13}$ together with the nitrogen atom to which they are attached form optionally substituted heterocyclyl, and each $R^{14}$ is hydrogen, alkyl, or haloalkyl;
- $R^2$ is hydrogen, deuterium, alkyl, haloalkyl, alkynyl, or alkenyl;
- $R^3$ and $R^4$ are independently hydrogen, deuterium, alkyl, cycloalkyl, halo, haloalkyl, hydroxyalkyl, or alkoxyalkyl; or
- $R^3$ and $R^4$ together with the carbon to which they are attached form >C(=O), 3 to 6 membered cycloalkylene, or 4 to 6 membered optionally substituted heterocyclylene;
- $R^5$ is hydrogen, deuterium, alkyl, halo, haloalkyl, hydroxy, or alkoxy;
- $R^6$ is hydrogen, deuterium, alkyl, cycloalkyl, or halo; or
- $R^5$ and $R^6$ together with the carbon to which they are attached form 3 to 6 membered cycloalkylene or 4 to 6 membered optionally substituted heterocyclylene; provided $R^5$ and $R^6$ and
- $R^3$ and $R^4$ together with the carbon to which they are attached do not form cycloalkylene or optionally substituted 4 to 6 membered heterocyclylene simultaneously;
- $R^7$ is hydrogen, deuterium, alkyl, alkoxy, cyano, halo, haloalkyl, or haloalkoxy;
- L is a bond, S, SO, SO$_2$, O, CO, or NR$^{16}$ where $R^{16}$ is hydrogen or alkyl;
- $R^8$ is alkyl, haloalkyl, hydroxyalkyl, alkoxyalkyl, aminoalkyl, cycloalkyl, cycloalkenyl, bicyclic cycloalkyl, oxocycloalkenyl, cycloalkylalkyl, aryl, aralkyl, heterocyclyl, spirocycloalkyl, spiroheterocyclyl, heterocyclylalkyl, heteroaryl, or heteroaralkyl wherein aryl or heteroaryl, each by itself or as part of aralkyl or heteroaralkyl, or heterocyclyl by itself or as part of heterocyclylalkyl is substituted with $R^a$, $R^b$, and/or $R^c$ independently selected from hydrogen, alkyl, haloalkyl, haloalkyloxy, alkoxy, hydroxy, halo, cyano, hydroxyalkyl, alkoxyalkyl, aminoalkyl, alkenyl, alkynyl, alkylidenyl, optionally substituted aryl, optionally substituted heteroaryl, and optionally substituted heterocyclyl; and
- $R^9$ is hydrogen, alkyl, cycloalkyl, hydroxy, alkoxy, cyano, halo, haloalkyl, haloalkoxy, alkylsulfoxide, or alkylsulfonyl, or heteroaryl wherein the heteroaryl is optionally substituted with $R^d$, $R^e$, and $R^f$ independently selected from hydrogen, alkyl, haloalkyl, haloalkoxy, alkoxy, hydroxy, halo, and cyano; or
- when $R^9$ and $R^2$ are attached to the same carbon atom, $R^9$ and $R^2$ can combine to form oxo, alkyldienyl, 3 to 6 membered cycloalkylene, or 4 to 6-membered heterocyclylene;

a pharmaceutically acceptable salt thereof.

42. The compound of embodiment 40 or 41, or a pharmaceutically acceptable salt thereof, wherein $R^3$ and $R^4$ are independently halo.

43. The compound of embodiment 40 or 41, or a pharmaceutically acceptable salt thereof, wherein $R^3$ is halo and $R^4$ is hydrogen.

44. The compound of embodiment 40, 41, 42, or 43, or a pharmaceutically acceptable salt thereof, wherein $R^1$ is hydroxy.

45. The compound of embodiment 40, 41, 42, or 43, or a pharmaceutically acceptable salt thereof, wherein $R^1$ is amino.

46. The compound of any one of embodiments 40 to 45, or a pharmaceutically acceptable salt thereof, wherein $R^6$ is halo.

47. The compound of any one of embodiments 40 to 45, or a pharmaceutically acceptable salt thereof, wherein $R^6$ is alkyl, preferably $R^6$ is methyl.

48. The compound of any one of embodiments 40 to 45, or a pharmaceutically acceptable salt thereof, wherein $R^6$ is hydrogen.

49. The compound of any one of embodiments 40 to 45, or a pharmaceutically acceptable salt thereof, wherein $R^6$ is cycloalkyl, preferably cyclopropyl, cyclobutyl, cyclopentyl or cyclohexyl.

50. The compound of any one of embodiments 40 to 49, or a pharmaceutically acceptable salt thereof, wherein $R^5$ is halo, preferably fluoro.

51. The compound of any one of embodiments 40 to 49, or a pharmaceutically acceptable salt thereof, wherein $R^5$ is haloalkyl, preferably $R^5$ is difluoromethyl or trifluoromethyl.

52. The compound of any one of embodiments 40 to 49, or a pharmaceutically acceptable salt thereof, wherein $R^5$ is alkyl, preferably $R^5$ is methyl or ethyl.

53. The compound of any one of embodiments 40 to 49, or a pharmaceutically acceptable salt thereof, wherein $R^5$ is hydrogen or alkoxy.

54. The compound of any one of embodiments 40 to 45, or a pharmaceutically acceptable salt thereof, wherein $R^5$ and $R^6$ together with the carbon to which they are attached form 3 to 6 membered cycloalkylene, preferably cyclopropylene, cyclobutylene or cyclopentylene optionally substituted with one or two fluoro.

55. The compound of any one of embodiments 40 to 54, or a pharmaceutically acceptable salt thereof, wherein $X^1$ is CR$^7$.

56. The compound of embodiment 40 or a pharmaceutically pharmaceutically acceptable salt thereof, having the structure of formula (IIa1) or (IIb1):

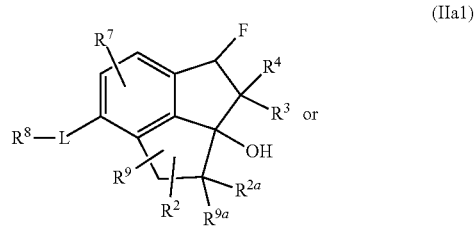

(IIa1)

or

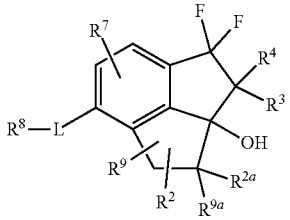

(IIb1)

57. The compound of embodiment 40 or a pharmaceutically acceptable salt thereof, having the structure of formula (IIa1') or (IIb1'):

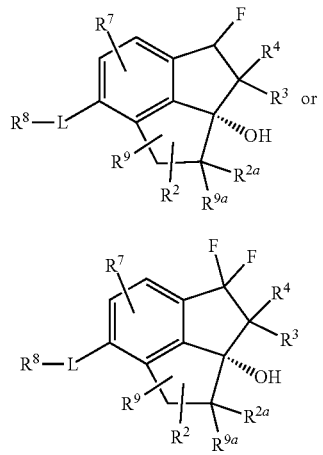

(Ia1')

(IIb1')

58. The compound of embodiment 41, or a pharmaceutically acceptable salt thereof, having the structure of formula (IIa) or (IIb):

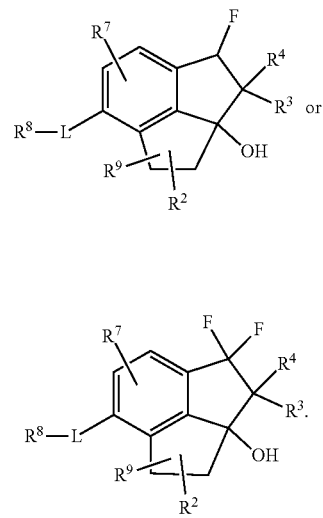

(IIa)

(IIb)

59. The compound of embodiment 41, or a pharmaceutically acceptable salt thereof, having the structure of formula (IIa') or (IIb'):

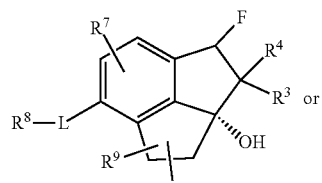

(IIa')

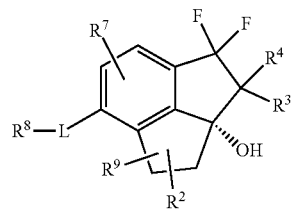

(IIb')

60. The compound of embodiment 41, or a pharmaceutically acceptable salt thereof, having the structure of formula (IVa):

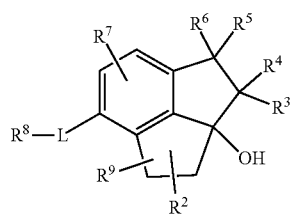

(IVa)

where $R^5$ and $R^6$ together with the carbon to which they are attached form 3 to 6 membered cycloalkylene, preferably cyclopropylene, cyclobutylene or cyclopentylene optionally substituted with one or two fluoro.

61. The compound of embodiment 41, or a pharmaceutically acceptable salt thereof, having the structure of formula (VIa) or (VIb):

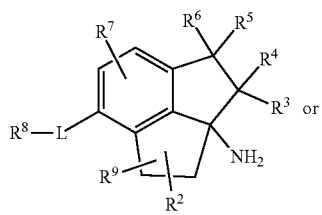

(VIa)

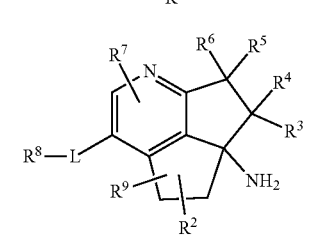

(VIb)

where $R^5$ and $R^6$ together with the carbon to which they are attached form 3 to 6 membered cycloalkylene, preferably cyclopropylene, cyclobutylene or cyclopentylene optionally substituted with one or two fluoro.

62. The compound of embodiment 41, or a pharmaceutically acceptable salt thereof, having the structure of formula (VIIa) or (VIIb):

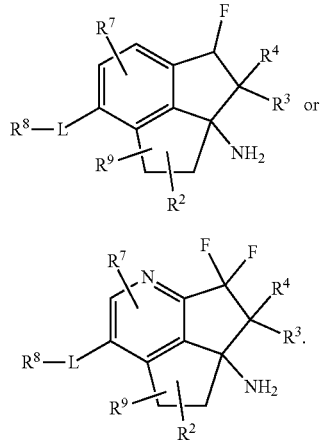

(VIIa)

(VIIb)

63. The compound of any one of embodiments 40 to 62, or a pharmaceutically acceptable salt thereof, wherein $R^3$ is fluoro.
64. The compound of any one of embodiments 40-42 and 44 to 62, or a pharmaceutically acceptable salt thereof, where $R^3$ and $R^4$ are fluoro.
65. The compound of any one of embodiments 40 to 64, or a pharmaceutically acceptable salt thereof, wherein L is O, S, SO, $SO_2$, or NH.
66. The compound of embodiment 65, or a pharmaceutically acceptable salt thereof, wherein L is O.
67. The compound of any one of embodiments 40 to 66, or a pharmaceutically acceptable salt thereof, wherein $R^8$ is cycloalkyl, cycloalkenyl, bicyclic cycloalkyl, oxocycloalkenyl, cycloalkylalkyl, aryl, aralkyl, heterocyclyl, spirocycloalkyl, spiroheterocyclyl, heterocyclylalkyl, heteroaryl, or heteroaralkyl wherein aryl or heteroaryl, each by itself or as part of aralkyl or heteroaralkyl, or heterocyclyl by itself or as part of heterocyclylalkyl is substituted with $R^a$, $R^b$, and $R^c$ independently selected from hydrogen, alkyl, haloalkyl, haloalkyloxy, alkoxy, hydroxy, halo, cyano, hydroxyalkyl, alkoxyalkyl, aminoalkyl, alkenyl, alkynyl, alkylidenyl, optionally substituted aryl, optionally substituted heteroaryl, and optionally substituted heterocyclyl.
68. The compound of any one of embodiments 40, 42 to 57, and 63 to 66 and subembodiments contained therein, or a pharmaceutically acceptable salt thereof, is wherein $R^8$ is phenyl substituted with $R^a$, $R^b$, $R^c$, $R^g$ and $R^h$ wherein $R^a$, $R^b$, and $R^c$ are independently selected from hydrogen, deuterium, alkyl, haloalkyl, haloalkyloxy, alkoxy, hydroxy, halo, cyano, hydroxyalkyl, alkoxyalkyl, aminoalkyl, optionally substituted aryl, optionally substituted heteroaryl, and optionally substituted heterocyclyl and $R^g$ and $R^h$ are independently selected from hydrogen, and halo.
68A. The compound of any one of embodiments 40, 42 to 57, and 63 to 66 and subembodiments contained therein, or a pharmaceutically acceptable salt thereof, is wherein $R^8$ is 3-chloro-5-fluorophenyl, 3,5-difluorophenyl, 3-fluoro-5-methoxyphenyl, 3-cyano-5-fluorophenyl, 3-chloro-5-cyanophenyl, 3-cyano-5-methylphenyl, 3-chloro-4-fluorophenyl, 3-chloro-5-fluorophenyl, 3-fluoro-5-methylphenyl, 3-cyanophenyl, 3-trifluoromethylphenyl, 3,4-dichlorophenyl, 3-chloro-2-methylphenyl, 3,5-dichlorophenyl, 3,5-dimethylphenyl, 2-chloro-6-methylphenyl, 2,6-difluorophenyl, 3,4,5-trifluorophenyl, 3,4-difluorophenyl, 4-fluoro-3-methylphenyl, 3-cyano-4-fluorophenyl, 3-cyano-5-difluoromethylphenyl or 3-cyano-5-fluoro-2,4,6-trideuteriophenyl. In a first subembodiment of embodiment 68A, $R^8$ is 3-cyano-5-fluorophenyl or 3-cyano-5-fluoro-2,4,6-trideuteriophenyl
69. The compound of any one of embodiments 41 to 55 and 58 to 66, or a pharmaceutically acceptable salt, thereof, wherein $R^8$ is phenyl substituted with $R^a$, $R^b$, and $R^c$ independently selected from hydrogen, alkyl, haloalkyl, haloalkyloxy, alkoxy, hydroxy, halo, cyano, hydroxyalkyl, alkoxyalkyl, aminoalkyl, optionally substituted aryl, optionally substituted heteroaryl, and optionally substituted heterocyclyl.
70. The compound of any one of embodiments 41 to 55 and 58 to 66, or a pharmaceutically acceptable salt thereof, wherein $R^8$ is 3-chloro-5-fluorophenyl, 3,5-difluorophenyl, 3-fluoro-5-methoxyphenyl, 3-cyano-5-fluorophenyl, 3-chloro-5-cyanophenyl, 3-cyano-5-methylphenyl, 3-chloro-4-fluorophenyl, 3-chloro-5-fluorophenyl, 3-fluoro-5-methylphenyl, 3-cyanophenyl, 3-trifluoromethylphenyl, 3,4-dichlorophenyl, 3-chloro-2-methylphenyl, 3,5-dichlorophenyl, 3,5-dimethylphenyl, 2-chloro-6-methylphenyl, 2,6-difluorophenyl, 3,4,5-trifluorophenyl, 3,4-difluorophenyl, 4-fluoro-3-methylphenyl, 3-cyano-4-fluorophenyl, or 3-cyano-5-difluoromethylphenyl. In a fourth subembodiment of embodiment 26, $R^8$ is 3-cyano-5-fluorophenyl.
71. The compound of any one of embodiments 40 to 66 and any subembodiments contained therein, or a pharmaceutically acceptable salt thereof, wherein $R^8$ is cycloalkyl or cycloalkylalkyl each optionally substituted with one or two substituents independently selected from alkyl, halo, alkoxy, cyano, and hydroxy.
72. The compound of any one of embodiments 40 to 66 and any subembodiments contained therein, or a pharmaceutically acceptable salt thereof, wherein $R^8$ is heteroaryl substituted with $R^a$, $R^b$, and $R^c$ independently selected from hydrogen, alkyl, haloalkyl, haloalkyloxy, alkoxy, hydroxy, halo, cyano, hydroxyalkyl, alkoxyalkyl, aminoalkyl, optionally substituted aryl, optionally substituted heteroaryl, and optionally substituted heterocyclyl.
73. The compound of any one of embodiments 40 to 66, or a pharmaceutically acceptable salt, thereof, wherein $R^8$ is 5- or 6-membered heteroaryl (e.g., pyridyl, pyridazinyl, pyrimidinyl, thienyl, furanyl, thiazolyl, oxazolyl, imidazolyl, or pyrazinyl), each substituted with $R^a$, $R^b$, and $R^o$ wherein $R^a$ and $R^b$ are independently selected from alkyl, alkoxy, hydroxy, halo, haloalkyl, haloalkoxy, and cyano and $R^o$ is selected from hydrogen, alkyl, halo, haloalkyl, and haloalkoxy.
74. The compound of any one of embodiments 40 to 66, or a pharmaceutically acceptable salt, thereof, wherein $R^8$ is pyridin-3-yl, pyridin-2-yl, pyridazin-3-yl, pyridazin-4-yl, pyrimidin-5-yl, pyrimidin-2-yl, thien-2-yl, furan-2-yl, thiazol-5-yl, oxazol-5-yl, imidazol-5-yl, furan-3-yl thien-3-yl, thiazol-4-yl, pyridin-4-yl, oxazol-2-yl, imidazol-2-yl, pyridin-2-yl, pyrazin-2-yl, or thiazol-2-yl, and is substituted with $R^a$, $R^b$, and $R^c$ wherein $R^a$ and $R^b$ are independently selected from hydrogen, methyl, methoxy, hydroxy, chloro, fluoro, difluoromethyl, trifluoromethyl, difluoromethoxy, and trifluoromethoxy and $R^e$ is selected from hydrogen, methyl, cyano, chloro, fluoro, difluoromethyl, trifluoromethyl, difluoromethoxy, and trifluoromethoxy.

75. The compound of embodiment 74, or a pharmaceutically acceptable salt thereof, wherein $R^8$ is 5-cyano-pyridin-3-yl, 5-chloropyridin-3-yl, or 5-fluoropyridin-3-yl.

76. The compound of any one of embodiments 40 to 75, or a pharmaceutically acceptable salt thereof, wherein $R^7$ is hydrogen, methyl, ethyl, methoxy, fluoro, trifluoromethyl, or trifluoromethoxy, preferably $R^7$ is hydrogen.

77. The compound of any one of embodiments 40 to 76, or a pharmaceutically acceptable salt thereof, wherein $R^2$ is hydrogen, fluoro, methyl or ethyl.

78. The compound of any one of embodiments 40 to 77, or a pharmaceutically acceptable salt thereof, wherein $R^9$ is hydrogen, alkyl, halo, hydroxy, or alkoxy.

79. The compound of any one of embodiments 40 to 77, or a pharmaceutically acceptable salt thereof, wherein $R^9$ is hydrogen, methyl, methoxy, or fluoro.

80. The compound of any one of embodiments 40 to 79, or a pharmaceutically acceptable salt thereof, wherein $R^2$ and $R^9$ are attached to the same carbon atom.

81. The compound of embodiment 80, or a pharmaceutically acceptable salt thereof, wherein $R^2$ and $R^9$ are attached to the ring carbon atom that is meta to the ring carbon attached to $R^1$.

82. The compound of any one of embodiments 40 to 76, or a pharmaceutically acceptable salt thereof, wherein $R^2$ and $R^9$ are attached to the same carbon atom and together with the carbon atom to which they are attached form >C(=O).

83. The compound of any one of embodiments 40 to 76, or a pharmaceutically acceptable salt thereof, wherein $R^2$ and $R^9$ are attached to the same carbon atom and together with the carbon atom to which they are attached form 3 to 6 membered cycloalkylene.

84. The compound of embodiment 83, or a pharmaceutically acceptable salt thereof, wherein $R^2$ and $R^9$ together with the carbon atom to which they are attached form cyclopropene.

85. The compound of any one of embodiments 40 to 76, or a pharmaceutically acceptable salt thereof, wherein $R^2$ and $R^9$ are attached to the same carbon atom and together with the carbon atom to which they are attached form 4 to six membered heterocyclylene.

85a. The compound of any one of embodiments 40 to 76, or a pharmaceutically acceptable salt thereof, wherein $R^2$ and $R^9$ are attached to the same carbon atom and together with the carbon atom to which they are attached form alkyldienyl, preferably vinyldienyl.

86. The compound of any one of embodiments 82 to 85a, or a pharmaceutically acceptable salt thereof, wherein $R^2$ and $R^9$ are attached to the ring carbon atom that is meta to the ring carbon attached to $R^1$.

87. The compound of any one of embodiments 40, 42 to 57, 63 to 68A and 71 to 76, or a pharmaceutically acceptable salt thereof, wherein $R^2$ and $R^9$ are attached to the ring carbon atom that is meta to the ring carbon attached to $R^1$ and wherein $R^2$ is hydrogen or deuterium and $R^9$ is hydrogen, methyl, or fluoro.

88. The compound of embodiment 87 and subembodiments contained therein or a pharmaceutically acceptable salt thereof, is wherein $R^2$ is hydrogen or deuterium and $R^9$ is fluoro.

89. The compound of any one of embodiments 40, 65 to 68A, and 71 to 79 or a pharmaceutically acceptable salt thereof having the structure of formula (VIIIa1) or (VIIIb1):

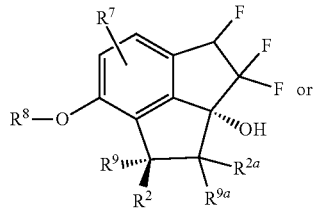

(VIIIa1)

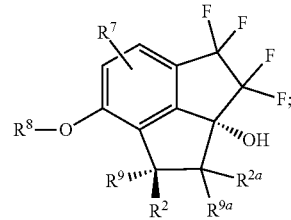

(VIIIb1)

preferably the structure of formula (VIIIb1).

90. The compound of embodiment 89, or a pharmaceutically acceptable salt thereof, wherein $R^{2a}$ and $R^{9a}$ are independently hydrogen or deuterium, preferably $R^{2a}$ and $R^{9a}$ are hydrogen.

91. The compound of any one of embodiments 41, 65 to 67, and 69 to 79, or a pharmaceutically acceptable salt thereof, having the structure of formula (VIIIa) or (VIIIb):

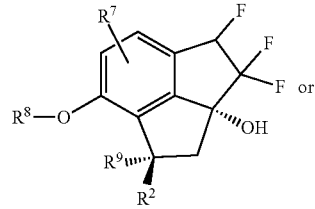

(VIIIa)

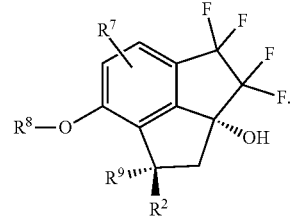

(VIIIb)

preferably the structure of formula (VIIIb).

92. The compound of embodiment 91, or a pharmaceutically acceptable salt thereof, wherein $R^2$ is hydrogen and $R^9$ is hydrogen, fluoro, or methyl.

93. A pharmaceutical composition comprising a compound of any one of embodiments 40-92, or a pharmaceutically acceptable salt thereof; and a pharmaceutically acceptable excipient.

94. A method of inhibiting HIF2α which method comprises contacting HIF2α with a compound of any one of embodiments 40-92, or a pharmaceutically acceptable salt thereof, or with a pharmaceutical composition of embodiment 93.
95. A method of treating a disease mediate by HIF2α in a patient which method comprises administering to the patient in recognized need thereof, a therapeutically effective amount of a pharmaceutical composition comprising a compound of any one of embodiments 40-92, or a pharmaceutically acceptable salt thereof; and a pharmaceutically acceptable excipient.
96. A method of treating cancer in a patient which method comprises administering to the patient in recognized need thereof, a therapeutically effective amount of a pharmaceutical composition comprising a compound of any one of embodiments 40-92, or a pharmaceutically acceptable salt thereof, and a pharmaceutically acceptable excipient.
97. The method of embodiment 96, wherein the compound of embodiment 40-92 or a pharmaceutically acceptable salt thereof, can be optionally administered in combination with at least one other anticancer agent.
98. The method of embodiment 96 or 97, wherein the cancer is renal cancer or glioblastoma.
99. The method of embodiment 95, wherein the disease is NASH, pulmonary artery hypertension, or inflammatory bowel disease.

Representative compounds of the disclosure made are disclosed in Compound Table I below:

TABLE I

| Compound # | Structure | Name |
|---|---|---|
| 1 | 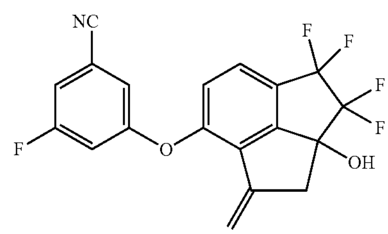 [SMILES: C=C1CC2(O)c3c(ccc(Oc4cc(F)cc(C#N)c4)c31)C(F)(F)C2(F)F] | 3-fluoro-5-((3,3,4,4-tetrafluoro-2a-hydroxy-1-methylene-2,2a,3,4-tetrahydro-1H-cyclopenta[cd]inden-7-yl)oxy)benzonitrile |
| 2 | 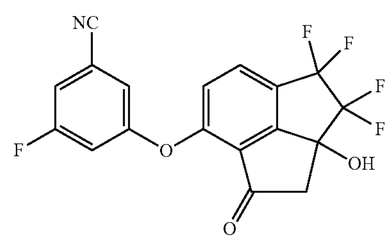 [SMILES: N#Cc1cc(F)cc(Oc2ccc3c4c2C(=O)CC4(O)C(F)(F)C3(F)F)c1] | 3-fluoro-5-((3,3,4,4-tetrafluoro-2a-hydroxy-1-oxo-2,2a,3,4-tetrahydro-1H-cyclopenta[cd]inden-7-yl)oxy)benzonitrile |
| 3 | 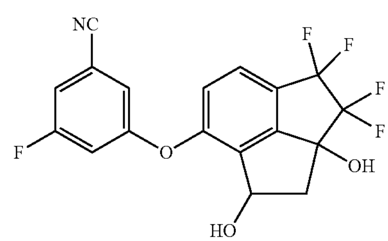 [SMILES: N#Cc1cc(F)cc(Oc2ccc3c4c2C(O)CC4(O)C(F)(F)C3(F)F)c1] | 3-fluoro-5-((3,3,4,4-tetrafluoro-1,2a-dihydroxy-2,2a,3,4-tetrahydro-1H-cyclopenta[cd]inden-7-yl)oxy)benzonitrile |
| 4 | 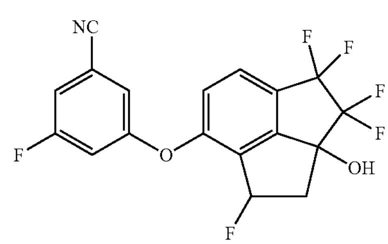 [SMILES: N#Cc1cc(F)cc(Oc2ccc3c4c2C(F)CC4(O)C(F)(F)C3(F)F)c1] | 3-fluoro-5-((1,3,3,4,4-pentafluoro-2a-hydroxy-2,2a,3,4-tetrahydro-1H-cyclopenta[cd]inden-7-yl)oxy)benzonitrile |

TABLE I-continued

| Compound # | Structure | Name |
|---|---|---|
| 5 | 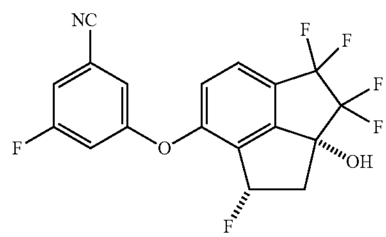 [SMILES: N#Cc1cc(F)cc(Oc2ccc3c4c2[C@@H](F)C[C@]4(O)C(F)(F)C3(F)F)c1] | 3-fluoro-5-(((1S,2aR)-1,3,3,4,4-pentafluoro-2a-hydroxy-2,2a,3,4-tetrahydro-1H-cyclopenta[cd]inden-7-yl)oxy)benzonitrile |
| 6 | 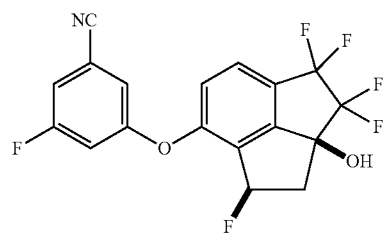 [SMILES: N#Cc1cc(F)cc(Oc2ccc3c4c2[C@H](F)C[C@@]4(O)C(F)(F)C3(F)F)c1] | 3-fluoro-5-(((1R,2aS)-1,3,3,4,4-pentafluoro-2a-hydroxy-2,2a,3,4-tetrahydro-1H-cyclopenta[cd]inden-7-yl)oxy)benzonitrile |
| 7 | 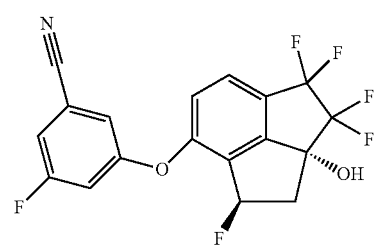 [SMILES: N#Cc1cc(F)cc(Oc2ccc3c4c2[C@H](F)C[C@]4(O)C(F)(F)C3(F)F)c1] | 3-fluoro-5-(((1R,2aR)-1,3,3,4,4-pentafluoro-2a-hydroxy-2,2a,3,4-tetrahydro-1H-cyclopenta[cd]inden-7-yl)oxy)benzonitrile |
| 8 | 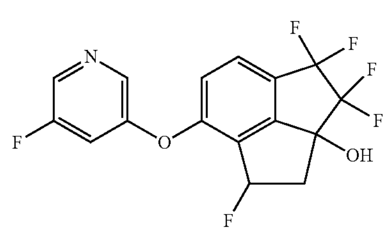 [SMILES: OC12CC(F)c3c(Oc4cncc(F)c4)ccc(c31)C(F)(F)C2(F)F] | 1,3,3,4,4-pentafluoro-7-((5-fluoropyridin-3-yl)oxy)-1,2,3,4-tetrahydro-2aH-cyclopenta[cd]inden-2a-ol |
| 9 | 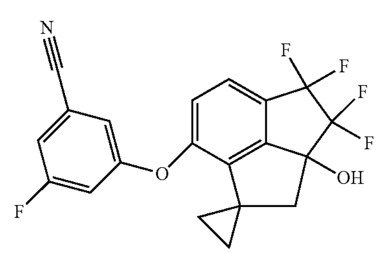 [SMILES: N#Cc1cc(F)cc(Oc2ccc3c4c2C2(CC2)CC4(O)C(F)(F)C3(F)F)c1] | 3-fluoro-5-((3,3,4,4-tetrafluoro-2a-hydroxy-2,2a,3,4-tetrahydrospiro[cyclopenta[cd]indene-1,1'-cyclopropan]-7-yl)oxy)benzonitrile |
| 10 | 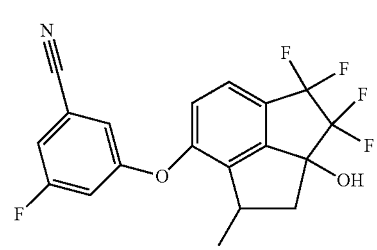 [SMILES: CC1CC2(O)c3c(ccc(Oc4cc(F)cc(C#N)c4)c31)C(F)(F)C2(F)F] | 3-fluoro-5-((3,3,4,4-tetrafluoro-2a-hydroxy-1-methyl-2,2a,3,4-tetrahydro-1H-cyclopenta[cd]inden-7-yl)oxy)benzonitrile |

TABLE I-continued

| Compound # | Structure | Name |
|---|---|---|
| 11 | 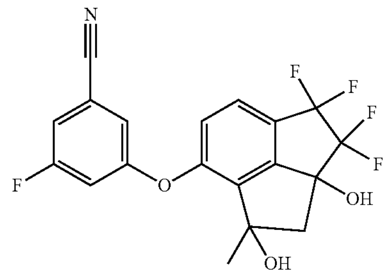 [SMILES: CC1(O)CC2(O)c3c(ccc(Oc4cc(F)cc(C#N)c4)c31)C(F)(F)C2(F)F] | 3-fluoro-5-((3,3,4,4-tetrafluoro-1,2a-dihydroxy-1-methyl-2,2a,3,4-tetrahydro-1H-cyclopenta[cd]inden-7-yl)oxy)benzonitrile |
| 12 | 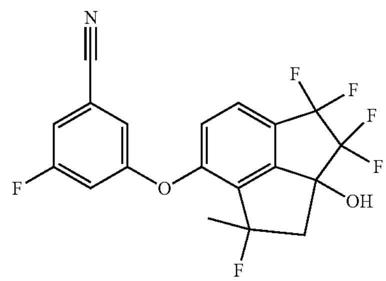 [SMILES: CC1(F)CC2(O)c3c(ccc(Oc4cc(F)cc(C#N)c4)c31)C(F)(F)C2(F)F] | 3-fluoro-5-((1,3,3,4,4-pentafluoro-2a-hydroxy-1-methyl-2,2a,3,4-tetrahydro-1H-cyclopenta[cd]inden-7-yl)oxy)benzonitrile |
| 13 | 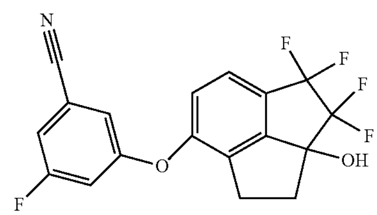 [SMILES: N#Cc1cc(F)cc(Oc2ccc3c4c2CCC4(O)C(F)(F)C3(F)F)c1] | 3-fluoro-5-((3,3,4,4-tetrafluoro-2a-hydroxy-2,2a,3,4-tetrahydro-1H-cyclopenta[cd]inden-7-yl)oxy)benzonitrile |
| 14 | 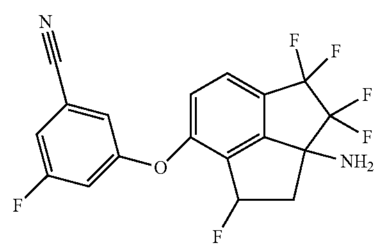 [SMILES: N#Cc1cc(F)cc(Oc2ccc3c4c2C(F)CC4(N)C(F)(F)C3(F)F)c1] | 3-((2a-amino-1,3,3,4,4-pentafluoro-2,2a,3,4-tetrahydro-1H-cyclopenta[cd]inden-7-yl)oxy)-5-fluorobenzonitrile |
| 15 | 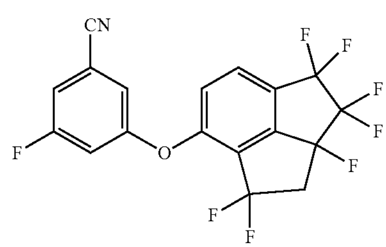 [SMILES: N#Cc1cc(F)cc(Oc2ccc3c4c2C(F)(F)CC4(F)C(F)(F)C3(F)F)c1] | 3-fluoro-5-((1,1,2a,3,3,4,4-heptafluoro-2,2a,3,4-tetrahydro-1H-cyclopenta[cd]inden-7-yl)oxy)benzonitrile |
| 16 | 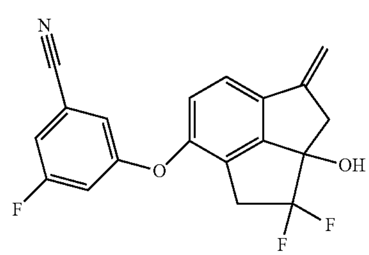 [SMILES: C=C1CC2(O)c3c1ccc(Oc1cc(F)cc(C#N)c1)c3CC2(F)F] | 3-((3,3-difluoro-2a-hydroxy-1-methylene-2,2a,3,4-tetrahydro-1H-cyclopenta[cd]inden-5-yl)oxy)-5-fluorobenzonitrile |

TABLE I-continued

| Compound # | Structure | Name |
|---|---|---|
| 17 | 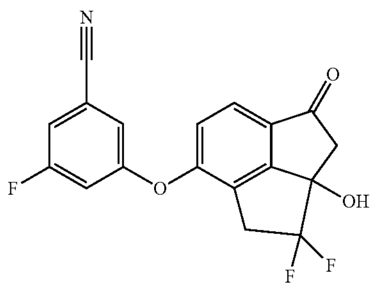 [SMILES: N#Cc1cc(F)cc(Oc2ccc3c4c2CC(F)(F)C4(O)CC3=O)c1] | 3-((3,3-difluoro-2a-hydroxy-1-oxo-2,2a,3,4-tetrahydro-1H-cyclopenta[cd]inden-5-yl)oxy)-5-fluorobenzonitrile |
| 18 | 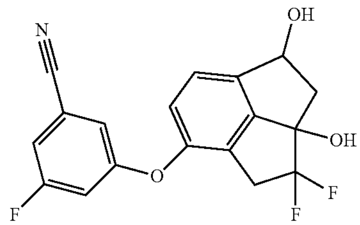 [SMILES: N#Cc1cc(F)cc(Oc2ccc3c4c2CC(F)(F)C4(O)CC3O)c1] | 3-((3,3-difluoro-1,2a-dihydroxy-2,2a,3,4-tetrahydro-1H-cyclopenta[cd]inden-5-yl)oxy)-5-fluorobenzonitrile |
| 19 | 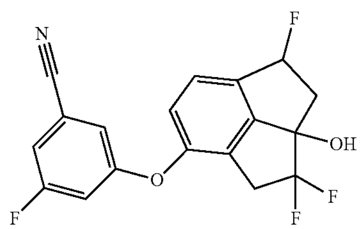 [SMILES: N#Cc1cc(F)cc(Oc2ccc3c4c2CC(F)(F)C4(O)CC3F)c1] | 3-fluoro-5-((1,3,3-trifluoro-2a-hydroxy-2,2a,3,4-tetrahydro-1H-cyclopenta[cd]inden-5-yl)oxy)benzonitrile |
| 20 | 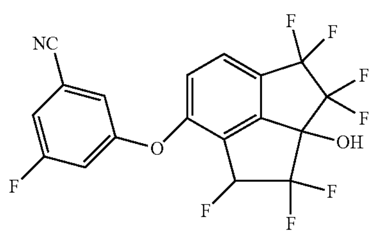 [SMILES: N#Cc1cc(F)cc(Oc2ccc3c4c2C(F)C(F)(F)C4(O)C(F)(F)C3(F)F)c1] | 3-fluoro-5-((1,2,2,3,3,4,4-heptafluoro-2a-hydroxy-2,2a,3,4-tetrahydro-1H-cyclopenta[cd]inden-7-yl)oxy)benzonitrile |
| 21 | 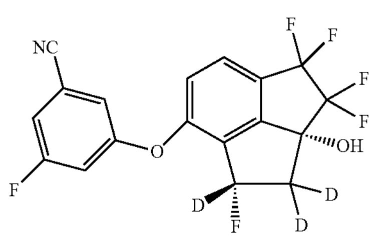 [SMILES: [2H]C1([2H])[C@@]2(O)c3c(ccc(Oc4cc(F)cc(C#N)c4)c3[C@@]1([2H])F)C(F)(F)C2(F)F] | 3-fluoro-5-(((1S,2aR)-1,3,3,4,4-pentafluoro-2a-hydroxy-2,2a,3,4-tetrahydro-1H-cyclopenta[cd]inden-7-yl-1,2,2-d3)oxy)benzonitrile |
| 22 | 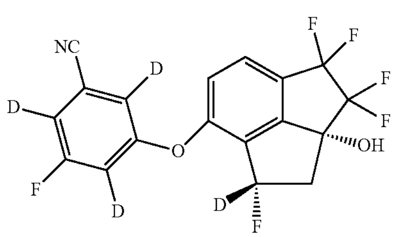 [SMILES: [2H]c1c(F)c([2H])c(Oc2ccc3c4c2[C@@]([2H])(F)C[C@]4(O)C(F)(F)C3(F)F)c([2H])c1C#N] | 3-fluoro-5-(((1S,2aR)-1,3,3,4,4-pentafluoro-2a-hydroxy-2,2a,3,4-tetrahydro-1H-cyclopenta[cd]inden-7-yl-1-d)oxy)benzonitrile-2,4,6-d3 |

TABLE I-continued

| Compound # | Structure | Name |
|---|---|---|
| 23a | 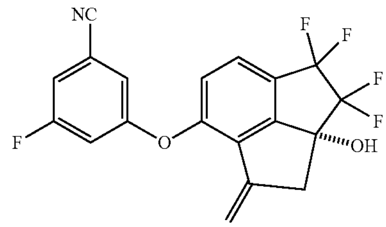 [SMILES: C=C1C[C@@]2(O)c3c(ccc(Oc4cc(F)cc(C#N)c4)c31)C(F)(F)C2(F)F] | (R)-3-fluoro-5-((3,3,4,4-tetrafluoro-2a-hydroxy-1-methylene-2,2a,3,4-tetrahydro-1H-cyclopenta[cd]inden-7-yl)oxy)benzonitrile |
| 23b | 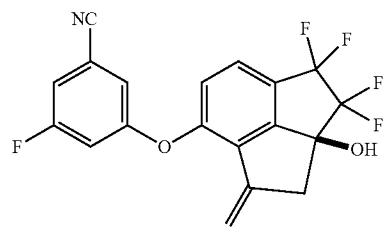 [SMILES: C=C1C[C@]2(O)c3c(ccc(Oc4cc(F)cc(C#N)c4)c31)C(F)(F)C2(F)F] | (S)-3-fluoro-5-((3,3,4,4-tetrafluoro-2a-hydroxy-1-methylene-2,2a,3,4-tetrahydro-1H-cyclopenta[cd]inden-7-yl)oxy)benzonitrile |
| 24a | 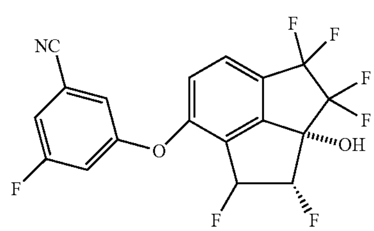 [SMILES: N#Cc1cc(F)cc(Oc2ccc3c4c2C(F)[C@@H](F)[C@]4(O)C(F)(F)C3(F)F)c1] | 3-fluoro-5-(((2S,2aS)-1,2,3,3,4,4-hexafluoro-2a-hydroxy-2,2a,3,4-tetrahydro-1H-cyclopenta[cd]inden-7-yl)oxy)benzonitrile |
| 24b | 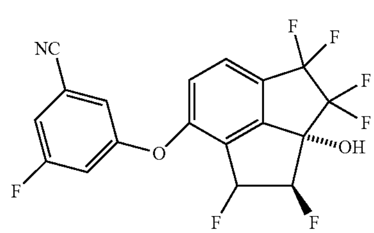 [SMILES: N#Cc1cc(F)cc(Oc2ccc3c4c2C(F)[C@H](F)[C@]4(O)C(F)(F)C3(F)F)c1] | 3-fluoro-5-(((2R,2aS)-1,2,3,3,4,4-hexafluoro-2a-hydroxy-2,2a,3,4-tetrahydro-1H-cyclopenta[cd]inden-7-yl)oxy)benzonitrile |

Additional representative compounds of Formula (I) that can be prepared are shown in Table II below:

| Compound # | Structure |
|---|---|
| II-1 | 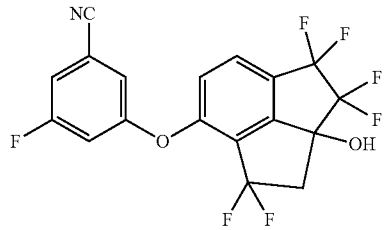 [SMILES: N#Cc1cc(F)cc(Oc2ccc3c4c2C(F)(F)CC4(O)C(F)(F)C3(F)F)c1] |
| II-4 | 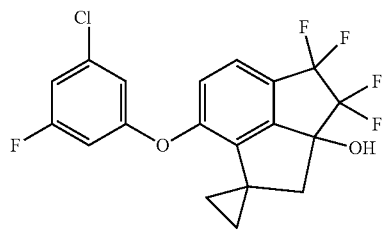 [SMILES: OC12CC3(CC3)c3c(Oc4cc(F)cc(Cl)c4)ccc(c31)C(F)(F)C2(F)F] |
| II-5 | 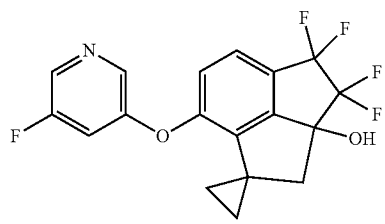 [SMILES: OC12CC3(CC3)c3c(Oc4cncc(F)c4)ccc(c31)C(F)(F)C2(F)F] |
| II-6 | 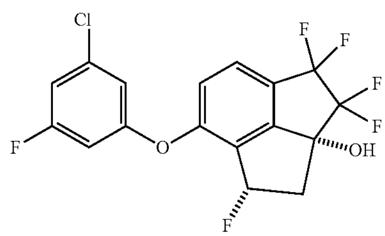 [SMILES: O[C@]12C[C@H](F)c3c(Oc4cc(F)cc(Cl)c4)ccc(c31)C(F)(F)C2(F)F] |
| II-7 | 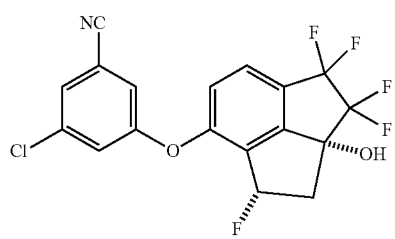 [SMILES: N#Cc1cc(Cl)cc(Oc2ccc3c4c2[C@@H](F)C[C@]4(O)C(F)(F)C3(F)F)c1] |
| II-8 | 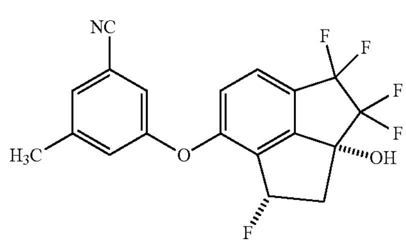 [SMILES: Cc1cc(C#N)cc(Oc2ccc3c4c2[C@@H](F)C[C@]4(O)C(F)(F)C3(F)F)c1] |
| II-10 | |
| II-11 | |
| II-12 | |
| II-13 | |
| II-14 | |
| II-15 | |

| Compound # | Structure |
|---|---|
| II-16 | (structure with fluorinated bicyclic core bearing OH, linked via O to 3-cyano-5-fluorophenyl group) |

General Synthetic Scheme

Compounds of this disclosure can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this disclosure can be synthesized, and various modifications to these schemes can be made and will be suggested to one skilled in the art reading this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., such as from about 0° C. to about 125° C. and further such as at about room (or ambient) temperature, e.g., about 20° C.

Compounds of Formula (I) where $X^1$ is CH, $R^1$ is hydroxyl, $R^3$, $R^4$, $R^5$, $R^6$, $R^7$, and $R^8$ are as defined in the Summary (or any embodiments thereof), and $R^9$ and $R^2$ are combined to form alkyldienyl, can be prepared as illustrated and described in Scheme 1 below.

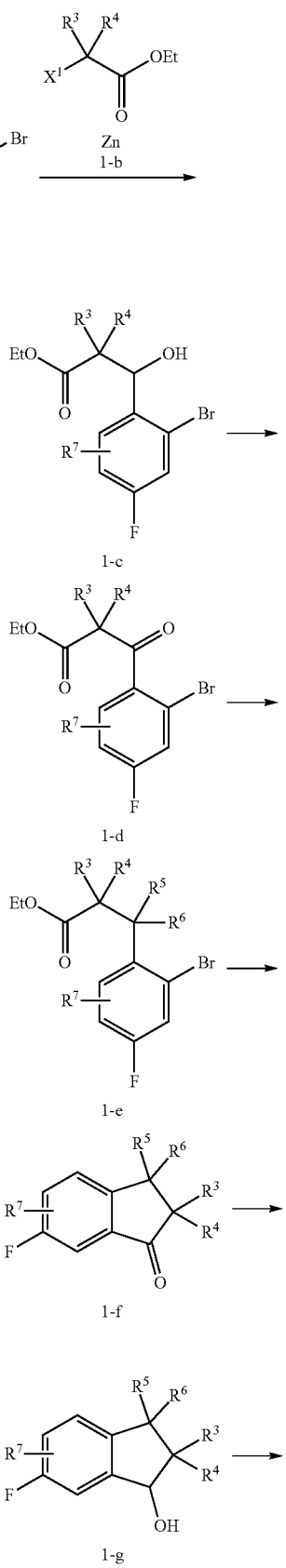

Scheme 1

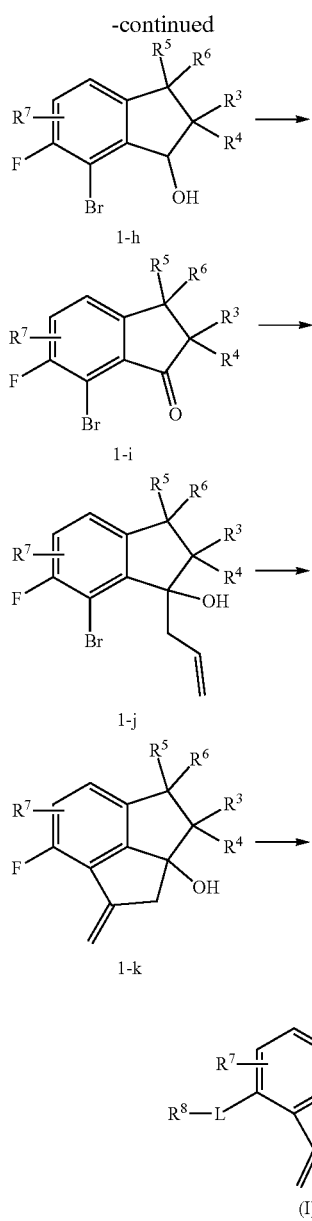

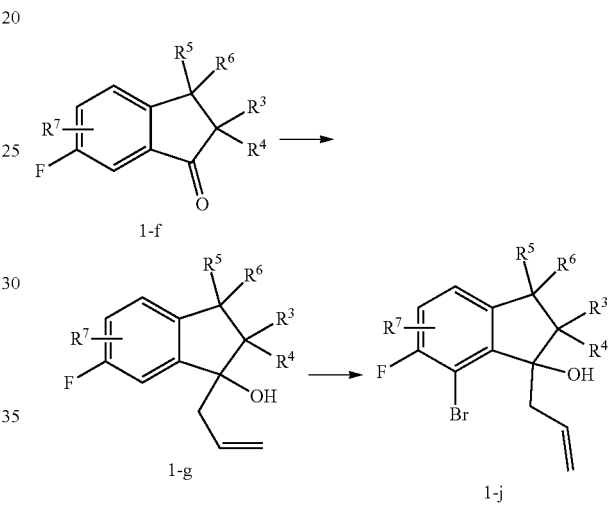

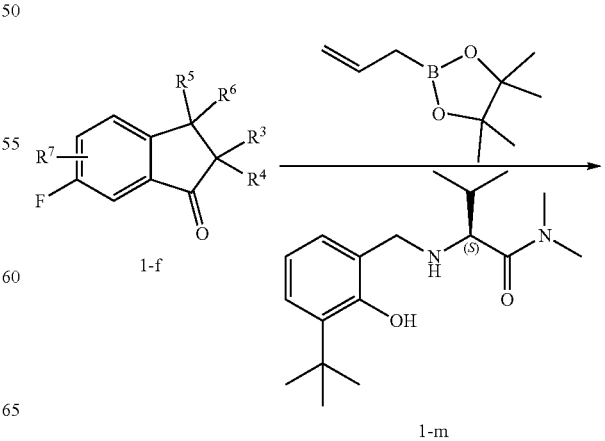

from 1-d by treatment with a fluorinating agent such as DAST or SF₄ under conditions well known in the art. Cyclization of 1-e can be achieved by treating it with alkyl lithium reagent such n-BuLi to give ketone 1-f. The carbonyl group in 1-f can be reduced with reducing reagents such as NaBH₄ to provide alcohol 1-g.

Compounds of formula 1-g can be converted to compounds of formula 1-h by lithiation of 1-g, followed by treating the lithio intermediate with CBr₄. Oxidation of 1-h with oxidative reagents such as IBX provides ketone of formula 1-i. Addition of allyl metal reagent such as allyl magnesium bromide to compounds of formula 1-i provides compounds of formula 1-j.

Alternatively, compound of formula 1-j can be prepared from 1-f by addition of allyl metal reagent such as allyl magnesium bromide to compounds of formula 1-f illustrated below:

Lithiation of 1-g with bases such LDA followed by treating the lithio intermediate with bromination reagent such as CBr₄ or 1,2-dibromotetrafluoroethane provides compound of formula 1-j. If desired, enantioselective synthesis of compounds of formula 1-g can be achieved by addition of 2-allyl-4,4,5,5-tetramethyl-1,3,2-dioxaborolane to compounds of formula 1-f in the presence of a ligand such as 1-m and a suitable base such as tBuONa in organic solvents such as MeOH, toluene as depicted below:

Reformastky reaction between an aldehyde of formula 1-a where $R^7$ is as described in the Summary or a precursor group thereof and a compound of formula 1-b where $X^1$ is halide and $R^3$ is as defined, e.g., independently hydrogen, deuterium, alkyl, halo, haloalkyl, hydroxyalkyl, or alkoxyalkyl, mediated by zinc metal provides a compound of formula 1-c. Compounds of formula 1-a and 1-b are commercially available or they can be prepared by methods well known in the art. For example, 2-bromo-4-fluorobenzaldehyde, ethyl 2-bromo-2,2-difluoroacetate, ethyl 2-bromo-2-methylpropanoate, ethyl 2-bromopropanoate, ethyl 2-bromoacetate are commercially available. The hydroxyl group in 1-c can be oxidized under oxidative conditions such as 2-iodoxybenzoic acid (IBX) or TPAP, NMO to give a ketone of formula 1-d. The keto group in compound of formula 1-d can be functionalized to provide compound of formula 1-e where $R^5$ and $R^6$ are as described in the Summary by methods well known in the art. For example, a compound of formula 1-e where $R^5$ and $R^6$ are fluoro can be synthesized

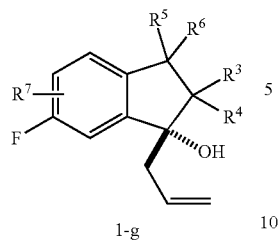

1-g

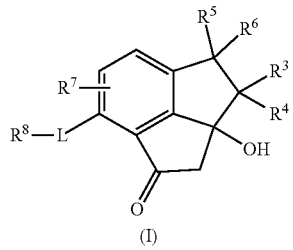

(I)

Compounds of formula 1-j can undergo cyclization in the presence of Pd catalyst with suitable ligands such as Pd(dppf)Cl$_2$ CH$_2$Cl$_2$ or Pd(PPh$_3$)$_2$Cl$_2$ to provide compounds of formula 1-k. The fluoro group in compounds of formula 1-k can be converted to a group of formula-L-R$^8$ where L and R$^8$ are as described in the Summary by treating compound 1-k with a compound of formula R$^8$-LH where L is N, O, or S and R$^8$ is a defined in the Summary by method well known in the art. Compounds of formula R$^8$-LH are commercially available or they can be prepared by methods well known in the art. For example, 3-fluoro-5-hydroxybenzonitrile, 3,5-difluorophenol, 3-chloro-5-fluorophenol, 3-chloro-5-hydroxy-benzonitrile, 5-fluoropyridin-3-ol, 5-chloropyridin-3-ol, 5-hydroxynicotinonitrile, 3-fluoro-5-mercaptobenzonitrile, 3-amino-5-fluorobenzonitrile, 3,3-difluorocyclobutan-1-ol, 3-amino-5-fluorobenzonitrile, 3-fluoro-5-mercaptobenzonitrile, 3-chloro-5-mercaptobenzonitrile, 3-amino-5-chlorobenzonitrile are commercially available.

Compounds of Formula (I) where R$^1$ is hydroxyl, R$^3$, R$^4$, R$^5$, R$^6$, R$^7$, and R$^8$ are as defined in the Summary (or any embodiments thereof), and R$^9$ and R$^2$ are combined to form oxo can be prepared as illustrated and described in Scheme 2 below.

Compounds of Formula 1-k can be converted to compounds of Formula 1-l by treating it with an oxidative cleavage reagent such as NaIO$_4$ and RuCl$_3$ hydrate under conditions well known in the art. The fluoro group in compounds of Formula 1-I can be converted to a group of formula-L-R$^8$ where L and R$^8$ are as described in the Summary by treating compound 1-1 with a compound of formula R$^8$-LH.

Compounds of Formula (I) can be converted to other compounds of Formula (I) by methods well known in the art. For example, compounds of Formula (I) where with R$^1$ is hydroxyl, R$^2$ is hydrogen and R$^9$ is hydroxy or fluoro can be synthesized from the compounds of Formula (I) where R$^9$ and R$^2$ are combined to form oxo by further functionalizing the carbonyl group as illustrated and described in Methods (i) and (ii) below.

Scheme 2

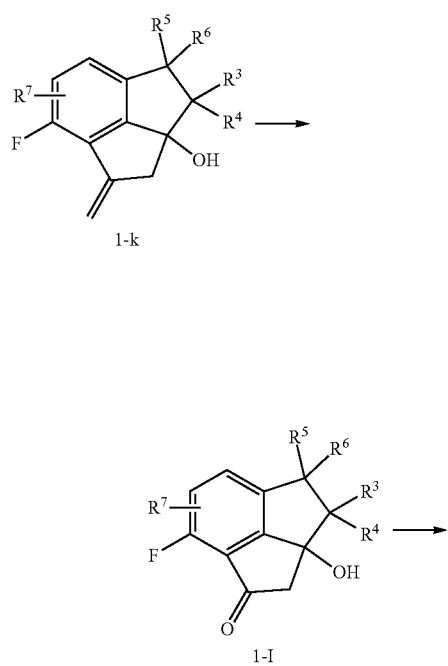

Method (i)

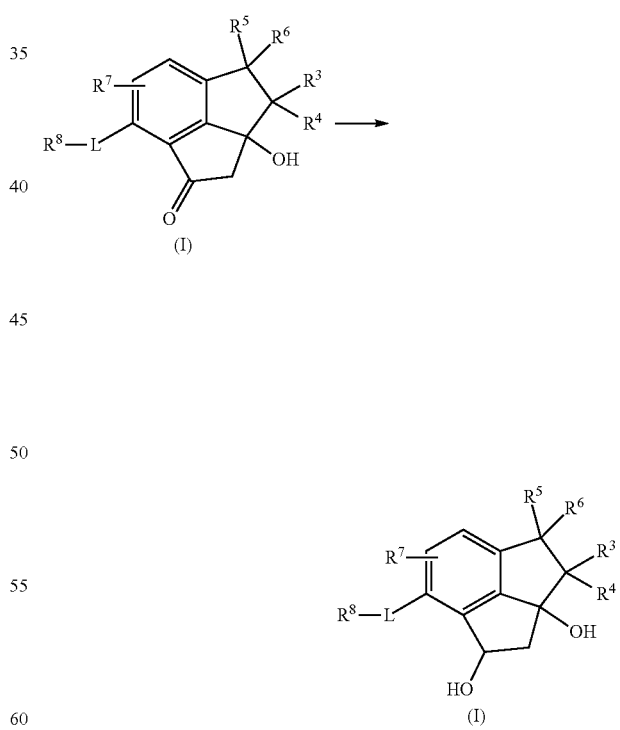

A compound of Formula (I) where R$^1$ is hydroxy, R$^9$ and R$^2$ are combined to form oxo can be converted to a compound of Formula (I) where R$^1$ is hydroxy, R$^9$ is hydroxy by treating it with reducing reagent such as sodium borohydride under conditions well known in the art.

Method (ii)

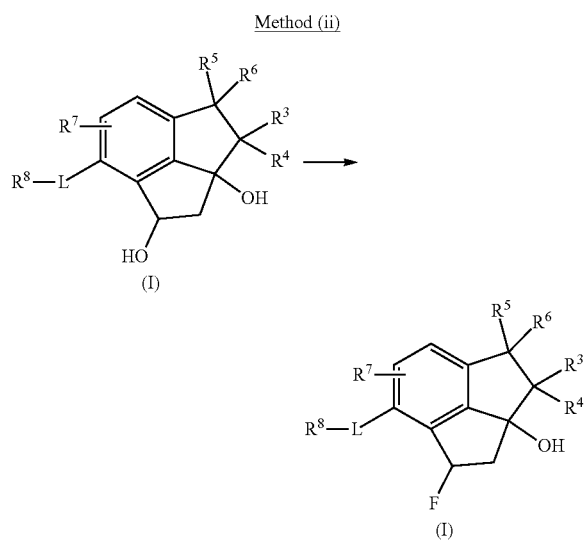

A compound of Formula (I) where $R^1$ is hydroxy, $R^9$ is hydroxy can be converted to a compound of Formula (I) where $R^1$ is hydroxy, $R^9$ is fluoro by treating it with fluorination reagent such as DAST under conditions well known in the art.

Utility

The compounds disclosed herein are useful for the treatment of HIF-2α mediated diseases, which include but are not limited to, various types of cancer, liver disease such as nonalcoholic steatohepatitis (NASH), inflammatory disease such as inflammatory bowel disease (IBD), pulmonary diseases such as pulmonary arterial hypertension (PAH), and iron load disorders.

HIF-2α plays an important role in the initiation and progression of many human cancers. Many extensive studies have demonstrated the critical role of increased HIF-2x activity in driving clear cell renal cell carcinoma (ccRCC) (see review by Shen and Kaelin, Seminars in Cancer Biology 23: 18-25, 2013). Abnormal HIF-2α activity is largely due to loss of function of a tumor suppressor, VHL. It is known that over eighty percent of ccRCC have defective VHL either through deletion, mutation or disturbed post-translational modification. Defective VHL leads to constitutively active HIF-α proteins regardless of oxygen level. Various studies employing gain-of-function and loss-of-function approaches in mouse models have demonstrated that HIF-2α is the key oncogenic substrate of VHL (see Kondo, et al. Cancer Cell 1: 237-246, 2002; Kondo, et al. PLOS Biology 1: 439-444, 2002; Maranchi, et al. Cancer Cell 1: 247-255, 2002; Zimmer, et al. Mol. Cancer Res 2: 89-95, 2004). For example, knockdown of HIF-2α in VHL-null tumors inhibited tumor formation; while reintroduction of VHL and overexpression of HIF-2α overcame the tumor suppressive role of VHL. Moreover, single nucleotide polymorphism in HIF-2α, is associated with resistant to PHD-mediated degradation, has been linked to an increased risk of developing RCC. In addition to serving as an archetypical tumor-initiating event in ccRCC, the VHL-HIF-2α axis has also been implicated in ccRCC tumor metastasis through its downstream CXCR4 and CYTIP (see Vanharanta et al. Nature Medicine 19: 50-59, 2013; Peter Staller et al. Nature. 2003 Sep. 18; 425(6955):307-11). Taken together, these studies strongly support the potential therapeutic utility of HIF-2α targeted agents for the treatment of ccRCC.

Defective VHL not only predisposes patients to kidney cancer (with a 70% lifetime risk), but also to hemangioblastomas, pheochromocytoma, endolymphatic sac tumors and pancreatic neuroendocrine tumors. Tumors derived from defective VHL are frequently driven by the constitutively active downstream HIF-α proteins, with the majority of these dependent on HIF-2α activity (see Maher, et al. Eur. J. Hum. Genet. 19: 617-623, 2011). Both genetic and epigenetic mechanisms can lead to the loss of function in VHL. Epigenetic inactivation of VHL expression and thus constitutive activation of HIF-α proteins has been found in many cancers including RCC, multiple myeloma, retinoblastoma, NSCLC, pancreatic endocrine tumors, squamous cell carcinoma, acute myeloid leukemia, myelodysplastic syndrome, and esophageal squamous cell carcinoma (see reviewed in Nguyen, et al. Arch. Phann. Res 36: 252-263, 2013). HIF-2α has also been linked to cancers of the retina, adrenal gland and pancreas through both loss of function in VHL and activating mutations in HIF-2α. Recently, gain-of-function HIF-2α mutations have been identified in erythrocytosis and paraganglioma with polycythemia (see Zhuang, et al. NEJM 367:922-930, 2012; Percy, et al. NEJM 358: 162-168, 2008; and Percy, et al. Am. J. Hematol. 87:439-442, 2012). Notably, many of the known HIF-2α target gene products (e.g., VEGF, PDGF, and cyclin Dl) have been demonstrated to play pivotal roles in cancers derived from kidney, liver, colon, lung, and brain. Thus, a HIF-2α targeted therapy could be beneficial for the above cancers when driven by these signaling events downstream of abnormal HIF-2α pathway activation. In addition to loss of function in VHL and activating mutation of HIF-2α, HIF-α proteins are also frequently upregulated in the intratumor environment of rapidly growing tumors, due to the hypoxic condition resulting from poor vascularization in large tumors. The activated HIF-α pathways, in turn, further promotes tumor cell survival and proliferation by transcriptionally upregulating various essential factors.

A large body of studies have demonstrated a correlation between HIF-2α overexpression and poor prognosis in various cancers including cancers of astrocytoma, breast, cervical, colorectal, glioblastoma, glioma, head and neck, liver, non-small cell lung, melanoma, neuroblastoma, ovarian, and prostate, thereby supporting the pursuit of HIF-2α as a therapeutic target in treating these cancers (see reviewed in Keith, et al. Nature Rev. Cancer 12: 9-22, 2012). HIF-2α has been demonstrated to augment the growth of APC mutant colorectal cancer through its regulation of genes involved in proliferation, iron utilization and inflammation (see Xue, et al. Cancer Res 72: 2285-2293, 2012; and Xue and Shah, Carcinogenesis 32: 163-169, 2013). In hepatocellular carcinoma (HCC), knock-down of HIF-2α in preclinical models led to the inhibition of cell proliferation in vitro and tumor growth in vivo through the downregulation of VEGF and cyclin D 1 (see He, et al. Cancer Sci. 103: 528-534, 2012). In NSCLC, around 50% of patients exhibited overexpression of HIF-2α protein, which strongly correlates with higher VEGF expression and more importantly, reduced overall survival. Interestingly, HIF-1 α does not correlate with reduced overall survival in lung cancer patients even though its expression is also often increased (see Giatromanolaki, et al. Br. J. Cancer 85: 881-890, 2001). Extensive studies in mice engineered with both non-degradable HIF-2α and mutant KRAS tumors have demonstrated an increased tumor burden and a decreased survival when compared to mice with only mutant KRAS expression (see Kim, et al. J. Clin. Invest. 119: 2160-2170, 2009). These studies demonstrate that HIF-2α promotes tumor growth and progression in lung cancer, and also negatively correlates with clinical prognosis.

HIF-2αs activity has been linked to the progression of chronic obstructive pulmonary disease (COPD), in addition to lung cancer, in mouse models (see Karoor, et al. Cancer Prev. Res. 5: 1061-1071, 2012). HIF-2α activity has also been demonstrated to be important in cancers of the central nervous system (see Holmquist-Mengelbier, et al. Cancer Cell 10: 413-423, 2006 and Li, et al. Cancer Cell 15: 501-513, 2009). HIF-2α knockdown reduced tumor growth in preclinical animal models of neuroblastoma, Conversely, increased level of HIF-2α correlated with advanced disease, poor prognosis and higher VEGF levels, which likely contribute to the poor clinical outcome. Similarly, higher HIF-2α expression has been correlated with a poor survival in glioma. Experimentally, inhibition of HIF-2α in glioma stem cells reduced cell proliferation and survival in vitro and tumor initiation in vivo. While HIF-1α is expressed in both neural progenitors and brain tumor stem cells, HIF-2α is found exclusively in the latter. Moreover, survival of glioma patients correlates to with HIF-2α, but not HIF-1α level.

One of downstream HIF-2α effector is cyclin D, an essential partner for the activation of CDK4 and CDK6. Therefore, administration of a HIF-2α inhibitor with CDK4/6 inhibitors, including abemaciclib (Verzenio®), palbociclib (Ibrance®) and ribociclib (Kisqali®) should result in downregulation of cyclin D, thereby increasing antiproliferative effects of CDK4/6 inhibitors. A recent study (Nicholson et al Sci Signal. 2019 Oct. 1; 12 (601)) suggests that the antiproliferative effects of CDK4/6 inhibition were synergistic with HIF-2α inhibition in HIF-2α-dependent VHL−/−ccRCC cells.

Radiation therapy is frequently used for approximately 50% of cancer patients, either alone or in combination with other therapies. However, the hypoxia microenvironment within the tumor has long been associated with resistance to radiation therapy. Bhatt and co-workers found that decreased level of HIF-2α leads to increased sensitivity to ionizing radiation in renal cell carcinoma cell lines (see Bhatt, et al. BJU Int. 102:358-363, 2008). Furthermore, mechanistic studies from Bertout et. al, have demonstrated that HIF-2α inhibition enhances the effectiveness of radiation through increased p53-dependent apoptosis (see Bertout, et al. PNAS 106:14391-14396, 2009). Thus, HIF-2α targeted therapy could improve the response to radiation therapy in various cancers.

Somatostatinomas are somatostatin-producing neuroendocrine tumors that are rare but often malignant. It has been found that HIF-2α mutations lead to the disruption of the prolyl hydroxylation domain (PHD) of HIF-2α, thus abolish the modification by PHDs, and subsequently reduce HIF-2α degradation mediated by VHL (see Yang, et al. Blood. 121: 2563-2566, 2013). The stabilized HIF-2α can then translocate to the nucleus, driving increased expression of hypoxia-related genes to contribute to somatostatinoma. Thus, a HIF-2α inhibitor will provide an alternative approach in treating somatostatinoma.

Polycythaemia is a hematologic disorder characterized by elevated hematocrit (the volume percentage of red blood cells in the blood), also known as erythrocytosis. Gain-of-function mutations in HIF-2α are associated with autosomal dominant erythrocytosis (see Percy, et al. N. Engl. J. Med. 358: 162-8, 2008 and Wilson et al. Case Rep Hematol. 6373706, 2016). In addition, mutations in PHD of HIF-2α, which is responsible in signaling HIF-2α for ubiquitination and degradation by VHL, have also been found to drive polycythaemia. Thus, inhibiting HIF-2α n, which is stabilized either by gain of function HIF-2α mutations or by loss of function mutations in PHD, VHL, by an HIF-2α inhibitor should be able to suppress HIF-2α downstream genes, such as EPO and thereby reducing hematocrit of polycythaemia.

Pheochromocytomas and paragangliomas (PPGLs) are rare neuroendocrine tumors that often develop on a background of predisposing genetic mutations, including loss of function in VHL or PHD2 or activating mutations of HIF-2α, all of which result in highly expressed HIF-2α protein and subsequently downstream genes to promote oncogenic progression (see Dahia, Nat Rev Cancer. 14:108-19, 2014). Furthermore, germline heterozygous mutations in genes encoding succinate dehydrogenase (SDH) subunits and the SDH complex assembly factor 2 protein (SDHAF2) have been described in patients with hereditary phaeochromocytoma and paraganglioma (PPGL). These mutations can lead to the accumulation of succinate, which in turn causes an inhibition of prolyl-hydroxylases that is essential in mediating ubiquitination/degradation of HIF proteins by VHL complex. Pituitary adenoma has been frequently found to be co-existing with PPGLs. Thus, inhibiting HIF-2α should be useful for treating both PPGLs and pituitary tumors. Succinate dehydrogenase subunits mutations have also been associated with gastrointestinal stromal tumors (GIST), thus supporting exploration of HIF-2α inhibitor for the treatment of GIST (see Janeway, et al. Proc. Natl Acad. Sci. USA 108:314-318, 2011).

Loss-of-function mutations of fumarate hydratase (FH) predispose patients to the autosomal dominant syndrome of both cutaneous and uterine leiomyomatosis. It has been suggested that activation of HIF proteins contributes to FH-associated tumor development by activation of hypoxia pathways. (see O'Flaherty, et al. Hum Mol Genet. 19:3844-3851, 2010 and Wei, et al. J Med Genet. 43:18-27, 2006). Furthermore, high expression of HIF-2α is found in leiomyosarcomas, a rare neoplasm of smooth-muscle origin (see Mayer, et al. Cancer Res. 68:4719, 2008) Thus, inhibition of HIF-2α could be beneficial in treating both leiomyomas and leiomyosarcomas.

Retinal capillary hemangioblastomas can be the ocular manifestations of VHL diseases, which are caused by loss of tumor suppressor VHL. Upregulation of HIF-2α upon loss of VHL has been detected in retinal hemangioblastoma patients and is indicated to contribute to the aggressive course of retinal hemangioblastomas, resulting in the resistance to multiple anti-VEGF and radiation therapies (see Wang, et al. Graefes Arch. Clin. Exp. Ophthalmol. 252: 1319-1327, 2014). Moreover, uncontrolled blood vessel growth is a central pathological component of many human blindness disorders, including diabetic retinopathy, age-related macular degeneration, glaucoma, and retinopathy of prematurity. Neuronal cell death and vision loss observed in these diseases are often caused by aberrant, leaky vessels, results of pathological neovascularization (see Krock, et al. Genes Cancer. 2: 1117-1133, 2011). Given the causal role of HIFs in neovascularization, inhibitor of HIF-2α may have potential utility in treating various diseases of blindness. In fact, systemic reduction of HIF-2α expression with a hypomorphic Hif-2α allele caused marked decreases in retinal neovascularization that was accompanied by defects in EPO expression (see Morita, et al. EMBO J. 22: 1134-46, 2003).

In addition to a direct role in promoting the initiation, progression and metastasis of tumor cells (e.g. ccRCC), HIF-2α also indirectly contributes to tumorigenesis through augmenting the immunosuppressive effect of hypoxia within the tumor microenvironment. Expression of HIF-2α has been detected in cells of the myeloid lineage (see Talks K L, et dal. Am J Pathol. 2000; 157(2):411-421). For example, HIF-2α is shown to favor the polarization of macrophages to the immunosuppressive M2 phenotype and enhances migration and invasion of tumor-associated macrophages (see Imtiyaz H Z et al. J Clin Invest. 2010; 120 (8): 2699-2714). Thus, increased level of HIF-2α in tumor-associated macrophages (TAMs) is associated with high-grade human tumors and correlates with poor prognosis. Furthermore, HIF-2α can indirectly promote additional immunosuppressive pathways (e.g. adenosine and arginase etc.) by modulating the expression of key signaling regulators such as adenosine A2B/A2A receptors and arginase. These data support that HIF-2α is a potential therapeutic target for treating a broader range of inflammatory disorders and cancer either as a single agent or in combination with other therapeutic agents e.g., immunotherapies.

Due to the key roles of HIF-2α proteins in regulating physiological response to the fluctuation of oxygen levels, they have been causally associated with many hypoxia-related pathological processes in addition to cancer. One such disease is PAH, a debilitating and life-threatening disease with very poor prognosis. Recent studies demonstrated that HIF-2α contributes to the process of hypoxic pulmonary vascular remodeling, reduced plasticity of the vascular bed, and ultimately, debilitating PAH (see Andrew S., et al. Proc Natl Acad Sci USA. 2016 Aug. 2; 113(31): 8801-8806, Tang H, et al. Am J Physiol Lung Cell Mol Physiol. 2018 Feb. 1; 314(2):L256-L275.). These studies offered new understanding in the role of pulmonary endothelial HIF-2 in regulating the pulmonary vascular response to hypoxia, and offer an much needed new therapeutic strategy by targeting HIF-2α. Another example of hypoxia-related pathological processes is IBD, a chronic relapsing inflammatory disease of the intestine. It is found that intestinal inflammation and subsequently IBD arose when a dysregulated epithelial oxygen tension occurs and intensifies across epithelial villi in the intestine (see Shah Y. M., Molecular and Cellular Pediatrics, 2016 December; 3(1):1). HIF-2α activation contributes to IBD, while HIF-1α in intestinal epithelial cells is considered as a major protective factor in IBD (see Karhausen J, et al. J Clin Invest. 2004; 114 (8): 1098-1106; Furuta G T, et al. J Exp Med. 2001; 193(9): 1027-1034). Mechanistically, HIF-2α activation not only leads to the upregulation of pro-inflammatory cytokines which promotes IBD directly, but also results in loss of intestine barrier integrity, thus indirectly contributes to the manifestation of IBD. (see Xue X, et al. Gastroenterology. 2013; 145(4):831-841; Glover L E, et al. Proc Natl Acad Sci U.S.A. 2013; 110 (49): 19820-19825). Therefore, an HIF-2α inhibitor holds the promise of reverting the pro-inflammatory condition and increasing the intestinal barrier integrity, thus alleviate the symptoms of IBD.

HIF-2α inhibitor also represents a novel therapeutic approach in NASH, for which limited therapeutic options are available. A recent study showed that an intestine-specific disruption of HIF-2α led to a significant reduction of hepatic steatosis and obesity induced by high-fat-diet. Mechanistically, intestine HIF-2α positively regulates the gene encoding neuraminidase 3, thus regulates ceramide metabolism which contributes to the development of NASH (see Xie C, et al. Nat Med. 2017 November; 23(11):1298-1308.). Therefore, an HIF-2α inhibitor should have preventive and therapeutic effects on metabolic disorders, such as NASH.

Several connections between the level of HIF-2α and iron homeostasis have been identified (see Peyssonnaux C et al, Cell Cycle. 2008; 7(1):28-32). Multiple studies have demonstrated the important role of HIF-2α in iron load disorders. HIF-2α, not HIF-1α, has emerged as an important "local" regulator of intestinal iron status through its regulation of various genes essential in iron transport and absorption (see Mastrogiannaki M, et al. J Clin Invest. 2009; 119(5):1159-1166). Therefore, a small molecule inhibitor that targets HIF-2α holds promise of improving iron homeostasis in patients with iron disorders.

Accordingly, the present invention provides a method for treating or lessening the severity of a disease, condition, or disorder where activation or over activation of HIF-2α is implicated in the disease state. In another aspect, the present disclosure provides a method of treating renal cell carcinoma of a subject with a compound disclosed herein or a pharmaceutically acceptable salt thereof.

HIF-2α inhibitors also have therapeutic potentials for a broad range of non-cancer indications including but not limited to NASH, IBD, PAH, and iron overload.

Testing

The HIF2α inhibitory activity of the compounds of the present disclosure can be tested using the in vitro assay described in Biological Examples 1 below.

PHARMACEUTICAL COMPOSITIONS

In general, the compounds of this disclosure will be administered in a therapeutically effective amount by any of the accepted modes of administration for agents that serve similar utilities. Therapeutically effective amounts of compounds this disclosure may range from about 0.01 to about 500 mg per kg patient body weight per day, which can be administered in single or multiple doses. A suitable dosage level may be from about 0.1 to about 250 mg/kg per day; about 0.5 to about 100 mg/kg per day. A suitable dosage level may be about 0.01 to about 250 mg/kg per day, about 0.05 to about 100 mg/kg per day, or about 0.1 to about 50 mg/kg per day. Within this range the dosage can be about 0.05 to about 0.5, about 0.5 to about 5 or about 5 to about 50 mg/kg per day. For oral administration, the compositions can be provided in the form of tablets containing about 1.0 to about 1000 milligrams of the active ingredient, particularly about 1, 5, 10, 15, 20, 25, 50, 75, 100, 150, 200, 250, 300, 400, 500, 600, 750, 800, 900, and 1000 milligrams of the active ingredient. The actual amount of the compound of this disclosure, i.e., the active ingredient, will depend upon numerous factors such as the severity of the disease to be treated, the age and relative health of the patient, the potency of the compound being utilized, the route and form of administration, and other factors.

In general, compounds of this disclosure will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules, including enteric coated or delayed release tablets, pills or capsules are preferred) and the bioavailability of the drug substance.

The compositions are comprised of in general, a compound of this disclosure in combination with at least one pharmaceutically acceptable excipient. Acceptable excipients are non-toxic, aid administration, and do not adversely affect the therapeutic benefit of the compound of this disclosure. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the disclosure may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator. Other suitable pharmaceutical excipients and their formulations are described in Remington's Pharmaceutical Sciences, edited by E. W. Martin (Mack Publishing Company, 20th ed., 2000).

The level of the compound in a formulation can vary within the full range employed by those skilled in the art. Typically, the formulation will contain, on a weight percent (wt. %) basis, from about 0.01-99.99 wt. % of a compound of this disclosure based on the total formulation, with the balance being one or more suitable pharmaceutical excipients. For example, the compound is present at a level of about 1-80 wt. %.

Combinations and Combination Therapies

The compounds of this disclosure may be used in combination with one or more other drugs in the treatment of diseases or conditions for which compounds of this disclosure or the other drugs may have utility. Such other drug(s) may be administered, by a route and in an amount commonly used therefore, contemporaneously or sequentially with a compound of the present disclosure. When a compound of this disclosure is used contemporaneously with one or more other drugs, a pharmaceutical composition in unit dosage form containing such other drugs and the compound of the present disclosure is preferred. However, the combination therapy may also include therapies in which the compound of this disclosure and one or more other drugs are administered on different overlapping schedules. It is also contemplated that when used in combination with one or more other active ingredients, the compounds of the present disclosure and the other active ingredients may be used in lower doses than when each is used singly.

Accordingly, the pharmaceutical compositions of the present disclosure also include those that contain one or more other drugs, in addition to a compound of the present disclosure.

The above combinations include combinations of a compound of this disclosure not only with one other drug, but also with two or more other active drugs. Likewise, a compound of this disclosure may be used in combination with other drugs that are used in the prevention, treatment, control, amelioration, or reduction of risk of the diseases or conditions for which a compound of this disclosure is useful. Such other drugs may be administered, by a route and in an amount commonly used therefore, contemporaneously or sequentially with a compound of the present disclosure. When a compound of this disclosure is used contemporaneously with one or more other drugs, a pharmaceutical composition containing such other drugs in addition to the compound of this disclosure can be used. Accordingly, the pharmaceutical compositions of the present disclosure also include those that also contain one or more other active ingredients, in addition to a compound of this disclosure. The weight ratio of the compound of this disclosure to the second active ingredient may be varied and will depend upon the effective dose of each ingredient. Generally, an effective dose of each will be used.

Where the subject in need is suffering from or at risk of suffering from cancer, the subject can be treated with a compound of this disclosure in any combination with one or more other anti-cancer agents. In some embodiments, one or more of the anti-cancer agents are proapoptotic agents. Examples of anti-cancer agents include, but are not limited to, any of the following: gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec™), geldanamycin, 17-N-Allylamino-17-Demethoxygeldanamycin (17-AAG), flavopiridol, LY294002, bortezomib, trastuzumab, BAY 11-7082, PKC412, or PD184352, Taxol™, also referred to as "paclitaxel", which is a well-known anti-cancer drug which acts by enhancing and stabilizing microtubule formation, and analogs of Taxol™., such as Taxotere™. Compounds that have the basic taxane skeleton as a common structure feature, have also been shown to have the ability to arrest cells in the G2-M phases due to stabilized microtubules and may be useful for treating cancer in combination with the compounds described herein.

Suitable anti-cancer agents also include inhibitors of kinases associated cell proliferative disorder. These kinases include but not limited to Aurora-A, BTK, CDK1, CDK2, CDK3, CDK4, CDK6, CDK5, CDK7, CDK8, CDK9, ephrin receptor kinases, CHK1, CHK2, SRC, Yes, Fyn, Lck, Fer, Fes, Syk, Itk, Bmx, GSK3, JNK, MEK, PAK1, PAK2, PAK3, PAK4, PDK1, PKA, PKC, RAF, Rsk and SGK. In particular, inhibitors of CDK4/6, including abemaciclib (Verzenio), palbociclib (Ibrance) and ribociclib (Kisqali), have the potential to be synergistic with HIF-2α inhibitors and reverse the resistance to HIF-2α inhibition; mitogen-activated protein kinase signaling, e.g., U0126, PD98059, PD184352, PD0325901, ARRY-142886, SB239063, SP600125, BAY 43-9006, wortmannin, or LY294002; Syk inhibitors; antibodies (e.g., rituxan); MET inhibitor such as foretinib, carbozantinib, or crizotinib; VEGFR inhibitor such as sunitinib, sorafenib, regorafinib, lenvatinib, vandetanib, carbozantinib, axitinib; EGFR inhibitor such as afatinib, brivanib, carbozatinib, erlotinib, gefitinib, neratinib, lapatinib; PI3K inhibitor such as XL147, XL765, BKM120 (buparlisib), GDC-0941, BYL719, IPI145, BAY80-6946, BEX235 (dactolisib), CAL101 (idelalisib), GSK2636771, TG100-115; MTOR inhibitor such as rapamycin (sirolimus), temsirolimus, everolimus, XL388, XL765, AZD2013, PF04691502, PKI-587, BEZ235, GDC0349; MEK inhibitor such as AZD6244, trametinib, PD184352, pimasertinib, GDC-0973, AZD8330; CSF1R inhibitors (PLX3397, LY3022855, etc.) and CSF1R antibodies (IMC-054, RG7155, etc); TGF beta receptor kinase inhibitor such as LY2157299; BTK inhibitor such as ibrutinib.

Other anti-cancer agents include proteasome inhibitor such as carfilzomib, MLN9708, delanzomib, or bortezomib; BET inhibitors such as INCB054329, OTX015, CPI-0610; LSD1 inhibitors such as GSK2979552, INCB059872; HDAC inhibitors such as panobinostat, vorinostat; DNA methyl transferase inhibitors such as azacytidine, decitabine, and other epigenetic modulator; SHP-2 inhibitor such as TNO155; Bcl2 inhibitor ABT-199, and other Bcl-2 family protein inhibitors; HIF-2α inhibitors such as PT2977 and PT2385; Beta catenin pathway inhibitors, notch pathway inhibitors and hedgehog pathway inhibitors; Antibodies or other therapeutic proteins against VEGF include bevacizumab and aflibercept.

Other anti-cancer agents/drugs that can be used in combination with the compounds of the invention include, but are not limited to, liver X receptor (LXR) modulators, including LXR agonists and LXR beta-selective agonists; aryl hydrocarbon receptor (AhR) inhibitors.

Other anti-cancer agents that can be employed in combination with a compound of this disclosure include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or Ril2), interferon alfa-2a; interferon alfa-2b; interferon alfa-n1; interferon alfa-n3; interferon beta-la; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer agents that can be employed in combination with a compound of the disclosure include: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; Bfgf inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; R.sub.11 retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that can be employed in combination with a compound of this disclosure include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites include but are not limited to folic acid analog (e.g., methotrexate), or pyrimidine analogs (e.g., cytarabine), purine analogs (e.g., mercaptopurine, thioguanine, pentostatin).

Examples of natural products useful in combination with a compound of this disclosure include but are not limited to vinca alkaloids (e.g., vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents that can be employed in combination with a compound of this disclosure) include, but are not limited to, nitrogen mustards (e.g., mechloroethamine, cyclophosphamide, chlorambucil, melphalan, etc.), ethylenimine and methylmelamines (e.g., hexamethlymelamine, thiotepa), alkyl sulfonates (e.g., busulfan), nitrosoureas (e.g., carmustine, lomusitne, semustine, streptozocin, etc.), or triazenes (decarbazine, etc.). Examples of antimetabolites include, but are not limited to folic acid analog (e.g., methotrexate), or pyrimidine analogs (e.g., fluorouracil, floxuridine, cytarabine), purine analogs (e.g., mercaptopurine, thioguanine, pentostatin.

Examples of hormones and antagonists useful in combination a compound of this disclosure include, but are not limited to, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Other anti-cancer agents that can be employed in combination with a compound of the disclosure include: anticancer agents which act by arresting cells in the G2-M phases due to stabilized microtubules and include Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B. Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta *Medica*), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-1AABE (Cytoskeleton/Mt. Sinai School of Medicine), A-204197 (Abbott), T-607 (Tuiarik, also known as T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta *Medica*), D-68144 (Asta *Medica*), Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838 (Asta *Medica*), D-68836 (Asta *Medica*), Myoseverin B, D-43411 (Zentaris, also known as D-81862), A-289099 (Abbott), A-318315 (Abbott), HTI- 286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

One or more additional immune checkpoint inhibitors can be used in combination with a compound as described herein for treatment of HIF-2α-associated diseases, disorders or conditions. Exemplary immune checkpoint inhibitors include inhibitors (smack molecules or biologics) against immune checkpoint molecules such as CD27, CD28, CD40, CD122, CD96, CD73, CD39, CD47, OX40, GITR, CSF1R, JAK, PI3K delta, PI3K gamma, TAM, arginase, CD137 (also known as 4-1BB), ICOS, A2AR, A2BR, SHP-2, B7-H3, B7-H4, BTLA, CTLA-4, LAG3, TIM3, VISTA, CD96, TIGIT, PD-1, PD-L1 and PD-L2. In some embodiments, the immune checkpoint molecule is a stimulatory checkpoint molecule selected from CD27, CD28, CD40, ICOS, OX40, GITR, CD137 and STING. In some embodiments, the immune checkpoint molecule is an inhibitory checkpoint molecule selected from B7-H3, B7-H4, BTLA, CTLA-4, IDO, TDO, Arginase, KIR, LAG3, PD-1, TIM3, CD96, TIGIT and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), pidilizumab, SHR-1210, PDR001, or AMP-224. In some embodiments, the anti-PD-1 monoclonal antibody is nivolumab, or pembrolizumab or PDR001. In some embodiments, the anti-PD1 antibody is pembrolizumab.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A (atezolizumab) or MEDI4736 (durvalumab).

In some embodiments, the inhibitor of an immune checkpoint molecule is an inhibitor of CTLA-4, e.g., an anti-CTLA-4 antibody. In some embodiments, the anti-CTLA-4 antibody is ipilimumab or tremelimumab. In some embodiments, the inhibitor of an immune checkpoint molecule is an inhibitor of LAG3, e.g., an anti-LAG3 antibody. In some embodiments, the anti-LAG3 antibody is BMS-986016 or LAG525. In some embodiments, the inhibitor of an immune checkpoint molecule is an inhibitor of GITR, e.g., an anti-GITR antibody. In some embodiments, the anti-GITR antibody is TRX518 or, MK-4166, INCAGN01876 or MK-1248. In some embodiments, the inhibitor of an immune checkpoint molecule is an inhibitor of OX40, e.g., an anti-OX40 antibody or OX40L fusion protein. In some embodiments, the anti-OX40 antibody is MEDI0562 or, INCAGN01949, GSK2831781, GSK-3174998, MOXR-0916, PF-04518600 or LAG525. In some embodiments, the OX40L fusion protein is MEDI6383.

Compounds of the invention can also be used to increase or enhance an immune response, including increasing the immune response to an antigen; to improve immunization, including increasing vaccine efficacy; and to increase inflammation. In some embodiments, the compounds of the invention can be sued to enhance the immune response to vaccines including, but not limited, *Listeria* vaccines, oncolytic viarl vaccines, and cancer vaccines such as GVAX® (granulocyte-macrophage colony-stimulating factor (GM-CF) gene-transfected tumor cell vaccine). Anti-cancer vaccines include dendritic cells, synthetic peptides, DNA vaccines and recombinant viruses. Other immune-modulatory agents also include those that block immune cell migration such as antagonists to chemokine receptors, including CCR2 and CCR4; Sting agonists and Toll receptor agonists.

Other anti-cancer agents also include those that augment the immune system such as adjuvants or adoptive T cell transfer. Compounds of this application may be effective in combination with CAR (Chimeric antigen receptor) T cell treatment as a booster for T cell activation

EXAMPLES

The following preparations of compounds of Formula (IA)/(I) are given to enable those skilled in the art to more clearly understand and to practice the present disclosure. They should not be considered as limiting the scope of the disclosure, but merely as being illustrative and representative thereof.

Example 1

Synthesis of 3-fluoro-5-((3,3,4,4-tetrafluoro-2a-hydroxy-1-methylene-2,2a,3,4-tetrahydro-1H-cyclopenta[cd]inden-7-yl)oxy)benzonitrile

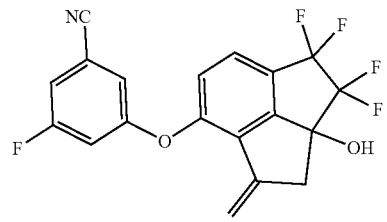 [SMILES: C=C1CC2(O)c3c(ccc(Oc4cc(F)cc(C#N)c4)c31)C(F)(F)C2(F)F]

Step 1: ethyl 3-(2-bromo-4-fluorophenyl)-2,2-difluoro-3-hydroxypropanoate

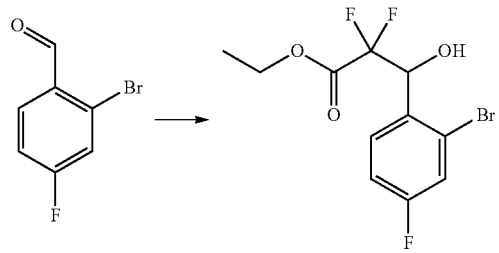 [SMILES: O=Cc1ccc(F)cc1Br ; CCOC(=O)C(F)(F)C(O)c1ccc(F)cc1Br]

To a stirred mixture of zinc (6.97 g, 106.56 mmol, 1.03 equiv.), 1,2-dibromoethane (388.71 mg, 2.069 mmol, 0.02 equiv.) and chlorotrimethylsilane (1.12 g, 10.31 mmol, 0.10 equiv.) in THF (200 mL) was added a solution of ethyl 2-bromo-2,2-difluoroacetate (21.0 g, 103.45 mmol, 1.0 equiv.) and 2-bromo-4-fluorobenzaldehyde (21.0 g, 103.45 mmol, 1.0 equiv.) in THF (100 mL) dropwise at room temperature under nitrogen atmosphere. The resulting mixture was stirred for 16 h at 75° C. under nitrogen atmosphere. The reaction was cooled and quenched with ice/water. The organic solvent was removed under vacuum and the resulting mixture was extracted with EtOAc. The combined organic layer was washed with water, dried over anhydrous $Na_2SO_4$ and concentrated under reduced pressure. The residue was purified by silica gel column chromatography, eluted with PE/EtOAc (5:1), to afford the title compound (18 g, 53.2%) as a yellow oil.

Step 2: ethyl 3-(2-bromo-4-fluorophenyl)-2,2-difluoro-3-oxopropanoate

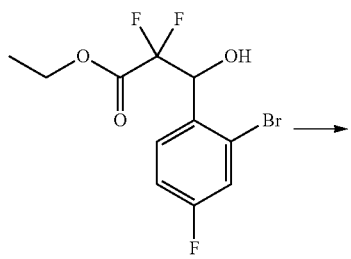

To a stirred solution of ethyl 3-(2-bromo-4-fluorophenyl)-2,2-difluoro-3-hydroxypropanoate (16 g, 48.9 mmol, 1.0 equiv.) in $CH_3CN$ (200 mL) was added 2-iodoxybenzoic acid (27.4 g, 97.83 mmol, 2.0 equiv.) at room temperature and the resulting mixture was stirred for 3 h at 80° C. The reaction solution was then cooled to room temperature, filtered and the filter cake was washed with EtOAc. The filtrate was concentrated under reduced pressure. The residue was purified by silica gel column chromatography, eluted with PE/EtOAc (10:1), to afford the title compound (10.3 g, 64.8%) as a yellow oil.

Step 3: ethyl 3-(2-bromo-4-fluorophenyl)-2,2,3,3-tetrafluoropropanoate

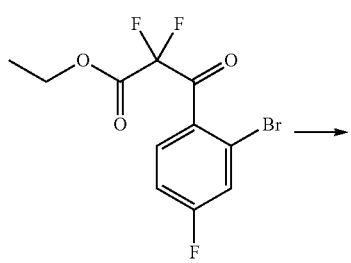

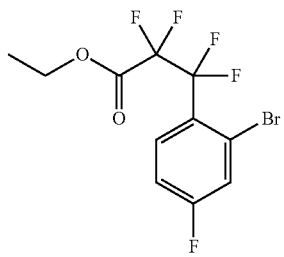

To a stirred solution of ethyl 3-(2-bromo-4-fluorophenyl)-2,2-difluoro-3-oxopropanoate (6.1 g, 18.8 mmol, 1.0 equiv.) in $CHCl_3$ (6 mL) was added DAST (30.25 g, 187.6 mmol, 10.0 equiv.) dropwise at room temperature and the resulting mixture was stirred for 16 h at 70° C. under nitrogen atmosphere. The reaction solution was allowed to cool to room temperature and quenched with ice/water. The mixture was extracted with DCM. The organic layer was dried over anhydrous $Na_2SO_4$ and concentrated. The residue was purified by silica gel column chromatography, eluted with PE/EtOAc (10:1), to afford the title compound (2.4 g, 36.8%) as yellow oil.

Step 4: 2,2,3,3,6-pentafluoro-2,3-dihydro-1H-inden-1-one

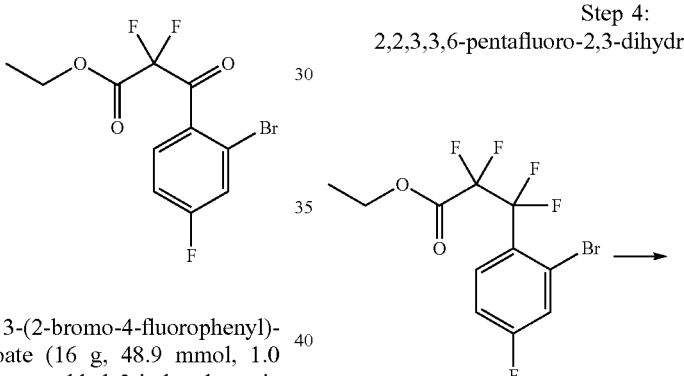

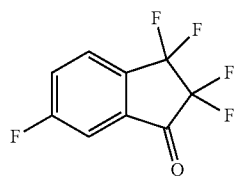

To a stirred solution of ethyl 3-(2-bromo-4-fluorophenyl)-2,2,3,3-tetrafluoropropanoate (4.20 g, 12.10 mmol, 1.0 equiv.) in THF (50 mL) was added n-BuLi (2.5 M, 7.26 mL, 18.15 mmol, 1.5 equiv.) dropwise at −78° C. under nitrogen atmosphere and the resulting mixture was stirred for 2 h between −70° C. and −80° C. under nitrogen atmosphere. The reaction was quenched with saturated $NH_4Cl$ (aq.) and extracted with EtOAc. The organic layer was dried over anhydrous $Na_2SO_4$ and concentrated under reduced pressure. The residue was purified by silica gel column chromatography, eluted with PE/EtOAc (20:1), to afford the title compound (2.25 g, 83.7%).

Step 5: 2,2,3,3,6-pentafluoro-2,3-dihydro-1H-inden-1-ol

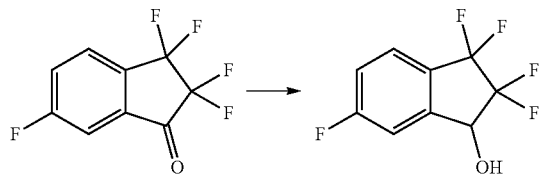 [SMILES: O=C1c2cc(F)ccc2C(F)(F)C1(F)F ; OC1c2cc(F)ccc2C(F)(F)C1(F)F]

To a stirred solution of 2,2,3,3,6-pentafluoro-2,3-dihydro-1H-inden-1-one (300 mg, 1.35 mmol, 1.0 equiv.) and triethylamine (273.35 mg, 2.70 mmol, 2.0 equiv.) in DCM (3 mL) was added formic acid (186.49 mg, 4.05 mmol, 3.0 equiv.) dropwise at 0° C., followed by the addition of RuCl(P-cymene)[(S,S)-Ts-DPEN] (8.59 mg, 0.014 mmol, 0.01 equiv). The resulting mixture was stirred for 3 h at room temperature under nitrogen atmosphere then washed with water. The organic layer was dried over anhydrous $Na_2SO_4$ and concentrated under reduced pressure. The residue was purified by silica gel column chromatography, eluted with PE/EtOAc (5:1), to afford the title compound (300 mg, 99.1%).

Step 6: 7-bromo-2,2,3,3,6-pentafluoro-2,3-dihydro-1H-inden-1-ol

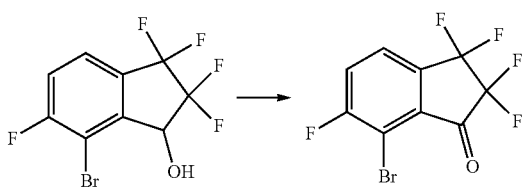 [SMILES: OC1c2c(ccc(F)c2Br)C(F)(F)C1(F)F ; O=C1c2c(ccc(F)c2Br)C(F)(F)C1(F)F]

To a stirred solution of 2,2,3,3,6-pentafluoro-2,3-dihydro-1H-inden-1-ol (2500 mg, 11.154 mmol, 1.00 equiv.) in tetrahydrofuran (60 mL) was added LDA (2.0 M, 16.73 mL, 33.463 mmol, 3.00 equiv.) dropwise at −78° C. under nitrogen atmosphere. The resulting mixture was warmed to −30° C. over 30 min and stirred for additional 30 min at −30° C. To the above mixture was added a solution of carbon tetrabromide (3699.05 mg, 11.154 mmol, 1.00 equiv.) in THF dropwise at −78° C. The resulting mixture was allowed warm to −30° C. over 30 min and stirred for additional 30 min at −30° C. The reaction was quenched with saturated $NH_4Cl$ (aq.) at −30° C. The resulting mixture was extracted with EtOAc and the organic layer was washed with brine, dried over anhydrous $Na_2SO_4$. After filtration, the filtrate was concentrated under reduced pressure. The residue was purified by silica gel column chromatography, eluted with PE/EtOAc (10:1), to afford the title compound (2600 mg, 76.9%) as a light yellow oil. MS (ES, m/z): [M−H]⁻=300.9, 302.9.

Step 7: 7-bromo-2,2,3,3,6-pentafluoro-2,3-dihydro-1H-inden-1-one

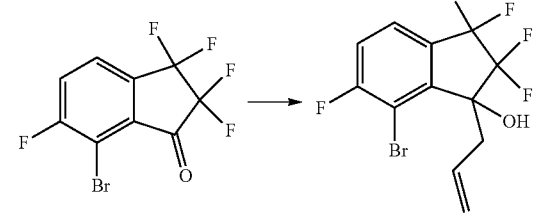

To a stirred mixture of 7-bromo-2,2,3,3,6-pentafluoro-2,3-dihydro-1H-inden-1-ol (2.63 g, 8.679 mmol, 1.00 equiv.) in $CH_3CN$ (45 mL) was added IBX (4.86 g, 17.356 mmol, 2.00 equiv) at room temperature. The resulting mixture was stirred for 3 h at 80° C., then cooled and filtered. The filter cake was washed with EtOAc. The combined filtrate was concentrated under reduced pressure. The residue was purified by silica gel column chromatography, eluted with PE/EtOAc (10:1), to afford the title compound (1.8 g, 68.9%) as an off-white solid.

Step 8: 1-allyl-7-bromo-2,2,3,3,6-pentafluoro-2,3-dihydro-1H-inden-1-ol

To a stirred solution of 7-bromo-2,2,3,3,6-pentafluoro-2,3-dihydro-1H-inden-1-one (100 mg, 0.332 mmol, 1.00 equiv.) in THF (3 mL) was added allylmagnesium bromide (1.0 M, 0.50 mL, 0.50 mmol, 1.50 equiv.) dropwise at −78° C. under nitrogen atmosphere. The resulting mixture was stirred for 1 h at −78° C. under nitrogen atmosphere. The reaction was quenched with saturated $NH_4Cl$ (aq.). The resulting mixture was extracted with EtOAc and the organic layer was dried over anhydrous $Na_2SO_4$. After filtration, the filtrate was concentrated under reduced pressure. The residue was purified by silica gel column chromatography, eluted with PE/EtOAc (5:1), to afford the title compound (90 mg, 79.0%) as a yellow oil. MS (ES, m/z): [M−H]⁻=340.9, 342.9.

Step 9: 3,3,4,4,7-pentafluoro-1-methylene-1,2,3,4-tetrahydro-2aH-cyclopenta[cd]inden-2a-ol

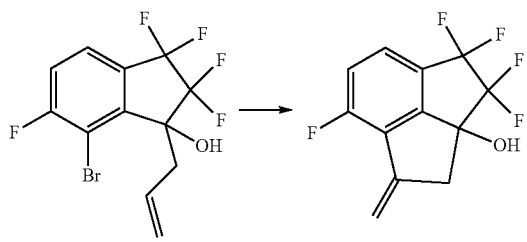 [SMILES: C=CCC1(O)c2c(ccc(F)c2Br)C(F)(F)C1(F)F ; C=C1CC2(O)c3c(ccc(F)c31)C(F)(F)C2(F)F]

To a stirred mixture of 1-allyl-7-bromo-2,2,3,3,6-pentafluoro-2,3-dihydro-1H-inden-1-ol (1050 mg, 3.060 mmol, 1.00 equiv.) in DMF (25 mL) were added AcONa (753.17 mg, 9.181 mmol, 3.00 equiv.) and Pd(dppf)Cl$_2$·CH$_2$Cl$_2$ (249.93 mg, 0.306 mmol, 0.10 equiv.) at room temperature. The resulting mixture was stirred for 3 h at 100° C. under nitrogen atmosphere. The resulting mixture was diluted with water and extracted with EtOAc. The combined organic layers were washed with water and brine, dried over anhydrous Na$_2$SO$_4$. After filtration, the filtrate was concentrated under reduced pressure. The residue was purified by silica gel column chromatography, eluted with PE/EtOAc (5:1), to afford the title compound (370 mg, 46.1%) as a light yellow oil.

Step 10: 3-fluoro-5-((3,3,4,4-tetrafluoro-2a-hydroxy-1-methylene-2,2a,3,4-tetrahydro-1H-cyclopenta[cd]inden-7-yl)oxy)benzonitrile

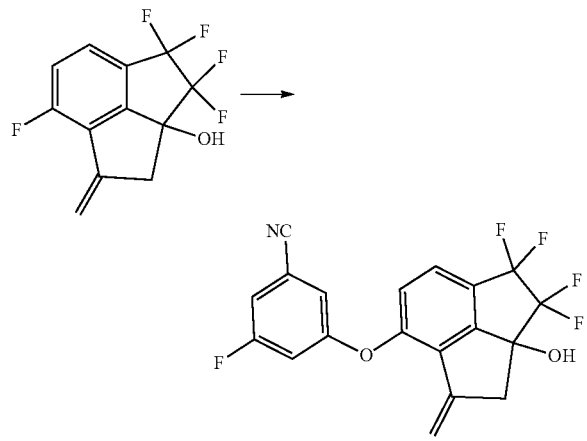

To a stirred mixture of 3,3,4,4,7-pentafluoro-1-methylene-1,2,3,4-tetrahydro-2aH-cyclopenta[cd]inden-2a-ol (40 mg, 0.15 mmol, 1.00 equiv.) and 3-fluoro-5-hydroxybenzonitrile (20.92 mg, 0.153 mmol, 1.00 equiv.) in DMF (1 mL) was added Cs$_2$CO$_3$ (49.71 mg, 0.15 mmol, 1.00 equiv.) at room temperature. The resulting mixture was stirred for 24 h at 100° C. The resulting mixture was filtered and the filtrate was purified by Prep-HPLC to afford (16.77 mg, 29.0%). MS (ES, m/z): [M–H]$^-$=378.1.

Example 2

Synthesis of 3-fluoro-5-((3,3,4,4-tetrafluoro-2a-hydroxy-1-oxo-2,2a,3,4-tetrahydro-1H-cyclopenta[cd]inden-7-yl)oxy)benzonitrile

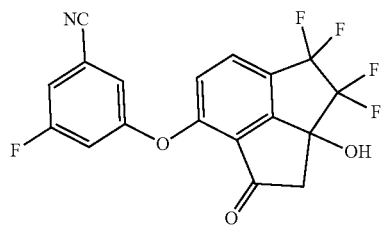 [SMILES: N#Cc1cc(F)cc(Oc2ccc3c4c2C(=O)CC4(O)C(F)(F)C3(F)F)c1]

Step 1: 3,3,4,4,7-pentafluoro-2a-hydroxy-2,2a,3,4-tetrahydro-1H-cyclopenta[cd]inden-1-one

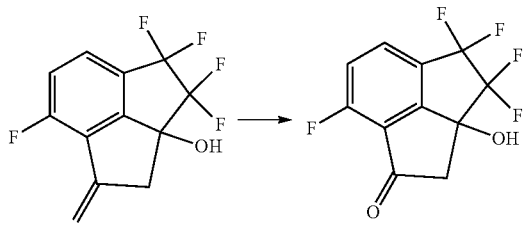 [SMILES: C=C1CC2(O)c3c(ccc(F)c31)C(F)(F)C2(F)F ; O=C1CC2(O)c3c(ccc(F)c31)C(F)(F)C2(F)F]

To a stirred mixture of 3,3,4,4,7-pentafluoro-1-methylene-1,2,3,4-tetrahydro-2aH-cyclopenta[cd]inden-2a-ol (320 mg, 1.22 mmol, 1.00 equiv.) in a mixed solvent (DCM/CH$_3$CN/H$_2$O=3 mL/3 mL/4.50 mL) were added NaIO$_4$ (1044.25 mg, 4.882 mmol, 4.00 equiv.) and RuCl$_3$·H$_2$O (13.76 mg, 0.061 mmol, 0.05 equiv.) at room temperature. The resulting mixture was stirred for 6 h at room temperature. The resulting mixture was diluted with water and extracted with DCM. The combined organic layers were washed with water and brine, dried over anhydrous Na$_2$SO$_4$. After filtration, the filtrate was concentrated under reduced pressure. The residue was purified by silica gel column chromatography, eluted with PE/EtOAc (3:1), to afford the title compound (250 mg, 77.5%) as a white solid. MS (ES, m/z): [M–H]$^-$=263.0.

Step 2: 3-fluoro-5-((3,3,4,4-tetrafluoro-2a-hydroxy-1-oxo-2,2a,3,4-tetrahydro-1H-cyclopenta[cd]inden-7-yl)oxy)benzonitrile

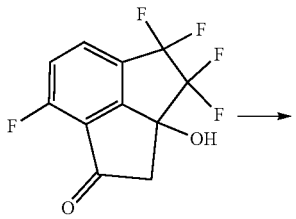

-continued

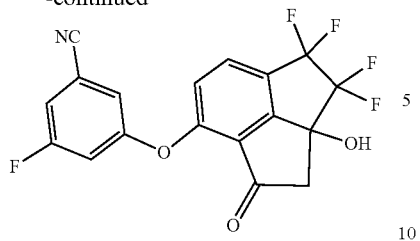

To a stirred mixture of 3,3,4,4,7-pentafluoro-2a-hydroxy-2,2a,3,4-tetrahydro-1H-cyclopenta[cd]inden-1-one (200 mg, 0.757 mmol, 1.00 equiv.) and 3-fluoro-5-hydroxybenzonitrile (103.81 mg, 0.757 mmol, 1.0 equiv.) in DMF (3 mL) was added Cs$_2$CO$_3$ (246.69 mg, 0.76 mmol, 1.0 equiv.) at room temperature. The resulting mixture was stirred for 16 h at room temperature. The resulting mixture was diluted with water and extracted with EtOAc. The combined organic layers were washed with water and brine, dried over anhydrous Na$_2$SO$_4$. After filtration, the filtrate was concentrated under reduced pressure. The residue was purified by silica gel column chromatography, eluted with PE/EtOAc (3:1), to afford the title compound (200 mg, 69.3%) as a white semi-solid. MS (ES, m/z): [M−H]$^-$=380.0.

Example 3

Synthesis of 3-fluoro-5-((3,3,4,4-tetrafluoro-1,2a-dihydroxy-2,2a,3,4-tetrahydro-1H-cyclopenta[cd]inden-7-yl)oxy)benzonitrile

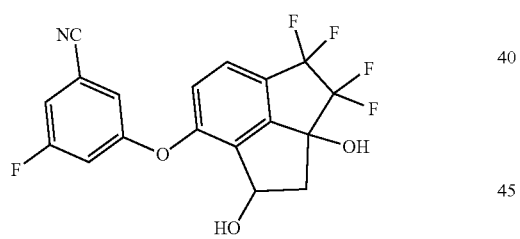

To a solution of 3-fluoro-5-((3,3,4,4-tetrafluoro-2a-hydroxy-1-oxo-2,2a,3,4-tetrahydro-1H-cyclopenta[cd]inden-7-yl)oxy)benzonitrile (40 mg, 0.105 mmol, 1.00 equiv.) in MeOH (1 mL) was added NaBH$_4$ (7.94 mg, 0.210 mmol, 2.0 equiv.) at room temperature. The resulting mixture was stirred for 3 h at room temperature. The reaction was quenched with aq. HCl (2.0 M) at room temperature to pH=7. The resulting mixture was concentrated under vacuum. The residue was diluted with water and extracted with EtOAc. The combined organic layers were washed with water, dried over anhydrous Na$_2$SO$_4$. After filtration, the filtrate was concentrated under reduced pressure. The residue was purified by prep-TLC, eluted with PE/EtOAc (3:1), to afford the title compound (40 mg, 99.5%) as a colorless oil. MS (ES, m/z): [M−H]$^-$=382.0.

Example 4

Synthesis of 3-fluoro-5-((1,3,3,4,4-pentafluoro-2a-hydroxy-2,2a,3,4-tetrahydro-1H-cyclopenta[cd]inden-7-yl)oxy)benzonitrile [4]

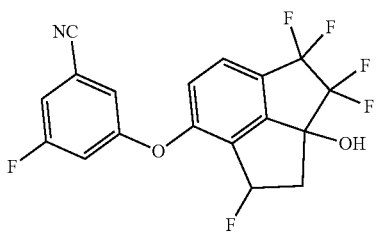 [SMILES: N#Cc1cc(F)cc(Oc2ccc3c4c2C(F)CC4(O)C(F)(F)C3(F)F)c1]

To a stirred solution of 3-fluoro-5-((3,3,4,4-tetrafluoro-1,2a-dihydroxy-2,2a,3,4-tetrahydro-1H-cyclopenta[cd]inden-7-yl)oxy)benzonitrile (20 mg, 0.05 mmol, 1.00 equiv.) in DCM (0.5 mL) was added DAST (6.73 mg, 0.04 mmol, 0.80 equiv.) dropwise at −50° C. The resulting mixture was stirred for 30 min at −50° C.−−40° C. The reaction mixture was quenched with NaHCO$_3$(aq.) and extracted with DCM. The organic layer was dried over anhydrous Na$_2$SO$_4$. After filtration, the filtrate was concentrated under reduced pressure. The residue was purified by Prep-HPLC to afford the title compound (4.3 mg, 21.3%) as a white solid. MS (ES, m/z): [M−H]=384.1.

Example 5

Synthesis of 1,3,3,4,4-pentafluoro-7-((5-fluoropyridin-3-yl)oxy)-1,2,3,4-tetrahydro-2aH-cyclopenta[cd]inden-2a-ol

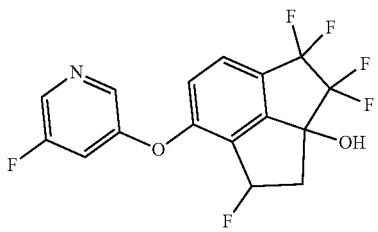 [SMILES: OC12CC(F)c3c(Oc4cncc(F)c4)ccc(c31)C(F)(F)C2(F)F]

Step 1: 3,3,4,4-tetrafluoro-7-((5-fluoropyridin-3-yl)oxy)-2a-hydroxy-2,2a,3,4-tetrahydro-1H-cyclopenta[cd]inden-1-one

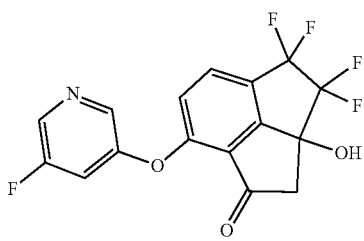 [SMILES: O=C1CC2(O)c3c(ccc(Oc4cncc(F)c4)c31)C(F)(F)C2(F)F]

To a stirred mixture of 3,3,4,4,7-pentafluoro-2a-hydroxy-2,2a,3,4-tetrahydro-1H-cyclopenta[cd]inden-1-one (95 mg, 0.36 mmol, 1.00 equiv.) and 5-fluoropyridin-3-ol (41 mg, 0.36 mmol, 1.00 equiv.) in DMF (2.00 mL) was added Cs$_2$CO$_3$ (128.90 mg, 0.40 mmol, 1.10 equiv.) at room temperature under nitrogen atmosphere. After stirring for 4 h at room temperature, the reaction mixture was quenched with water at 0° C. The resulting mixture was extracted with EtOAc. The combined organic layers were washed with brine and dried over anhydrous Na$_2$SO$_4$. After filtration, the filtrate was concentrated under reduced pressure. The residue was purified by Prep-TLC (PE/EtOAc=3/1) to afford the title compound (85 mg, 66%) as a white solid. MS (ES, m/z): [M+1]$^+$=358.1.

Step 2: 3,3,4,4-tetrafluoro-7-((5-fluoropyridin-3-yl)oxy)-1,2,3,4-tetrahydro-2aH-cyclopenta-[cd]indene-1,2a-diol

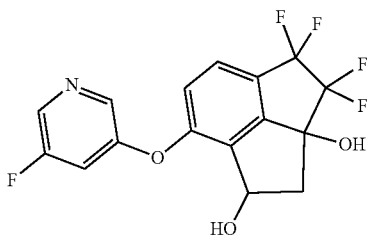 [SMILES: OC1CC2(O)c3c(ccc(Oc4cncc(F)c4)c31)C(F)(F)C2(F)F]

To a stirred solution of 3,3,4,4-tetrafluoro-7-((5-fluoropyridin-3-yl)oxy)-2a-hydroxy-2,2a,3,4-tetrahydro-1H-cyclopenta[cd]inden-1-one (85 mg, 0.24 mmol, 1.00 equiv.) in MeOH (1.50 mL) was added NaBH$_4$ (18 mg, 0.48 mmol, 2.00 equiv.) at room temperature. After stirring for 1 h at room temperature, the reaction mixture was quenched with saturated NH$_4$Cl (aq.) at 0° C. The resulting mixture was extracted with EtOAc and the combined organic layers were washed with brine and dried over anhydrous Na$_2$SO$_4$. After filtration, the filtrate was concentrated under reduced pressure. The residue was purified by silica gel column chromatography, eluted with EtOAc/PE (0-60%), to afford the title compound (80 mg, 93.7%) as a light yellow solid. MS (ES, m/z): [M+1]$^+$=360.1.

Step 3: 1,3,3,4,4-pentafluoro-7-((5-fluoropyridin-3-yl)oxy)-1,2,3,4-tetrahydro-2aH-cyclopenta[cd]inden-2a-ol

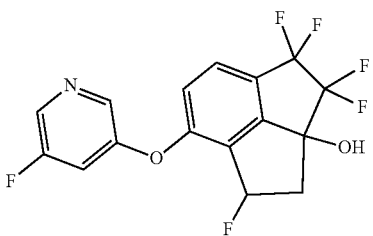 [SMILES: OC12CC(F)c3c(Oc4cncc(F)c4)ccc(c31)C(F)(F)C2(F)F]

To a stirred solution of 3,3,4,4-tetrafluoro-7-((5-fluoropyridin-3-yl)oxy)-1,2,3,4-tetrahydro-2aH-cyclopenta[cd]indene-1,2a-diol (30 mg, 0.08 mmol, 1.00 equiv.) in THF (1.00 mL) was added DAST (20 mg, 0.12 mmol, 1.50 equiv.) at −50° C. under nitrogen atmosphere. After stirring for 2 h at −50--30° C., the reaction mixture was quenched with saturated NaHCO$_3$(aq.) at 0° C. The resulting mixture was extracted with EtOAc and the combined organic layers were washed with brine and dried over anhydrous Na$_2$SO$_4$. After filtration, the filtrate was concentrated under reduced pressure. The crude product was purified by Prep-HPLC to afford the title compound (3 mg, 10%) as a white solid. MS (ES, m/z): [M+1]$^+$=362.1.

Example 6

Synthesis of 3-fluoro-5-((3,3,4,4-tetrafluoro-2a-hydroxy-2,2a,3,4-tetrahydrospiro-[cyclopenta[cd]indene-1,1'-cyclopropan]-7-yl)oxy)benzonitrile

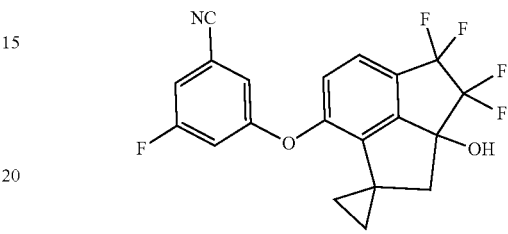

To a stirred mixture of diethylzinc (0.53 mL, 0.53 mmol, 1.0 M in hexane) in DCM (3 mL) was added TFA (60 mg, 0.526 mmol, 4.00 equiv.) dropwise at 0° C. under nitrogen atmosphere. The resulting mixture was stirred for 10 min at 0° C. To the above mixture was added CH$_2$I$_2$ (141 mg, 0.53 mmol, 4.0 equiv.) dropwise at 0° C. The resulting mixture was stirred for additional 10 min at 0° C., followed by the addition of 3-fluoro-5-((3,3,4,4-tetrafluoro-2a-hydroxy-1-methylene-2,2a,3,4-tetrahydro-1H-cyclopenta[cd]inden-7-yl)oxy)benzonitrile (50 mg, 0.132 mmol, 1.00 equiv.). The reaction mixture was stirred for 10 min at 0° C., then stirred for additional 1 h at room temperature. The reaction mixture was quenched with water and extracted with CH$_2$Cl$_2$. The combined organic layers were dried over anhydrous Na$_2$SO$_4$. After filtration, the filtrate was concentrated under reduced pressure and the crude product was purified by Prep-HPLC to afford the title compound (5.6 mg, 10.8%) as a white solid. MS (ES, m/z): [M−H]$^-$=392.1.

Example 7

Synthesis of 3-fluoro-5-((3,3,4,4-tetrafluoro-2a-hydroxy-1-methyl-2,2a,3,4-tetrahydro-1H-cyclopenta[cd]inden-7-yl)oxy)benzonitrile

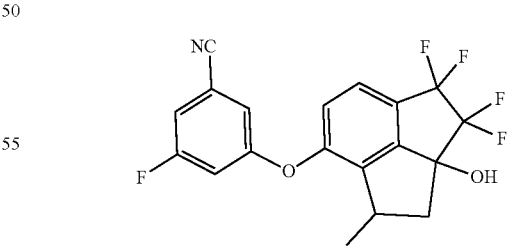

To a stirred mixture of 3-fluoro-5-((3,3,4,4-tetrafluoro-2a-hydroxy-1-methylene-2,2a,3,4-tetrahydro-1H-cyclopenta[cd]inden-7-yl)oxy)benzonitrile (30 mg, 0.08 mmol, 1.00 equiv.) and phenyl sulfide (1.47 mg, 0.008 mmol, 0.10 equiv.) in ethyl acetate (3 mL) and CH$_3$OH (3 mL) was added 10% Pd/C (20 mg) at room temperature. The resulting mixture was stirred for 48 h at room temperature under hydrogen atmosphere then filtered. The filtrate was concentrated under reduced pressure and the crude product was purified by Prep-HPLC to afford the title compound (9 mg, 30%) as a white solid. MS (ES, m/z): [M−H]⁻=380.1.

Example 8

Synthesis of 3-fluoro-5-((3,3,4,4-tetrafluoro-1,2a-dihydroxy-1-methyl-2,2a,3,4-tetrahydro-1H-cyclopenta[cd]inden-7-yl)oxy)benzonitrile

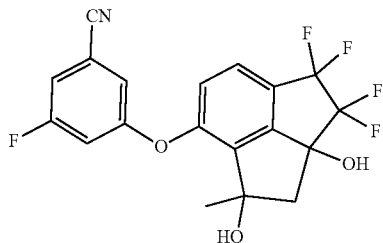 [SMILES: CC1(O)CC2(O)c3c(ccc(Oc4cc(F)cc(C#N)c4)c31)C(F)(F)C2(F)F]

To a stirred solution of 3-fluoro-5-((3,3,4,4-tetrafluoro-2a-hydroxy-1-oxo-2,2a,3,4-tetrahydro-1H-cyclo-penta[cd]inden-7-yl)oxy)benzonitrile (20 mg, 0.05 mmol, 1.00 equiv.) in THF (0.60 mL) was added bromo(methyl)magnesium (1.0 M, 0.16 mL, 0.16 mmol, 3.05 equiv.) dropwise at −78° C. under nitrogen atmosphere. The resulting mixture was stirred for 1 h at −78° C. under nitrogen atmosphere, then quenched with saturated NH₄Cl (aq.) (2 mL) at −78° C. The resulting mixture was extracted with EtOAc. The combined organic layers were washed with brine, dried over anhydrous Na₂SO₄. After filtration, the filtrate was concentrated under reduced pressure. The residue was purified by Prep-HPLC to afford the title compound (10 mg, 48.0%) as a white solid. MS (ES, m/z): [M−H]⁻=396.2.

Example 9

Synthesis of 3-fluoro-5-((1,3,3,4,4-pentafluoro-2a-hydroxy-1-methyl-2,2a,3,4-tetrahydro-1H-cyclopenta[cd]inden-7-yl)oxy)benzonitrile

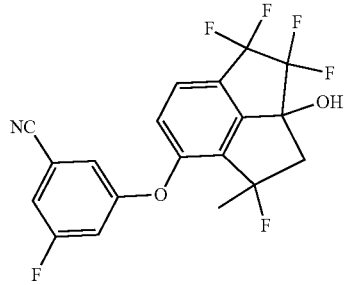 [SMILES: CC1(F)CC2(O)c3c(ccc(Oc4cc(F)cc(C#N)c4)c31)C(F)(F)C2(F)F]

To a stirred mixture of 3-fluoro-5-((3,3,4,4-tetrafluoro-1,2a-dihydroxy-1-methyl-2,2a,3,4-tetrahydro-1H-cyclopenta[cd]inden-7-yl)oxy)benzonitrile (30 mg, 0.07 mmol, 1.00 equiv.) in DCM (1.5 mL) was added DAST (12 mg, 0.07 mmol, 1.00 equiv.) dropwise at −50° C. under nitrogen atmosphere. The resulting mixture was stirred for 1.5 h at −50--40° C. under nitrogen atmosphere then quenched with saturated NaHCO₃(aq.) at 0° C. The resulting mixture was extracted with DCM and the combined organic layers were washed with water and dried over anhydrous Na₂SO₄. After filtration, the filtrate was concentrated under reduced pressure and the crude was purified by Prep-HPLC to afford the title compound (4.3 mg, 14.3%) as a white solid. MS (ES, m/z): [M−H]⁻=398.1.

Example 10

Synthesis of 3-fluoro-5-((3,3,4,4-tetrafluoro-2a-hydroxy-2,2a,3,4-tetrahydro-1H-cyclopenta[cd]inden-7-yl)oxy)benzonitrile

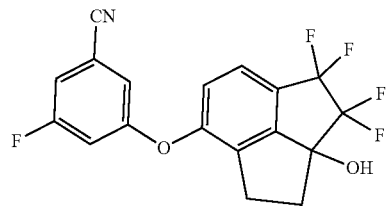 [SMILES: N#Cc1cc(F)cc(Oc2ccc3c4c2CCC4(O)C(F)(F)C3(F)F)c1]

Step 1: O-(7-(3-cyano-5-fluorophenoxy)-3,3,4,4-tetrafluoro-2a-hydroxy-2,2a,3,4-tetrahydro-1H-cyclopenta [cd]inden-1-yl) 1H-imidazole-1-carbothioate

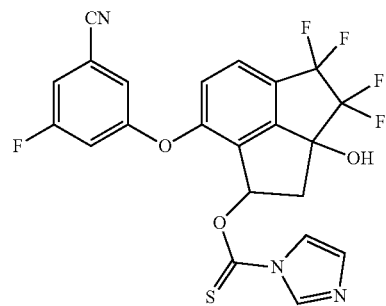 [SMILES: N#Cc1cc(F)cc(Oc2ccc3c4c2C(OC(=S)n2ccnc2)CC4(O)C(F)(F)C3(F)F)c1]

To a stirred solution of 3-fluoro-5-((3,3,4,4-tetrafluoro-1,2a-dihydroxy-2,2a,3,4-tetrahydro-1H-cyclopenta[cd]inden-7-yl)oxy)benzonitrile (100 mg, 0.26 mmol, 1.00 equiv.) and DMAP (6 mg, 0.05 mmol, 0.20 equiv.) in DCE (2.0 mL) was added di (1H-imidazol-1-yl) methanethione (56 mg, 0.31 mmol, 1.20 equiv.) at room temperature under nitrogen atmosphere. The resulting mixture was stirred for 3 h at room temperature. The reaction mixture was concentrated and the residue was purified by Prep-TLC (PE/EtOAc 2:1) to afford the title compound (80 mg, 62%). MS (ES, m/z): [M+H]⁺=494.1.

Step 2: 3-fluoro-5-((3,3,4,4-tetrafluoro-2a-hydroxy-2,2a,3,4-tetrahydro-1H-cyclopenta[cd]inden-7-yl)oxy)benzonitrile

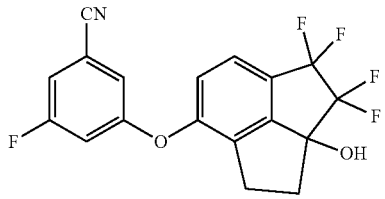 [SMILES: N#Cc1cc(F)cc(Oc2ccc3c4c2CCC4(O)C(F)(F)C3(F)F)c1]

To a stirred solution of O-(7-(3-cyano-5-fluorophenoxy)-3,3,4,4-tetrafluoro-2a-hydroxy-2,2a,3,4-tetrahydro-1H-cyclopenta[cd]inden-1-yl) 1H-imidazole-1-carbothioate (65 mg, 0.13 mmol, 1.00 equiv.) and Bu$_3$SnH (115 mg, 0.40 mmol, 3.00 equiv.) in toluene (2.0 mL) was added AIBN (65 mg, 0.40 mmol, 3.00 equiv.) at room temperature under nitrogen atmosphere. The resulting mixture was stirred for 16 h at 50° C., cooled and diluted with water, and extracted with EtOAc. The combined organic layers were washed with water and brine, dried over anhydrous Na$_2$SO$_4$ and concentrated. The residue was purified by Prep-TLC (PE/EtOAc=2/1) and Perp-HPLC to afford the title compound (12 mg, 25%) as a white solid. MS (ES, m/z): [M−H]$^-$=366.2.

Example 11

Synthesis of 3-((2a-amino-1,3,3,4,4-pentafluoro-2,2a,3,4-tetrahydro-1H-cyclopenta[cd]inden-7-yl)oxy)-5-fluorobenzonitrile

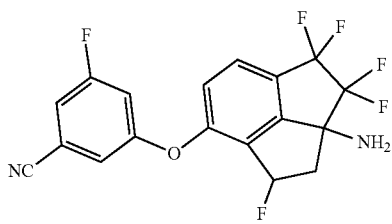 [SMILES: N#Cc1cc(F)cc(Oc2ccc3c4c2C(F)CC4(N)C(F)(F)C3(F)F)c1]

Step 1: N-(7-bromo-2,2,3,3,6-pentafluoro-2,3-dihydro-1H-inden-1-ylidene)-2-methylpropane-2-sulfinamide

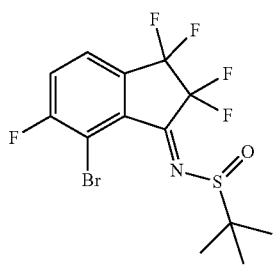 [SMILES: CC(C)(C)S(=O)/N=C1/c2c(ccc(F)c2Br)C(F)(F)C1(F)F]

To a stirred mixture of 7-bromo-2,2,3,3,6-pentafluoro-2,3-dihydro-1H-inden-1-one (1.00 g, 3.32 mmol, 1.00 equiv.) and 2-methylpropane-2-sulfinamide (0.81 g, 6.64 mmol, 2.00 equiv.) in THF (20.0 mL) was added Ti(OEt)$_4$ (3.03 g, 13.29 mmol, 4.00 equiv.) at room temperature. After stirring for 4 h at 75° C., the reaction mixture was cooled and concentrated under reduced pressure. The residue was purified by silica gel column chromatography, eluted with EtOAc/PE (0-60%), to afford the title compound (900 mg, 67.0%) as a brown oil. MS (ES, m/z): [M+1]$^+$=404.0.

Step 2: N-(1-allyl-7-bromo-2,2,3,3,6-pentafluoro-2,3-dihydro-1H-inden-1-yl)-2-methylpropane-2-sulfinamide

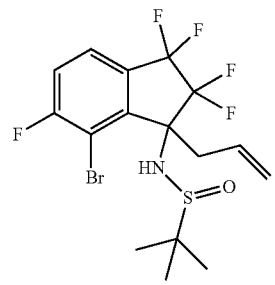 [SMILES: C=CCC1(NS(=O)C(C)(C)C)c2c(ccc(F)c2Br)C(F)(F)C1(F)F]

To a stirred solution of N-(7-bromo-2,2,3,3,6-pentafluoro-2,3-dihydro-1H-inden-1-ylidene)-2-methylpropane-2-sulfinamide (900 mg, 2.23 mmol, 1.00 equiv.) in THF (15.0 mL) was added allylmagnesium bromide (2.0 M, 1.34 mL, 2.70 mmol, 1.20 equiv.) at 0° C. After stirring for 1.5 h at 0° C., the reaction mixture was quenched with saturated NH$_4$Cl (aq.) at 0° C. then extracted with EtOAc. The combined organic layers were washed with brine and dried over anhydrous Na$_2$SO$_4$. After filtration, the filtrate was concentrated under reduced pressure. The residue was purified by silica gel column chromatography, eluted with EtOAc/PE (0-50%), to afford the title compound (750 mg, 75.5%) as a light yellow oil. MS (ES, m/z): [M+1]$^+$=446.1.

Step 3: 2-methyl-N-(3,3,4,4,7-pentafluoro-1-methylene-1,2,3,4-tetrahydro-2aH-cyclopenta[cd]-inden-2a-yl)propane-2-sulfinamide

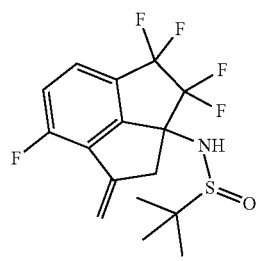 [SMILES: C=C1CC2(NS(=O)C(C)(C)C)c3c(ccc(F)c31)C(F)(F)C2(F)F]

To a stirred mixture of N-(1-allyl-7-bromo-2,2,3,3,6-pentafluoro-2,3-dihydro-1H-inden-1-yl)-2-methylpropane-2-sulfinamide (750 mg, 1.68 mmol, 1.00 equiv.) and Pd(dppf)Cl$_2$·CH$_2$Cl$_2$ (137 mg, 0.17 mmol, 0.10 equiv.) in DMF (15.0 mL) was added NaOAc (414 mg, 5.05 mmol, 3.00 equiv.) at room temperature under nitrogen atmosphere. After stirring for 1.5 h at 100° C., the reaction mixture was cooled to room temperature, quenched with water and extracted with EtOAc. The combined organic layers were washed with brine and dried over anhydrous Na$_2$SO$_4$. After filtration, the filtrate was concentrated under reduced pressure. The residue was purified by silica gel column chromatography, eluted with EtOAc/PE (10%-40%), to afford the title compound (450 mg, 73.3%) as a light yellow solid. MS (ES, m/z): [M+1]$^+$=366.1.

Step 4: 3,3,4,4,7-pentafluoro-1-methylene-1,2,3,4-tetrahydro-2aH-cyclopenta[cd]inden-2a-amine

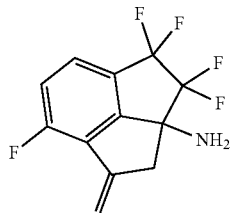 [SMILES: C=C1CC2(N)c3c(ccc(F)c31)C(F)(F)C2(F)F]

To a stirred solution of 2-methyl-N-(3,3,4,4,7-pentafluoro-1-methylene-1,2,3,4-tetrahydro-2aH-cyclopenta[cd]inden-2a-yl) propane-2-sulfinamide (150 mg, 0.41 mmol, 1.00 equiv.) in 1,4-dioxane (1.0 mL) was added a solution of HCl in 1,4-dioxane (4.0 M, 1.00 mL, 4.0 mmol, 9.74 equiv.) at room temperature. After stirring for 5 h at room temperature, the reaction mixture was quenched with NaHCO$_3$ (aq.) at room temperature and extracted with EtOAc. The combined organic layers were washed with brine and dried over anhydrous Na$_2$SO$_4$. After filtration, the filtrate was concentrated under reduced pressure. The residue was purified by silica gel column chromatography, eluted with EtOAc/PE (0-60%), to afford the title compound (85 mg, 79.3%) as a light yellow oil. MS (ES, m/z): [M+1]$^+$=262.1.

Step 5: 2a-amino-3,3,4,4,7-pentafluoro-2,2a,3,4-tetrahydro-1H-cyclopenta[cd]inden-1-one

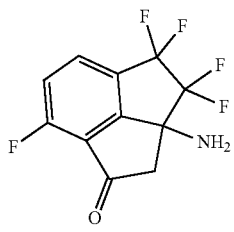 [SMILES: NC12CC(=O)c3c(F)ccc(c31)C(F)(F)C2(F)F]

To a stirred mixture of 3,3,4,4,7-pentafluoro-1-methylene-1,2,3,4-tetrahydro-2aH-cyclopenta[cd]inden-2a-amine (85 mg, 0.325 mmol, 1.00 equiv.) and NaIO$_4$ (278 mg, 1.30 mmol, 4.00 equiv.) in CH$_3$CN (0.50 mL) and DCM (0.50 mL) were added water (0.75 mL) and RuCl$_3$·H$_2$O (7.34 mg, 0.03 mmol, 0.10 equiv.) at room temperature. After stirring for 1 h at room temperature, the resulting mixture was diluted with DCM. The organic layer was washed with brine and dried over anhydrous Na$_2$SO$_4$. After filtration, the filtrate was concentrated under reduced pressure and the residue was purified by Prep-TLC (PE/EtOAc=3/1) to afford the title compound (45 mg, 52.5%) as a light yellow oil. MS (ES, m/z): [M−1]$^-$=261.9.

Step 6: 3-((2a-amino-3,3,4,4-tetrafluoro-1-oxo-2,2a,3,4-tetrahydro-1H-cyclopenta[cd]inden-7-yl)oxy)-5-fluorobenzonitrile

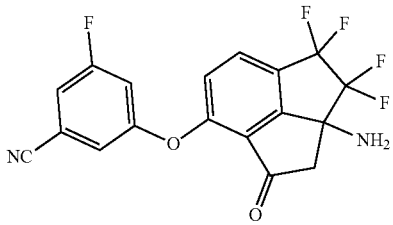 [SMILES: N#Cc1cc(F)cc(Oc2ccc3c4c2C(=O)CC4(N)C(F)(F)C3(F)F)c1]

To a stirred mixture of 2a-amino-3,3,4,4,7-pentafluoro-2,2a,3,4-tetrahydro-1H-cyclopenta[cd]inden-1-one (40 mg, 0.15 mmol, 1.00 equiv.) and 3-fluoro-5-hydroxybenzonitrile (21 mg, 0.15 mmol, 1.00 equiv.) in DMF (1.00 mL) was added Cs$_2$CO$_3$ (50 mg, 0.15 mmol, 1.00 equiv.) at room temperature. After stirring for 1.5 h at room temperature, the reaction was quenched with water and extracted with EtOAc. The combined organic layers were washed with brine and dried over anhydrous Na$_2$SO$_4$. After filtration, the filtrate was concentrated under reduced pressure. The residue was purified by Prep-TLC (PE/EtOAc-3/1) to afford the title compound (35 mg, 60.3%) as a white solid. MS (ES, m/z): [M+1]$^+$=381.1.

Step 7: 3-((2a-amino-3,3,4,4-tetrafluoro-1-hydroxy-2,2a,3,4-tetrahydro-1H-cyclopenta[cd]inden-7-yl)oxy)-5-fluorobenzonitrile

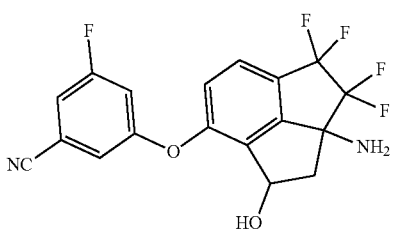 [SMILES: N#Cc1cc(F)cc(Oc2ccc3c4c2C(O)CC4(N)C(F)(F)C3(F)F)c1]

To a stirred solution of 3-((2a-amino-3,3,4,4-tetrafluoro-1-oxo-2,2a,3,4-tetrahydro-1H-cyclopenta[cd]inden-7-yl)oxy)-5-fluorobenzonitrile (35 mg, 0.09 mmol, 1.00 equiv.) in MeOH (0.50 mL) was added NaBH$_4$ (5 mg, 0.13 mmol, 1.4 equiv.) at room temperature. After stirring for 0.5 h at room temperature, the reaction mixture was quenched with saturated NH$_4$Cl (aq.) at 0° C. and extracted with EtOAc. The combined organic layers were washed with brine and dried over anhydrous Na$_2$SO$_4$. After filtration, the filtrate was concentrated under reduced pressure. The residue was purified by silica gel column chromatography, eluted with EtOAc/PE (0-60%), to afford the title compound (30 mg, 85.3%) as a light yellow oil. MS (ES, m/z): [M+1]$^+$=383.1.

Step 8: 3-((2a-amino-1,3,3,4,4-pentafluoro-2,2a,3,4-tetrahydro-1H-cyclopenta[cd]inden-7-yl)oxy)-5-fluorobenzonitrile

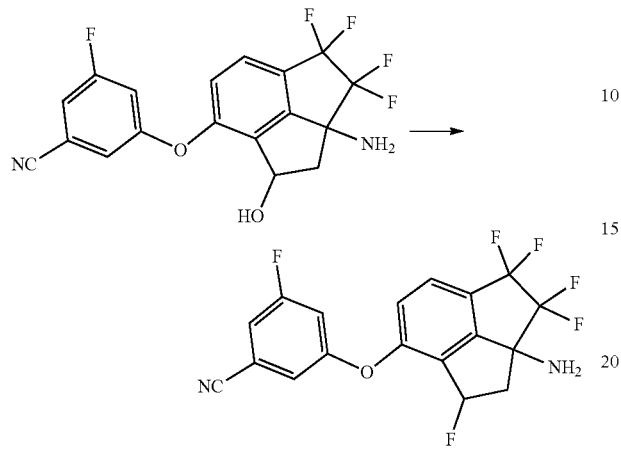

To a stirred solution of 3-((2a-amino-3,3,4,4-tetrafluoro-1-hydroxy-2,2a,3,4-tetrahydro-1H-cyclopenta[cd]inden-7-yl)oxy)-5-fluorobenzonitrile (25 mg, 0.07 mmol, 1.00 equiv.) in DCM (1.0 mL) was added DAST (16 mg, 0.10 mmol, 1.5 equiv.) at room temperature. After stirring for 2 h at room temperature, the reaction mixture was quenched with saturated NaHCO$_3$ (aq.) at 0° C. and extracted with DCM. The combined organic layers were washed with brine and dried over anhydrous Na$_2$SO$_4$. After filtration, the filtrate was concentrated and purified by Prep-HPLC to afford the title compound (6 mg, 24%) as a white solid. MS (ES, m/z): [M+1]$^+$=385.1.

Example 12

Synthesis of 3-fluoro-5-((1,1,2a,3,3,4,4-heptafluoro-2,2a,3,4-tetrahydro-1H-cyclopenta[cd]inden-7-yl)oxy)benzonitrile

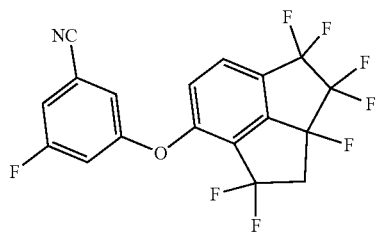 [SMILES: N#Cc1cc(F)cc(Oc2ccc3c4c2C(F)(F)CC4(F)C(F)(F)C3(F)F)c1]

To a stirred mixture of 3-fluoro-5-((3,3,4,4-tetrafluoro-2a-hydroxy-1-oxo-2,2a,3,4-tetrahydro-1H-cyclo-penta[cd]inden-7-yl)oxy)benzonitrile (30 mg, 0.08 mmol, 1.00 equiv.) in DCM (1.0 mL) were added 4-tert-butyl-2,6-dimethylphenylsulfur trifluoride (59 mg, 0.24 mmol, 3.00 equiv.) and pyridine hydrofluoride (0.05 mL, 65%-70%) at room temperature. The resulting mixture was stirred for 24 h at room temperature under nitrogen atmosphere then diluted with water and extracted with DCM. The combined organic layers were washed with water and dried over anhydrous Na$_2$SO$_4$. After filtration, the filtrate was concentrated and purified by Prep-HPLC to afford the title compound (9.9 mg, 31.1%) as a white solid. MS (ES, m/z): [M–H]$^-$=404.1.

Example 13

Synthesis of 3-((3,3-difluoro-2a-hydroxy-1-methylene-2,2a,3,4-tetrahydro-1H-cyclopenta[cd]inden-5-yl)oxy)-5-fluorobenzonitrile

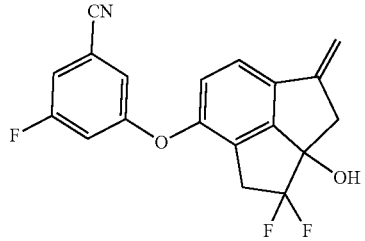 [SMILES: C=C1CC2(O)c3c1ccc(Oc1cc(F)cc(C#N)c1)c3CC2(F)F]

Step 1: 3-fluoro-5-((7-iodo-1-oxo-2,3-dihydro-1H-inden-4-yl)oxy)benzonitrile

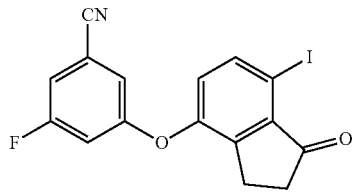 [SMILES: N#Cc1cc(F)cc(Oc2ccc(I)c3c2CCC3=O)c1]

Into a 2 L round-bottom flask were added 3-fluoro-5-((1-oxo-2,3-dihydro-1H-inden-4-yl)oxy)benzonitrile (28 g, 104.77 mmol, 1.00 equiv.), F-TEDA-BF$_4$ (33 g, 93.15 mmol, 0.89 equiv.) and CH$_3$CN (840 mL). To this stirred solution was added a solution of I$_2$ (24 g, 94.56 mmol, 0.90 equiv.) in CH$_3$CN (560 mL) dropwise at 60° C. The resulting mixture was stirred for 3 h at 60° C. The mixture was cooled to room temperature then concentrated under vacuum. To the residue was added ethyl acetate (250 mL) and the resulting mixture was stirred for 1 h at 80° C. The mixture was cooled to room temperature and the precipitated solids were collected by filtration and washed with Et$_2$O to afford the tittle compound (16.8 g, 40.8%) as an off-white solid. MS (ES, m/z): [M+H]$^+$=394.0.

Step 2: 3-((2,2-difluoro-7-iodo-1-oxo-2,3-dihydro-1H-inden-4-yl)oxy)-5-fluorobenzonitrile

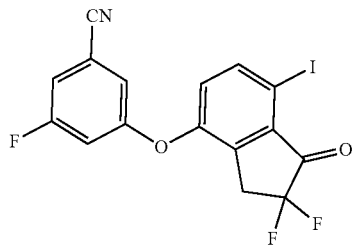 [SMILES: N#Cc1cc(F)cc(Oc2ccc(I)c3c2CC(F)(F)C3=O)c1]

To a stirred mixture of 3-fluoro-5-((7-iodo-1-oxo-2,3-dihydro-1H-inden-4-yl)oxy)-benzonitrile (3.600 g, 9.15 mmol, 1.00 equiv.) and butan-1-amine (6.7 g, 91.57 mmol, 10.00 equiv.) in toluene (90 mL) was added TFA (209 mg, 1.83 mmol, 0.20 equiv.) dropwise at room temperature. The resulting mixture was stirred for 16 h at 100° C. under nitrogen atmosphere then concentrated under vacuum. The residue was dissolved in CH$_3$CN (90 mL), followed by the addition of Na$_2$SO$_4$ (5.2 g, 36.62 mmol, 4.00 equiv.) and F-TEDA-BF4 (6.5 g, 18.31 mmol, 2.00 equiv.) at room temperature. The resulting mixture was stirred for 2 h at 80° C., diluted with water and extracted with EtOAc. The combined organic layers were washed with water, brine, and dried over anhydrous Na$_2$SO$_4$. After filtration, the filtrate was concentrated under reduced pressure. The residue was purified by silica gel column chromatography, eluted with PE/EtOAc (10:1), to afford (1.60 g, 40.7%) of the title compound as a yellow solid.

Step 3: 3-((1-allyl-2,2-difluoro-1-hydroxy-7-iodo-2,3-dihydro-1H-inden-4-yl)oxy)-5-fluorobenzonitrile

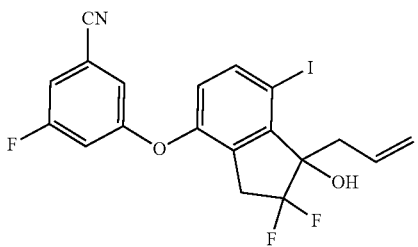 [SMILES: C=CCC1(O)c2c(I)ccc(Oc3cc(F)cc(C#N)c3)c2CC1(F)F]

To a stirred mixture of 3-((2,2-difluoro-7-iodo-1-oxo-2,3-dihydro-1H-inden-4-yl)oxy)-5-fluorobenzonitrile (449 mg, 1.05 mmol, 1.00 equiv.) and allylbromide (253.15 mg, 2.093 mmol, 2.00 equiv.) in THF (10 mL) were added pyridine (165.52 mg, 2.09 mmol, 2.00 equiv.) and (1S,2R)-2-amino-1,2-diphenylethanol (446.30 mg, 2.09 mmol, 2.00 equiv.) at room temperature. Indium powder (240.26 mg, 2.09 mmol, 2.00 equiv.) was then added into the solution and the resulting mixture was stirred for 8 h at room temperature under nitrogen atmosphere. The resulting mixture was filtered and the filter cake was washed with EtOAc. The filtrate was concentrated and purified by silica gel column chromatography, eluted with PE/EtOAc (9:1), to afford the tittle compound (430 mg, 87.2%) as a yellow oil. MS (ES, m/z): [M−H]$^-$=470.0.

Step 4: 3-((3,3-difluoro-2a-hydroxy-1-methylene-2,2a,3,4-tetrahydro-1H-cyclopenta[cd]inden-5-yl)oxy)-5-fluorobenzonitrile

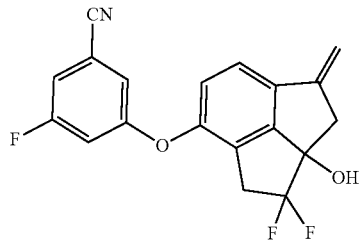 [SMILES: C=C1CC2(O)c3c1ccc(Oc1cc(F)cc(C#N)c1)c3CC2(F)F]

To a stirred solution of 3-((1-allyl-2,2-difluoro-1-hydroxy-7-iodo-2,3-dihydro-1H-inden-4-yl)oxy)-5-fluorobenzonitrile (430 mg, 0.91 mmol, 1.00 equiv.) and NaOAc (225 mg, 2.74 mmol, 3.00 equiv.) in DMF (10 mL) was added Pd(dppf)Cl$_2$·CH$_2$Cl$_2$ (75 mg, 0.09 mmol, 0.10 equiv.) at room temperature under nitrogen atmosphere. The resulting mixture was stirred for 3 h at 100° C. under nitrogen atmosphere then filtered. The filter cake was washed with EtOAc and the filtrate was washed with H$_2$O, dried over anhydrous Na$_2$SO$_4$ and concentrated. The residue was purified by silica gel column chromatography, eluted with PE/EtOAc (5:1), to afford the title compound (223 mg, 71.2%) as a yellow oil.

Example 14

Synthesis of 3-((3,3-difluoro-2a-hydroxy-1-oxo-2,2a,3,4-tetrahydro-1H-cyclopenta[cd]inden-5-yl)oxy)-5-fluorobenzonitrile

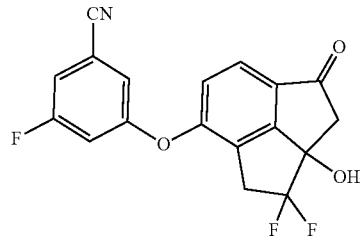 [SMILES: N#Cc1cc(F)cc(Oc2ccc3c4c2CC(F)(F)C4(O)CC3=O)c1]

Into a 25 mL 2-necked round-bottom flask were added 3-((3,3-difluoro-2a-hydroxy-1-methylene-2,2a,3,4-tetrahydro-1H-cyclopenta[cd]inden-5-yl)oxy)-5-fluorobenzonitrile (210 mg, 0.61 mmol, 1.00 equiv.), DCM (2.0 mL), MeCN (2.0 mL) and H$_2$O (3.0 mL) at room temperature. RuCl$_3$·H$_2$O (7 mg, 0.03 mmol, 0.05 equiv.) was then added into the solution. To the above mixture was added NaIO$_4$ (523 mg, 2.45 mmol, 4.00 equiv.) in portions over 2 min at room temperature and the resulting mixture was stirred for 3 h at room temperature. The resulting mixture was extracted with DCM and the combined organic layers were washed with Na$_2$S$_2$O$_3$ (aq.), H$_2$O and brine, and dried over anhydrous Na$_2$SO$_4$. After filtration, the filtrate was concentrated under reduced pressure. The residue was purified by silica gel column chromatography, eluted with PE/EtOAc (5:1), to afford the tittle compound (107 mg, 50.7%) as a yellow oil. MS (ES, m/z): [2M−H]$^-$=689.1.

Example 15

Synthesis of 3-((3,3-difluoro-1,2a-dihydroxy-2,2a,3,4-tetrahydro-1H-cyclopenta[cd]inden-5-yl)oxy)-5-fluorobenzonitrile

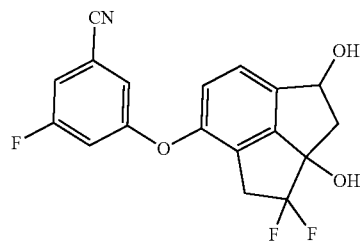 [SMILES: N#Cc1cc(F)cc(Oc2ccc3c4c2CC(F)(F)C4(O)CC3O)c1]

Into an 8 mL sealed tube were added 3-((3,3-difluoro-2a-hydroxy-1-oxo-2,2a,3,4-tetrahydro-1H-cyclopenta[cd]inden-5-yl)oxy)-5-fluorobenzonitrile (100 mg, 0.29 mmol, 1.00 equiv.) and MeOH (2.00 mL) at room temperature. To the above mixture was added NaBH₄ (22 mg, 0.58 mmol, 2.0 equiv.) in portions at 0° C. and the resulting mixture was stirred for 1 h at room temperature. The reaction was quenched with water at 0° C. and neutralized to pH=7 with aqueous HCl (1.0 M). The resulting mixture was extracted with DCM and the combined organic layers were dried over anhydrous Na₂SO₄. After filtration, the filtrate was concentrated and purified by Prep-TLC (PE/EtOAc=5/1) to afford the tittle compound (78 mg, 77.6%) as a white solid.

Example 16

Synthesis of 3-fluoro-5-((1,3,3-trifluoro-2a-hydroxy-2,2a,3,4-tetrahydro-1H-cyclopenta[cd]inden-5-yl)oxy)benzonitrile

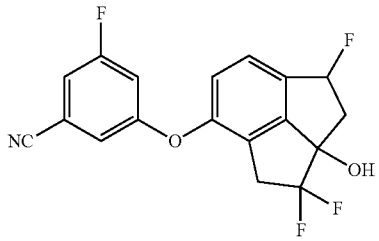 [SMILES: N#Cc1cc(F)cc(Oc2ccc3c4c2CC(F)(F)C4(O)CC3F)c1]

To a stirred solution of 3-((3,3-difluoro-1,2a-dihydroxy-2,2a,3,4-tetrahydro-1H-cyclopenta[cd]inden-5-yl)oxy)-5-fluorobenzonitrile (20 mg, 0.06 mmol, 1.00 equiv.) in THF (0.50 mL) was added a solution of DAST (9.35 mg, 0.06 mmol, 1.00 equiv.) in DCM (0.2 mL) dropwise at −50° C. under nitrogen atmosphere. The resulting mixture was stirred for 1 h at −50° C. under nitrogen atmosphere then quenched with water at −40° C. The mixture was neutralized to pH=7 with saturated NaHCO₃(aq.) then extracted with EtOAc. The combined organic layers were washed with brine and dried over anhydrous Na₂SO₄. After filtration, the filtrate was concentrated and purified by Prep-HPLC to afford the title compound (5.7 mg, 28.3%) as a white solid. MS (ES, m/z): [2M−H]⁻=697.2.

Example 17

Synthesis of 3-fluoro-5-((1,1,2,2,3,3,4-heptafluoro-2a-hydroxy-2,2a,3,4-tetrahydro-1H-cyclopenta[cd]inden-5-yl)oxy)benzonitrile

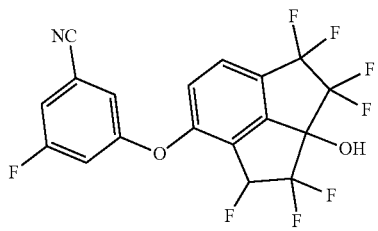 [SMILES: N#Cc1cc(F)cc(Oc2ccc3c4c2C(F)C(F)(F)C4(O)C(F)(F)C3(F)F)c1]

Step 1: ethyl 2,2-difluoro-2-(2,2,3,3,6-pentafluoro-1-hydroxy-2,3-dihydro-1H-inden-1-yl)acetate

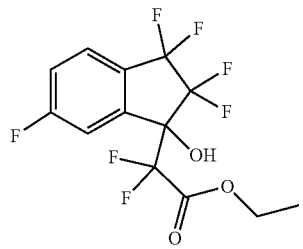 [SMILES: CCOC(=O)C(F)(F)C1(O)c2cc(F)ccc2C(F)(F)C1(F)F]

A mixture of 2,2,3,3,6-pentafluoro-2,3-dihydro-1H-inden-1-one (10.0 g, 45.02 mmol, 1.00 equiv.), In (7.7 g, 67.06 mmol, 1.5 equiv.) and ethyl 2-bromo-2,2-difluoroacetate (13.7 g, 67.5 mmol, 1.50 equiv.) in THF (150 mL) was stirred for 16 h at 60° C. under N₂ atmosphere. The reaction was quenched with aqueous HCl (2.0 M, 50 mL) at room temperature and the resulting mixture was extracted with ethyl acetate. The combined organic layers were dried over anhydrous Na₂SO₄. After filtration, the filtrate was concentrated under reduced pressure. The residue was purified by silica gel column chromatography, eluted with PE/EA (5/1), to afford the title compound (8.0 g, 51.3%) as a light-yellow oil. MS (ES, m/z): [M−1]⁻=345.0

Step 2: 1,1,2,2,3,3,5-heptafluoro-2a-hydroxy-1,2,2a,3-tetrahydro-4H-cyclopenta[cd]inden-4-one

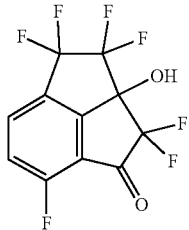 [SMILES: O=C1c2c(F)ccc3c2C(O)(C1(F)F)C(F)(F)C3(F)F]

To a stirred solution of ethyl 2,2-difluoro-2-(2,2,3,3,6-pentafluoro-1-hydroxy-2,3-dihydro-1H-inden-1-yl) acetate (500 mg, 1.44 mmol, 1.00 equiv.) in THF (10 mL) was added LDA (2.2 mL, 4.40 mmol, 2.0 M, 3.06 equiv.) dropwise at −78° C. under N₂ atmosphere. The resulting mixture was stirred for 1 h at −78° C. and then quenched with saturated aqueous NH₄Cl (10 mL) at −78° C. The resulting mixture was extracted with ethyl acetate and the combined organic layers were dried over anhydrous Na₂SO₄. After filtration, the filtrate was concentrated and purified by silica gel column chromatography, eluted with PE/EA (3/1), to afford crude product. The crude product was purified by Prep-HPLC to afford the title product (34 mg, 7.8%) as a light-yellow oil. MS (ES, m/z): [M−1]⁻=298.9

Step 3: 3-fluoro-5-((1,1,2,2,3,3-hexafluoro-2a-hydroxy-4-oxo-2,2a,3,4-tetrahydro-1H-cyclopenta[cd]inden-5-yl)oxy)benzonitrile

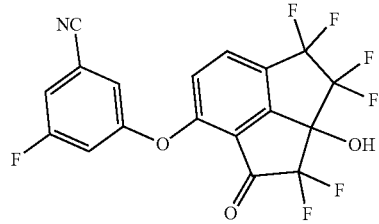 [SMILES: N#Cc1cc(F)cc(Oc2ccc3c4c2C(=O)C(F)(F)C4(O)C(F)(F)C3(F)F)c1]

A mixture of 1,1,2,2,3,3,5-heptafluoro-2a-hydroxy-1,2,2a,3-tetrahydro-4H-cyclopenta-[cd]inden-4-one (100 mg, 0.33 mmol, 1.00 equiv.), Cs$_2$CO$_3$ (217 mg, 0.67 mmol, 2.00 equiv.) and 3-fluoro-5-hydroxybenzonitrile (50 mg, 0.36 mmol, 1.10 equiv.) in DMF (2 mL) was stirred for 1 h at −10° C. under N$_2$ atmosphere. The crude reaction mixture was used for next step directly without further purification. MS (ES, m/z): [M−1]$^−$=416.0.

Step 4: 3-fluoro-5-((1,1,2,2,3,3-hexafluoro-2a,4-dihydroxy-2,2a,3,4-tetrahydro-1H-cyclopenta[cd]inden-5-yl)oxy)benzonitrile

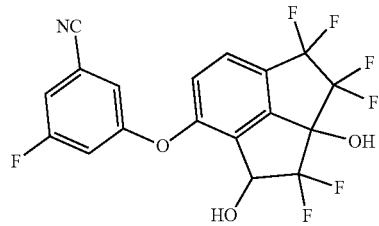 [SMILES: N#Cc1cc(F)cc(Oc2ccc3c4c2C(O)C(F)(F)C4(O)C(F)(F)C3(F)F)c1]

To a stirred solution of crude 3-fluoro-5-((1,1,2,2,3,3-hexafluoro-2a-hydroxy-4-oxo-2,2a,3,4-tetrahydro-1H-cyclopenta[cd]inden-5-yl)oxy)benzonitrile (0.33 mmol, 1.00 equiv.) in MeOH (2 mL) was added NaBH$_4$ (25 mg, 0.66 mmol, 2.00 equiv.) in portions at −10° C. under N$_2$ atmosphere. The resulting mixture was stirred for 1 h at −10° C. and then quenched with saturated aqueous NH$_4$Cl solution. The resulting mixture was extracted with ethyl acetate and the combined organic layers were washed with brine, and dried over anhydrous Na$_2$SO$_4$. After filtration, the filtrate was concentrated under reduced pressure. The residue was purified by silica gel column chromatography, eluted with PE/EA (3/1), to afford the title compound (90 mg, 63.6%) for two steps as a light-yellow oil. MS (ES, m/z): [M−1]$^−$=418.0.

Step 5: 3-fluoro-5-((1,1,2,2,3,3,4-heptafluoro-2a-hydroxy-2,2a,3,4-tetrahydro-1H-cyclopenta[cd]inden-5-yl)oxy)benzonitrile

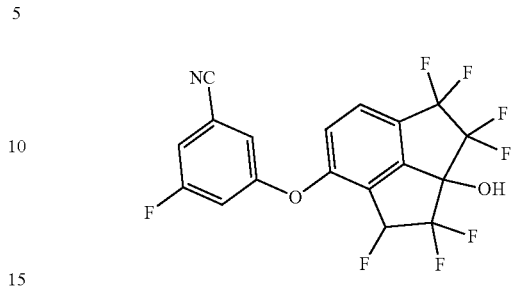

To a stirred solution of 3-fluoro-5-((1,1,2,2,3,3-hexafluoro-2a,4-dihydroxy-2,2a,3,4-tetrahydro-1H-cyclopenta[cd]inden-5-yl)oxy)benzonitrile (50 mg, 0.12 mmol, 1.00 equiv.) in DCM (1.0 mL) was added DAST (38 mg, 0.24 mmol, 2.00 equiv.) dropwise at −20° C. under N$_2$ atmosphere. The resulting mixture was stirred for 2 h at room temperature, quenched with saturated aqueous NaHCO$_3$ solution. The resulting mixture was extracted with DCM and the combined organic layers were dried over anhydrous Na$_2$SO$_4$. After filtration, the filtrate was concentrated under reduced pressure and the crude product was purified by Prep-HPLC to afford the title compound (14 mg, 27.5%) as a light yellow solid. MS (ES, m/z): [M−1]$^−$=420.0.

Example 18

Synthesis of 3-fluoro-5-(((1S,2aR)-1,3,3,4,4-pentafluoro-2a-hydroxy-2,2a,3,4-tetrahydro-1H-cyclopenta[cd]inden-7-yl-1,2,2-d3)oxy)benzonitrile

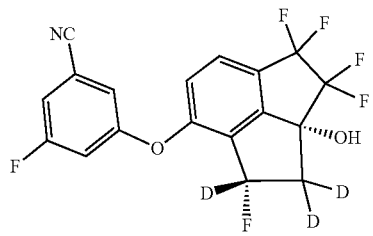 [SMILES: [2H]C1([2H])[C@@]2(O)c3c(ccc(Oc4cc(F)cc(C#N)c4)c3[C@@]1([2H])F)C(F)(F)C2(F)F]

Step 1: (R)-1-allyl-2,2,3,3,6-pentafluoro-2,3-dihydro-1H-inden-1-ol

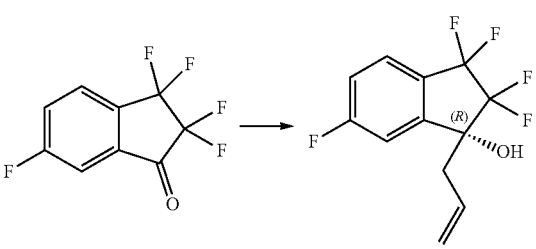

To a stirred solution of t-BuONa (21.6 mg, 0.225 mmol, 0.10 equiv.) in toluene (3.0 mL) were added a solution of (S)-2-((3-(tert-butyl)-2-hydroxybenzyl) amino)-N,N,3- trimethylbutanamide (275.8 mg, 0.90 mmol, 0.40 equiv.) in toluene (0.5 mL), then a solution of MeOH (90.2 mg, 2.8 mmol, 1.25 equiv.) in toluene (0.5 mL), followed by a solution of 2,2,3,3,6-pentafluoro-2,3-dihydro-1H-inden-1-one (0.50 g, 2.25 mmol, 1.00 equiv.) in toluene (0.5 mL). After stirring for 15 min at room temperature, a solution of 4,4,5,5-tetramethyl-2-(prop-2-en-1-yl)-1,3,2-dioxaborolane (416.1 mg, 2.48 mmol, 1.10 equiv.) in toluene (0.5 mL) was added slowly. The resulting mixture was stirred for 6.5 h at 60° C., cooled and diluted with ethyl acetate. After separation, the organic layer was washed with water and brine, dried over Na$_2$SO$_4$. After filtration, the filtrate was concentrated and purified by silica gel column chromatography, eluted with DCM/PE (0-40%), to afford the title compound (0.52 g, 87.4%) as a light yellow oil. MS (ES, m/z): [M−1]$^-$=263.0.

Step 2: (1R)-7-bromo-2,2,3,3,6-pentafluoro-1-(prop-2-en-1-yl)inden-1-ol

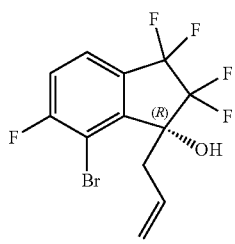

To a stirred solution of (R)-1-allyl-2,2,3,3,6-pentafluoro-2,3-dihydro-1H-inden-1-ol (5.0 g, 18.93 mmol, 1.00 equiv.) in tetrahydrofuran (60 mL) was added 2.0 M LDA (28.4 mL, 56.8 mmol, 3.0 equiv.) dropwise at −40° C. under nitrogen atmosphere. After stirring for 1 h at −40° C., a solution of carbon tetrabromide (7.53 g, 22.71 mmol, 1.20 equiv.) in THF was added dropwise at −40° C. The resulting mixture was stirred for additional 10 min at −40° C., then quenched with 1.0 M HCl (aq.) (100 mL) at −40° C. The resulting mixture was extracted with MTBE. The organic layer was washed with water and brine, dried over anhydrous Na$_2$SO$_4$. After filtration, the filtrate was concentrated and purified by silica gel column chromatography, eluted with EtOAc/PE (0-30%), to afford the crude product as light yellow oil. This crude product was further purified by reversed-phase C18 silica gel column (mobile phase, ACN in water, 50% to 95% gradient in 12 min) to afford the title compound (3.5 g, 53.9%) as a light yellow oil. MS (ES, m/z): [M−1]$^-$=340.9.

Step 3: (R)-3,3,4,4,7-pentafluoro-1-methylene-1,2,3,4-tetrahydro-2aH-cyclopenta[cd]inden-2a-ol

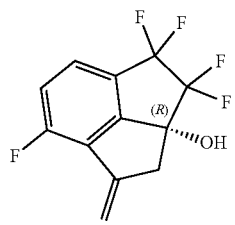

To a stirred mixture of (R)-1-allyl-7-bromo-2,2,3,3,6-pentafluoro-2,3-dihydro-1H-inden-1-ol (3.50 g, 10.20 mmol, 1.00 equiv.) in DMF (5.0 mL) were added AcONa (2.51 g, 30.60 mmol, 3.00 equiv.) and Pd(dppf)Cl$_2$·CH$_2$Cl$_2$ (0.83 g, 1.02 mmol, 0.10 equiv.) at room temperature under nitrogen atmosphere. The resulting mixture was stirred for 3 h at 100° C. under nitrogen atmosphere, cooled and diluted with water, then extracted with ethyl acetate. The organic layer was washed with water and brine, dried over anhydrous Na$_2$SO$_4$. After filtration, the filtrate was concentrated and purified by silica gel column chromatography, eluted with EtOAc/PE (0-40%), to afford the title compound (2.0 g, 74.8%) as a light yellow solid. MS (ES, m/z): [M−1]$^-$=260.9.

Step 4: (R)-3,3,4,4,7-pentafluoro-2a-hydroxy-2,2a,3,4-tetrahydro-1H-cyclopenta[cd]inden-1-one

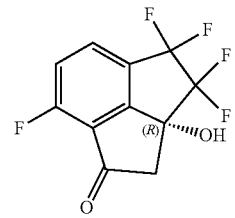

To a stirred mixture of (R)-3,3,4,4,7-pentafluoro-1-methylene-1,2,3,4-tetrahydro-2aH-cyclopenta[cd]inden-2a-ol (2.00 g, 7.63 mmol, 1.00 equiv.) in a mixed solvents (DCM/MeCN/H$_2$O=1/1/1.5, 70.0 mL) was added RuCl$_3$·H$_2$O (86.0 mg, 0.38 mmol, 0.05 equiv.) at room temperature. To the resulting mixture was added NaIO$_4$ (6.53 g, 30.53 mmol, 4.0 equiv.) in portions at room temperature. After stirring for 1 h at room temperature, the reaction mixture was diluted with water, then extracted with DCM. The organic layer was washed with saturated Na$_2$S$_2$O$_3$ (aq.), water and brine, dried over anhydrous Na$_2$SO$_4$. After filtration, the filtrate was concentrated to afford crude title compound (1.85 g, 91.8%) as a light yellow solid, which was used for next step without further purification. MS (ES, m/z): [M−1]$^-$=262.9.

Step 5: (R)-3-fluoro-5-((3,3,4,4-tetrafluoro-2a-hydroxy-1-oxo-2,2a,3,4-tetrahydro-1H-cyclopenta[cd]inden-7-yl)oxy)benzonitrile

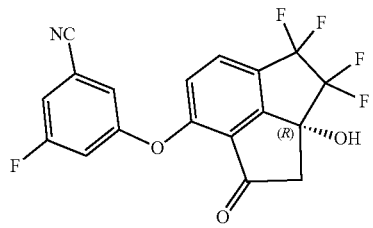

To a stirred solution of (R)-3,3,4,4,7-pentafluoro-2a-hydroxy-2,2a,3,4-tetrahydro-1H-cyclopenta[cd]inden-1-one (1.85 g, 7.00 mmol, 1.00 equiv.) and 3-fluoro-5-hydroxybenzonitrile (0.86 g, 6.30 mmol, 0.90 equiv.) in DMF (20.0 mL) was added Cs$_2$CO$_3$ (2.28 g, 7.00 mmol, 1.00 equiv.) at room temperature. After stirring for 16 h at room temperature, the reaction mixture was quenched with water at 0° C., then extracted with EtOAc. The organic layer was washed with water and brine, dried over anhydrous Na₂SO₄. After filtration, the filtrate was concentrated and purified by silica gel column chromatography, eluted with EtOAc/PE (0-40%), to afford the title compound (1.95 g, 73.0%) as a white solid. MS (ES, m/z): [M−1]−=380.1.

Step 6: (R)-3-fluoro-5-((3,3,4,4-tetrafluoro-2a-hydroxy-1-oxo-2,2a,3,4-tetrahydro-1H-cyclopenta[cd]inden-7-yl-2,2-d2)oxy)benzonitrile

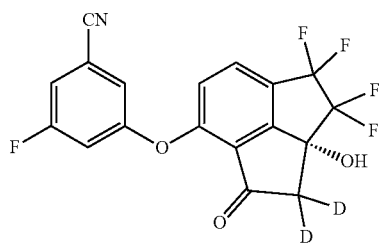 [SMILES: [2H]C1([2H])C(=O)c2c(Oc3cc(F)cc(C#N)c3)ccc3c2[C@@]1(O)C(F)(F)C3(F)F]

To a stirred mixture of (R)-3-fluoro-5-((3,3,4,4-tetrafluoro-2a-hydroxy-1-oxo-2,2a,3,4-tetrahydro-1H-cyclopenta[cd]inden-7-yl)oxy)benzonitrile (3.0 g, 7.87 mmol, 1.00 equiv.) in THF (60 mL) was added a solution of NaOD (645 mg, 15.737 mmol, 2.00 equiv.) in D2O (24 mL) dropwise at room temperature. The resulting mixture was stirred for 4 h at room temperature then diluted with D2O and extracted with MTBE. The combined organic layers were dried over anhydrous Na₂SO₄. After filtration, the filtrate was concentrated under reduced pressure and the residue was purified by silica gel column chromatography, eluted with PE/EA (3:1), to afford the title compound (2.3 g, 76.3%) as a white solid. MS (ES, m/z): [M−H]−=382.1.

Step 7: 3-fluoro-5-(((1R,2aR)-3,3,4,4-tetrafluoro-1,2a-dihydroxy-2,2a,3,4-tetrahydro-1H-cyclopenta[cd]inden-7-yl-1,2,2-d3)oxy)benzonitrile

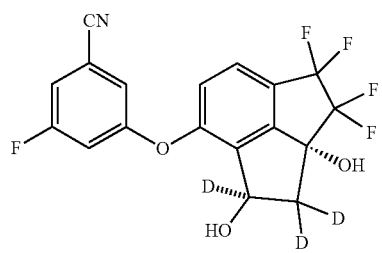 [SMILES: [2H]C1([2H])[C@@]2(O)c3c(ccc(Oc4cc(F)cc(C#N)c4)c3[C@]1([2H])O)C(F)(F)C2(F)F]

To a stirred mixture of (R)-3-fluoro-5-((3,3,4,4-tetrafluoro-2a-hydroxy-1-oxo-2,2a,3,4-tetrahydro-1H-cyclopenta[cd]inden-7-yl-2,2-d2) oxy)benzonitrile (1.5 g, 3.883 mmol, 1.00 equiv.) in CD₃OD (15 mL) was added NaBD₄ (329 mg, 7.827 mmol, 2.00 equiv.) at 5° C. The resulting mixture was stirred for 2 h at room temperature then quenched with D2O at room temperature. The resulting mixture was extracted with MTBE and the combined organic layers were dried over anhydrous Na₂SO₄. After filtration, the filtrate was concentrated under reduced pressure and the residue was purified by silica gel column chromatography, eluted with PE/EA (3:1), to afford the title compound (1.5 g, 99.2%) as a light yellow solid. MS (ES, m/z): [M−H]−=385.1.

Step 8: 3-fluoro-5-(((1S,2aR)-1,3,3,4,4-pentafluoro-2a-hydroxy-2,2a,3,4-tetrahydro-1H-cyclopenta[cd]inden-7-yl-1,2,2-d3)oxy)benzonitrile

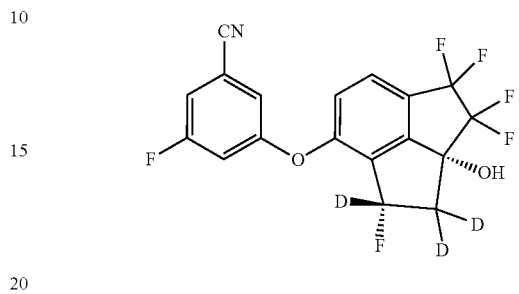

To a stirred mixture of 3-fluoro-5-(((1R,2aR)-3,3,4,4-tetrafluoro-1,2a-dihydroxy-2,2a,3,4-tetrahydro-1H-cyclopenta[cd]inden-7-yl-1,2,2-d3)oxy)benzonitrile (1.5 g, 3.88 mmol, 1.00 equiv.) in THF (21 mL) were added DBU (1.18 g, 7.77 mmol, 2.00 equiv.) and pyridine-2-sulfonyl fluoride (814 mg, 5.05 mmol, 1.30 equiv.) in THF (2 mL) dropwise at room temperature under nitrogen atmosphere. The resulting mixture was stirred for 16 h at room temperature under nitrogen atmosphere then concentrated under reduced pressure. The residue was purified by silica gel column chromatography with PE/EA (4:1). The resulting product was further purified by chiral Prep-HPLC to afford the optical pure title compound (740 mg, 49.1%) as a white solid. MS (ES, m/z): [M−H]−=387.1.

Example 19

Synthesis of 3-fluoro-5-(((1S,2aR)-1,3,3,4,4-pentafluoro-2a-hydroxy-2,2a,3,4-tetrahydro-1H-cyclopenta[cd]inden-7-yl-1-d) oxy)benzonitrile-2,4,6-d₃

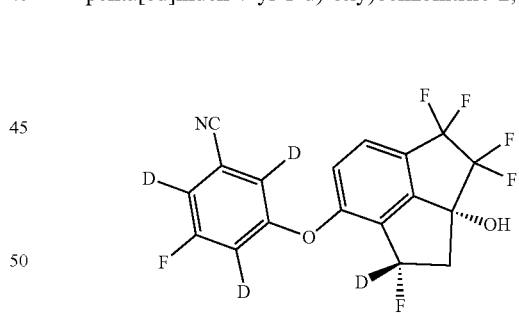

Step 1: 3-bromo-5-fluorophen-2,4,6-d3-ol

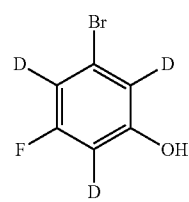

Into a 40 mL sealed tube were added 3-bromo-5-fluorophenol (5.00 g, 26.18 mmol, 1.00 equiv.) and 60% D2SO4 (13.09 g, 78.53 mmol, 3.00 equiv.) in D2O at room temperature. The resulting mixture was stirred for 18 h at 75° C. then poured slowly onto ice. The resulting mixture was extracted with EtOAc and the combined organic layers were washed with water, brine and dried over anhydrous $Na_2SO_4$. After filtration, the filtrate was concentrated under reduced pressure to give the product. The product was added in 60% $D_2SO_4$ in D2O, and the above procedure was repeated for additional 4 times to give the title compound (4.20 g, 82.7% yield) as yellow oil. MS (ES, m/z): [M–H]⁻=191.9.

Step 2: 3-fluoro-5-hydroxybenzonitrile-2,4,6-d3

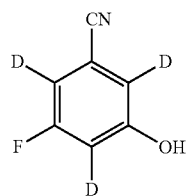 [SMILES: [2H]c1c(O)c([2H])c(C#N)c([2H])c1F]

To a stirred solution of 3-bromo-5-fluorophen-2,4,6-d3-ol (100 mg, 0.515 mmol, 1.00 equiv.) and Zn (CN) 2 (121 mg, 1.03 mmol, 2.0 equiv.) in DMF (2.0 mL) was added Pd(PPh3) 4 (60 mg, 0.05 mmol, 0.10 equiv.) at room temperature under nitrogen atmosphere. The resulting mixture was stirred for 3 h at 100° C. under nitrogen atmosphere and then quenched with water at room temperature. The resulting mixture was extracted with EtOAc and the combined organic layers were washed with water, brine, and dried over anhydrous $Na_2SO_4$. After filtration, the filtrate was concentrated under reduced pressure. The residue was purified by silica gel column chromatography, eluted with PE/EtOAc (1:1), to afford the title compound (37 mg, 51.2%) as a white solid. MS (ES, m/z): [M–H]⁻=139.0.

Step 3: (R)-3-fluoro-5-((3,3,4,4-tetrafluoro-2a-hydroxy-1-oxo-2,2a,3,4-tetrahydro-1H-cyclopenta[cd]inden-7-yl)oxy)benzonitrile-2,4,6-d3

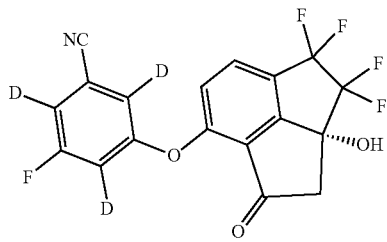 [SMILES: [2H]c1c(F)c([2H])c(Oc2ccc3c4c2C(=O)C[C@]4(O)C(F)(F)C3(F)F)c([2H])c1C#N]

To a stirred mixture of (R)-3,3,4,4,7-pentafluoro-2a-hydroxy-2,2a,3,4-tetrahydro-1H-cyclopenta[cd]inden-1-one (179 mg, 0.68 mmol, 1.00 equiv.) and 3-fluoro-5-hydroxybenzonitrile-2,4,6-d3 (95 mg, 0.68 mmol, 1.00 equiv.) in DMF (3.5 mL) was added $Cs_2CO_3$ (221 mg, 0.68 mmol, 1.00 equiv.) at room temperature. After stirring for 16 h at room temperature, the reaction mixture was quenched with water at 0° C. The resulting mixture was extracted with EtOAc and the combined organic layers were washed with $H_2O$, brine and dried over anhydrous $Na_2SO_4$. After filtration, the filtrate was concentrated under reduced pressure. The residue was purified by silica gel column chromatography, eluted with EtOAc/PE (0-40%), to afford the title compound (170 mg, 65.3%) as a white solid. MS (ES, m/z): [M–H]⁻=383.0.

Step 4: 3-fluoro-5-(((1R,2aR)-3,3,4,4-tetrafluoro-1,2a-dihydroxy-2,2a,3,4-tetrahydro-1H-cyclopenta[cd]inden-7-yl-1-d) oxy)benzonitrile-2,4,6-d₃

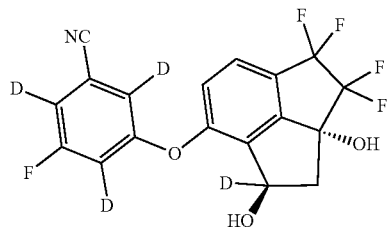 [SMILES: [2H]c1c(F)c([2H])c(Oc2ccc3c4c2[C@]([2H])(O)C[C@]4(O)C(F)(F)C3(F)F)c([2H])c1C#N]

To a stirred mixture of (R)-3-fluoro-5-((3,3,4,4-tetrafluoro-2a-hydroxy-1-oxo-2,2a,3,4-tetrahydro-1H-cyclopenta[cd]inden-7-yl)oxy)benzonitrile-2,4,6-d3 (170 mg, 0.442 mmol, 1.00 equiv.) in CD3OD (3.5 mL) was added NaBD4 (37 mg, 0.885 mmol, 2.00 equiv.) in portions at room temperature. The resulting mixture was stirred for 3 h at room temperature, diluted with D2O (3.0 mL) and extracted with EtOAc. The combined organic layers were dried over anhydrous $Na_2SO_4$, and filtered. The filtrate was concentrated and and the residue was purified by silica gel column chromatography, eluted with EtOAc/PE (0-40%), to afford the tittle compound (120 mg, 70.0%) as a white solid. MS (ES, m/z): [2M–H]⁻=773.1.

Step 5: 3-fluoro-5-(((1S,2aR)-1,3,3,4,4-pentafluoro-2a-hydroxy-2,2a,3,4-tetrahydro-1H-cyclopenta[cd]inden-7-yl-1-d) oxy)benzonitrile-2,4,6-d₃

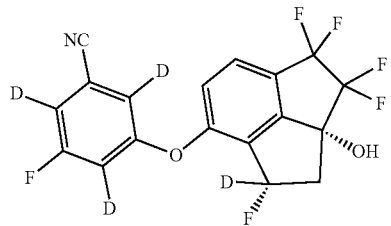 [SMILES: [2H]c1c(F)c([2H])c(Oc2ccc3c4c2[C@@]([2H])(F)C[C@]4(O)C(F)(F)C3(F)F)c([2H])c1C#N]

To a stirred mixture of 3-fluoro-5-(((1R,2aR)-3,3,4,4-tetrafluoro-1,2a-dihydroxy-2,2a,3,4-tetrahydro-1H-cyclopenta[cd]inden-7-yl-1-d) oxy)benzonitrile-2,4,6-d₃ (125 mg, 0.32 mmol, 1.00 equiv.) in THF (1.6 mL) were added DBU (98 mg, 0.65 mmol, 2.00 equiv.) and pyridine-2-sulfonyl fluoride (68 mg, 0.42 mmol, 1.30 equiv.) in THF (0.4 mL) dropwise at room temperature under nitrogen atmosphere. The resulting mixture was stirred for 16 h at room temperature under nitrogen atmosphere. The reaction solution was purified by silica gel column chromatography, eluted with PE/EtOAc (4:1), followed by purification with prep-HPLC to afford the tittle compound (10 mg, 8.0%) as a white solid. MS (ES, m/z): [M–H]⁻=388.1.

Example 20

Synthesis of (R)-3-fluoro-5-((3,3,4,4-tetrafluoro-2a-hydroxy-1-methylene-2,2a,3,4-tetrahydro-1H-cyclopenta[cd]inden-7-yl)oxy)benzonitrile [23a] and (S)-3-fluoro-5-((3,3,4,4-tetrafluoro-2a-hydroxy-1-methylene-2,2a,3,4-tetrahydro-1H-cyclopenta[cd]inden-7-yl)oxy)benzonitrile [23b]

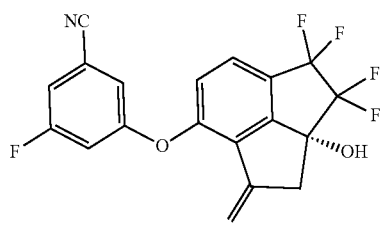

23a

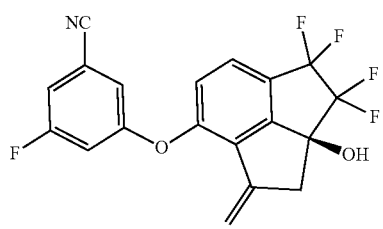

23b

To a stirred mixture of (R)-3,3,4,4,7-pentafluoro-1-methylene-1,2,3,4-tetrahydro-2aH-cyclopenta[cd]inden-2a-ol (400 mg, 1.53 mmol, 1.0 equiv, ~80% ee) and 3-fluoro-5-hydroxybenzonitrile (209 mg, 1.53 mmol, 1.0 equiv) in DMF (10 mL) was added Cs$_2$CO$_3$ (497 mg, 1.53 mmol, 1.0 equiv) at room temperature and the resulting mixture was stirred for 24 h at 100° C. After cooling the reaction mixture to room temperature, it was filtered. The filtrate was purified by Prep-HPLC to afford 131 mg of product as a mixture of enantiomers. The enantiomers were separated by Chiral pre-HPLC [Column: CHIRALPAK OD-3, 50*4.6 mm, 3 um OD30CC-QE001, flow rate: 1.0 mL/min; oven temperature: 25° C.; Mobile Phase A: n-hexanes; Mobile Phase B: ethanol; conc. of Phase B: 10%) to afford 23a (65 mg, 11.2%) MS (ES, m/z): [M−H]$^−$=378.0. tR: 1.34 min and 23b (6 mg, 1.0%); MS (ES, m/z): [M−H]$^−$=378.0. tR: 1.77 min.

Example 21

Synthesis of 3-fluoro-5-(((2aS, 3S)-1,2,3,3,4,4-hexafluoro-2a-hydroxy-2,2a,3,4-tetrahydro-1H-cyclopenta[cd]inden-7-yl)oxy)benzonitrile [24a] and 3-fluoro-5-(((2aS, 3R)-1,2,3,3,4,4-hexafluoro-2a-hydroxy-2,2a,3,4-tetrahydro-1H-cyclopenta[cd]inden-7-yl)oxy)benzonitrile [24b]

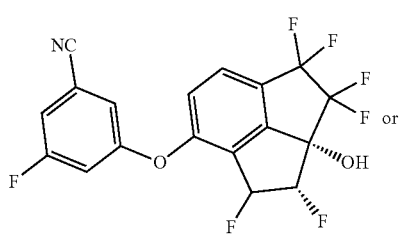

24a or

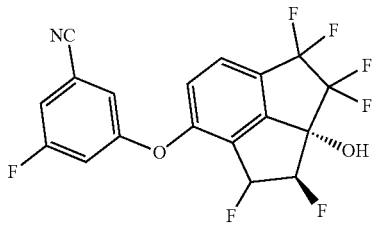

24b

Step 1: (R)-3-((4-(butylimino)-1,1,2,2-tetrafluoro-2a-hydroxy-2,2a,3,4-tetrahydro-1H-cyclopenta[cd]inden-5-yl)oxy)-5-fluorobenzonitrile

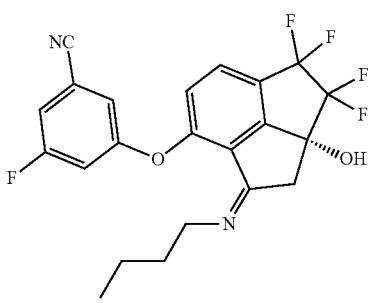 [SMILES: CCCC/N=C1/C[C@@]2(O)c3c(ccc(Oc4cc(F)cc(C#N)c4)c31)C(F)(F)C2(F)F]

A solution of (R)-3-fluoro-5-((1,1,2,2-tetrafluoro-2a-hydroxy-4-oxo-2,2a,3,4-tetrahydro-1H-cyclopenta[cd]inden-5-yl)oxy)benzonitrile (700 mg, 1.84 mmol, 1.0 equiv., ~80% ee), TFA (42 mg, 0.37 mmol, 0.2 equiv.) and butylamine (1343 mg, 18.36 mmol, 10.0 equiv.) in toluene (15 mL) was stirred for 16 h at 100° C. under N$_2$ atmosphere. The resulting mixture was concentrated under vacuum to afford the title compound (1.0 g, crude) as a light brown oil, which was used for next step directly. MS (ES, m/z): [M+1]$^+$=437.2.

Step 2: 3-fluoro-5-(((2aS,3S)-1,1,2,2,3-pentafluoro-2a-hydroxy-4-oxo-2,2a,3,4-tetrahydro-1H-cyclopenta[cd]inden-5-yl)oxy)benzonitrile and 3-fluoro-5-(((2aS,3R)-1,1,2,2,3-pentafluoro-2a-hydroxy-4-oxo-2,2a,3,4-tetrahydro-1H-cyclopenta[cd]inden-5-yl)oxy)benzonitrile

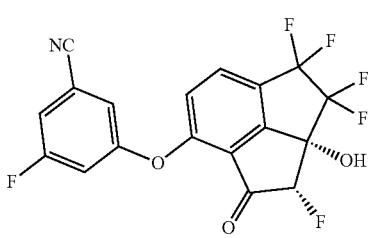

-continued

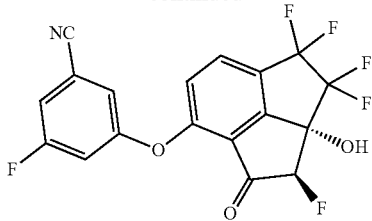

A mixture of (R)-3-((4-(butylimino)-1,1,2,2-tetrafluoro-2a-hydroxy-2,2a,3,4-tetrahydro-1H-cyclopenta[cd]inden-5-yl)oxy)-5-fluorobenzonitrile (1.0 g crude, 1.84 mmol, 1.0 equiv.), sodium sulfate (651 mg, 4.58 mmol, 2.5 equiv.) and Selectfluor (1.05 g, 2.96 mmol, 1.6 equiv.) in MeCN (15 mL) was stirred for 4 h at 60° C. under $N_2$ atmosphere. The crude product was purified by Prep-HPLC to afford 150 mg of one isomer and 300 mg of the other isomer. MS (ES, m/z): $[M-1]^-=397.9$.

Step 3: 3-fluoro-5-(((2aS, 3S)-1,1,2,2,3-pentafluoro-2a,4-dihydroxy-2,2a,3,4-tetrahydro-1H-cyclopenta [cd]inden-5-yl)oxy)benzonitrile and 3-fluoro-5-(((2aS,3R)-1,1,2,2,3-pentafluoro-2a,4-dihydroxy-2,2a,3,4-tetrahydro-1H-cyclopenta[cd]inden-5-yl)oxy)benzonitrile

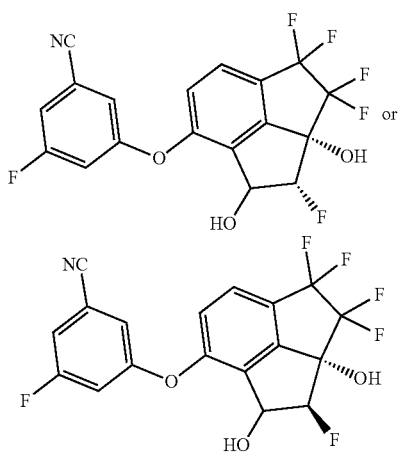

3-Fluoro-5-(((2aS,3S)-1,1,2,2,3-pentafluoro-2a-hydroxy-4-oxo-2,2a,3,4-tetrahydro-1H-cyclopenta[cd]inden-5-yl)oxy)benzonitrile or 3-fluoro-5-(((2aS,3R)-1,1,2,2,3-pentafluoro-2a-hydroxy-4-oxo-2,2a,3,4-tetrahydro-1H-cyclopenta[cd]inden-5-yl)oxy)benzonitrile were converted to 3-fluoro-5-(((2aS, 3S)-1,1,2,2,3-pentafluoro-2a,4-dihydroxy-2,2a,3,4-tetrahydro-1H-cyclopenta[cd]inden-5-yl)oxy)benzonitrile or 3-fluoro-5-(((2aS, 3R)-1,1,2,2,3-pentafluoro-2a,4-dihydroxy-2,2a,3,4-tetrahydro-1H-cyclopenta[cd]inden-5-yl)oxy)benzonitrile, respectively as follows.

To a stirred solution of 3-fluoro-5-(((2aS,3S)-1,1,2,2,3-pentafluoro-2a-hydroxy-4-oxo-2,2a,3,4-tetrahydro-1H-cyclopenta[cd]inden-5-yl)oxy)benzonitrile or 3-fluoro-5-(((2aS,3S)-1,1,2,2,3-pentafluoro-2a-hydroxy-4-oxo-2,2a,3,4-tetrahydro-1H-cyclopenta[cd]inden-5-yl)oxy)benzonitrile (1.0 equiv.) in MeOH was added NaBH₄ (2.0 equiv.) in portions at 0° C. under $N_2$ atmosphere. The resulting mixture was stirred for 1 h at room temperature the quenched with saturated aqueous NH₄Cl solution. The resulting mixture was extracted with ethyl acetate. The combined organic layers were washed with brine, dried over anhydrous Na₂SO₄. After filtration, the filtrate was concentrated under reduced pressure to afford 3-fluoro-5-(((2aS, 3S)-1,1,2,2,3-pentafluoro-2a,4-dihydroxy-2,2a,3,4-tetrahydro-1H-cyclopenta[cd]inden-5-yl)oxy)benzonitrile or 3-fluoro-5-(((2aS, 3R)-1,1,2,2,3-pentafluoro-2a,4-dihydroxy-2,2a,3,4-tetrahydro-1H-cyclopenta[cd]inden-5-yl)oxy)benzonitrile respectively, as a light yellow oil. MS (ES, m/z): $[2M-1]^-=801.2$.

Step 4: 3-fluoro-5-(((2aS, 3S)-1,2,3,3,4,4-hexafluoro-2a-hydroxy-2,2a,3,4-tetrahydro-1H-cyclopenta[cd]inden-7-yl)oxy)benzonitrile or 3-fluoro-5-(((2aS, 3R)-1,2,3,3,4,4-hexafluoro-2a-hydroxy-2,2a,3,4-tetrahydro-1H-cyclopenta[cd]inden-7-yl)oxy)benzonitrile

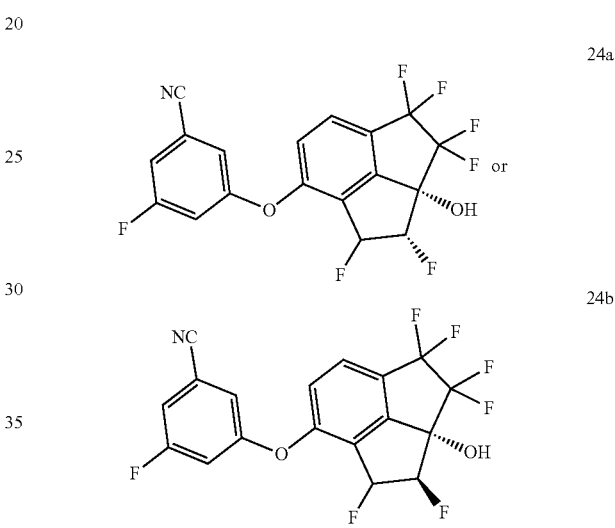

3-Fluoro-5-(((2aS, 3S)-1,1,2,2,3-pentafluoro-2a,4-dihydroxy-2,2a,3,4-tetrahydro-1H-cyclopenta[cd]inden-5-yl)oxy)benzonitrile or 3-fluoro-5-(((2aS, 3R)-1,1,2,2,3-pentafluoro-2a,4-dihydroxy-2,2a,3,4-tetrahydro-1H-cyclopenta[cd]inden-5-yl)oxy)benzonitrile were converted to 3-fluoro-5-(((2aS, 3S)-1,2,3,3,4,4-hexafluoro-2a-hydroxy-2,2a,3,4-tetrahydro-1H-cyclopenta[cd]inden-7-yl)oxy)benzonitrile or 3-fluoro-5-(((2aS, 3R)-1,2,3,3,4,4-hexafluoro-2a-hydroxy-2,2a,3,4-tetrahydro-1H-cyclopenta[cd]inden-7-yl)oxy)benzonitrile as follows.

To a stirred solution of 3-fluoro-5-(((2aS,3S)-1,1,2,2,3-pentafluoro-2a,4-dihydroxy-2,2a,3,4-tetrahydro-1H-cyclopenta[cd]inden-5-yl)oxy)benzonitrile or 3-fluoro-5-(((2aS, 3R)-1,1,2,2,3-pentafluoro-2a,4-dihydroxy-2,2a,3,4-tetrahydro-1H-cyclopenta[cd]inden-5-yl)oxy)benzonitrile (1.0 equiv.) in DCM was added DAST (1.5 equiv.) dropwise at −40° C. under $N_2$ atmosphere. The resulting mixture was stirred for 2 h at −40° C., quenched with saturated aqueous NH₄Cl solution. The resulting mixture was extracted with DCM. The combined organic layers were dried over anhydrous Na₂SO₄. After filtration, the filtrate was concentrated under reduced pressure. The crude product was purified by Prep-HPLC to afford 3-fluoro-5-(((2aS, 3S)-1,2,3,3,4,4-hexafluoro-2a-hydroxy-2,2a,3,4-tetrahydro-1H-cyclopenta[cd]inden-7-yl)oxy)benzonitrile or 3-fluoro-5-(((2aS, 3R)-1,2,3,3,4,4-hexafluoro-2a-hydroxy-2,2a,3,4-tetrahydro-1H- cyclopenta[cd]inden-7-yl)oxy)benzonitrile respectively as a light yellow solid. MS (ES, m/z): [M−1]⁻=402.0.

Since the stereochemistry at *C of compound 24a and 24b has not been determined, compound 24a is either be compound 24a1 or 24a2.

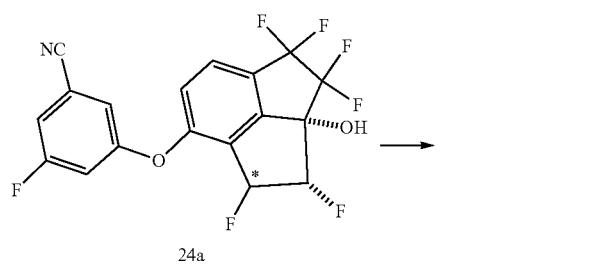

24a

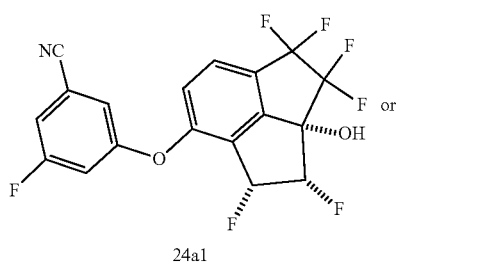

24a1

24a2

Similarly, compound 24b is compound 24b1 or 24b2.

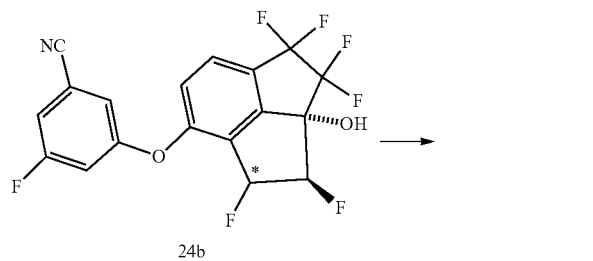

24b

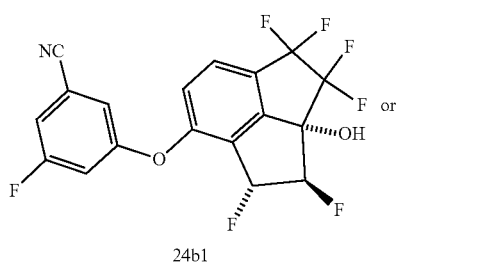

24b1

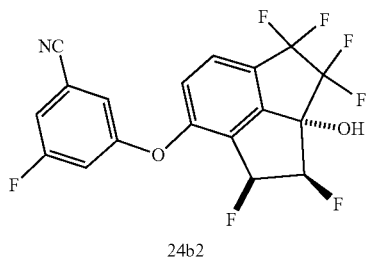

24b2

BIOLOGICAL EXAMPLES

Example 1

VEGF ELISA Assay

The ability of the disclosed compounds to inhibit HIF-2α was measured by determining VEGF expression in 786-0 cells. About 7500 786-O cells were seeded into each well of a 96-well, white, clear bottom plate (07-200-566, Fisher Scientific) with 200 ul growth medium. Four hours later, compounds were dispensed into wells by Tecan D300e digital dispenser with starting concentration of 10 uM and ½ log of dilution down to 1 nM as final concentration. Each concentration of treatment was performed in duplicate. About 20 hours later, medium was removed and fresh medium was added, followed by compounds treatment as described above. 24 hours later, cell culture medium was collected to determine VEGF concentration using an ELISA kit (R&D systems, cat #DVE00) following the manufacturer's instruction.

The $EC_{50}$ is calculated by GraphPad Prism using the dose-response-inhibition (four parameter) equation. The plate with cells was then subjected to CellTiter-Glo luminescence cell viability assay (Promega) to determine the effect of these compounds on cell numbers after the above treatment.

| Compound No. as in Cpd. Table 1 | $EC_{50}$ (μM) |
|---|---|
| 1 | 0.013 |
| 4 | 0.010 |
| 5 | 0.006 |
| 7 | 2.10 |
| 8 | 0.32 |
| 9 | 0.17 |
| 10 | 0.41 |
| 11 | >5 |
| 12 | 0.10 |
| 13 | 0.33 |
| 14 | 0.63 |
| 15 | >5 |
| 19 | 4.1 |
| 21 | 0.006 |
| 23a | 0.007 |

Formulation Examples

The following are representative pharmaceutical formulations containing a compound of the present disclosure.

Tablet Formulation

The following ingredients are mixed intimately and pressed into single scored tablets.

| Ingredient | Quantity per tablet (mg) |
| --- | --- |
| compound of this disclosure | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule (mg) |
| --- | --- |
| compound of this disclosure | 200 |
| lactose spray dried | 148 |
| magnesium stearate | 2 |

Injectable Formulation

Compound of the disclosure (e.g., a compound of formula I) in 2% HPMC, 1% Tween 80 in DI water, q.s. to at least 20 mg/mL.

Inhalation Composition

To prepare a pharmaceutical composition for inhalation delivery, 20 mg of a compound disclosed herein is mixed with 50 mg of anhydrous citric acid and 100 mL of 0.9% sodium chloride solution. The mixture is incorporated into an inhalation delivery unit, such as a nebulizer, which is suitable for inhalation administration.

Topical Gel Composition

To prepare a pharmaceutical topical gel composition, 100 mg of a compound disclosed herein is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

Ophthalmic Solution Composition

To prepare a pharmaceutical ophthalmic solution composition, 100 mg of a compound disclosed herein is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

Nasal Spray Solution

To prepare a pharmaceutical nasal spray solution, 10 g of a compound disclosed herein is mixed with 30 mL of a 0.05M phosphate buffer solution (pH 4.4). The solution is placed in a nasal administrator designed to deliver 100 ul of spray for each application.

What is claimed:

1. A method of inhibiting or relieving cancer selected from a renal cancer, glioblastoma, neuroblastoma, paraganglioma, pheochromocytoma, pancreatic neuroendocrine tumors, colorectal cancer, somatostatinomas, hemangioblastomas, gastrointestinal stromal tumors, pituitary tumors, leiomyomas, leiomyosarcomas, polycythaemia, retinal cancers, von Hippel-Lindau disease, astrocytoma, lung cancer, melanoma, breast cancer, cervical cancer, head and neck cancer, ovarian cancer, prostate cancer, uterine leiomyomatosis, multiple myeloma, retinoblastoma, pancreatic endocrine tumors, squamous cell carcinoma, acute myeloid leukemia, myelodysplastic syndrome, and esophageal squamous cell carcinoma in a patient in need thereof which method comprises administering to the patient a therapeutically effective amount of a compound selected from the group consisting of:

3-fluoro-5-((1,3,3,4,4-pentafluoro-2a-hydroxy-2,2a,3,4-tetrahydro-1H-cyclopenta[cd]-inden-7-yl)oxy)benzonitrile, according to the following structure:

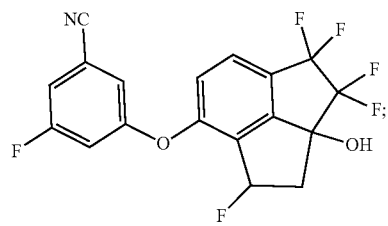 [SMILES: N#Cc1cc(F)cc(Oc2ccc3c4c2C(F)CC4(O)C(F)(F)C3(F)F)c1]

3-fluoro-5-((1,3,3,4,4-pentafluoro-2a-hydroxy-1-methyl-2,2a,3,4-tetrahydro-1H-cyclopenta[cd]inden-7-yl)oxy)benzonitrile, according to the following structure:

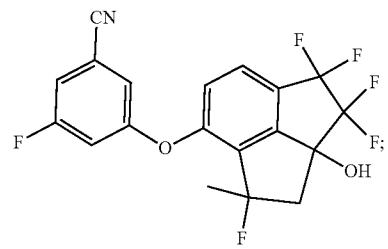 [SMILES: CC1(F)CC2(O)c3c(ccc(Oc4cc(F)cc(C#N)c4)c31)C(F)(F)C2(F)F]

3-fluoro-5-(((1S,2aR)-1,3,3,4,4-pentafluoro-2a-hydroxy-2,2a,3,4-tetrahydro-1H-cyclopenta[cd]inden-7-yl-1,2,2-d3)oxy)benzonitrile, according to the following structure:

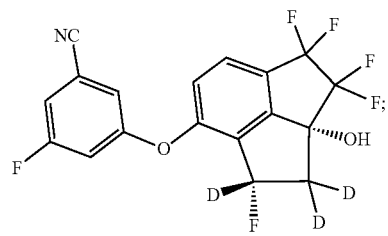 [SMILES: [2H]C1([2H])[C@@]2(O)c3c(ccc(Oc4cc(F)cc(C#N)c4)c3[C@@]1([2H])F)C(F)(F)C2(F)F]

and 3-fluoro-5-(((1S,2aR)-1,3,3,4,4-pentafluoro-2a-hydroxy-2,2a,3,4-tetrahydro-1H-cyclopenta[cd]inden-7-yl-1-d) oxy)benzonitrile-2,4,6-d3, according to the following structure:

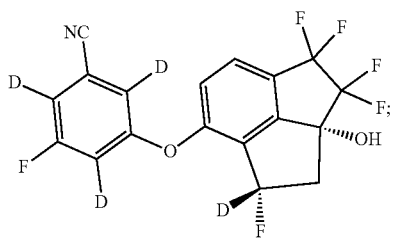 [SMILES: [2H]c1c(F)c([2H])c(Oc2ccc3c4c2[C@@]([2H])(F)C[C@]4(O)C(F)(F)C3(F)F)c([2H])c1C#N]

or a pharmaceutically acceptable salt thereof.

2. The method of claim 1, wherein the compound is 3-fluoro-5-((1,3,3,4,4-pentafluoro-2a-hydroxy-2,2a,3,4-tetrahydro-1H-cyclopenta[cd]inden-7-yl)oxy)benzonitrile, according to the following structure:

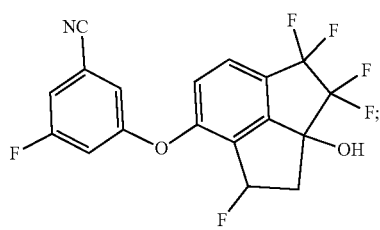 [SMILES: N#Cc1cc(F)cc(Oc2ccc3c4c2C(F)CC4(O)C(F)(F)C3(F)F)c1]

or a pharmaceutically acceptable salt thereof.

3. The method of claim 2, wherein the compound is 3-fluoro-5-(((1S,2aR)-1,3,3,4,4-pentafluoro-2a-hydroxy-2,2a,3,4-tetrahydro-1H-cyclopenta[cd]inden-7-yl)oxy)-benzonitrile, according to the following structure:

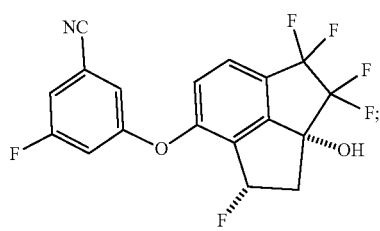 [SMILES: N#Cc1cc(F)cc(Oc2ccc3c4c2[C@@H](F)C[C@]4(O)C(F)(F)C3(F)F)c1]

or a pharmaceutically acceptable salt thereof.

4. The method of claim 2, wherein the compound is 3-fluoro-5-(((1R,2aR)-1,3,3,4,4-pentafluoro-2a-hydroxy-2,2a,3,4-tetrahydro-1H-cyclopenta[cd]-inden-7-yl)oxy)-benzonitrile, according to the following structure:

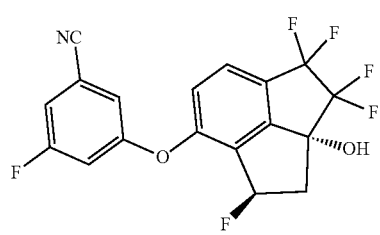

or a pharmaceutically acceptable salt thereof.

5. The method of claim 2, wherein the compound is a pharmaceutically acceptable salt of 3-fluoro-5-((1,3,3,4,4-pentafluoro-2a-hydroxy-2,2a,3,4-tetrahydro-1H-cyclopenta[cd]inden-7-yl)oxy)benzonitrile, according to the following structure:

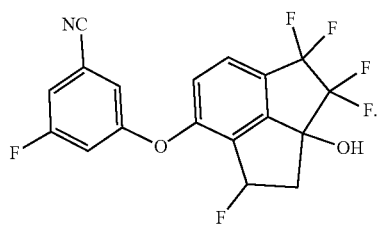 [SMILES: N#Cc1cc(F)cc(Oc2ccc3c4c2C(F)CC4(O)C(F)(F)C3(F)F)c1]

6. The method of claim 3, wherein the compound is a pharmaceutically acceptable salt of 3-fluoro-5-(((1S,2aR)-1,3,3,4,4-pentafluoro-2a-hydroxy-2,2a,3,4-tetrahydro-1H-cyclopenta[cd]-inden-7-yl)oxy)benzonitrile, according to the following structure:

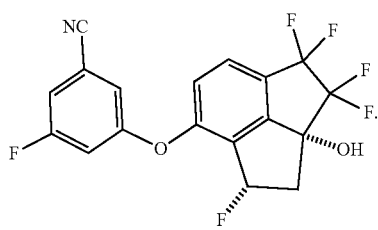

7. The method of claim 4, wherein the compound is a pharmaceutically acceptable salt of 3-fluoro-5-(((1R,2aR)-1,3,3,4,4-pentafluoro-2a-hydroxy-2,2a,3,4-tetrahydro-1H-cyclopenta[cd]-inden-7-yl)oxy)benzonitrile, according to the following structure:

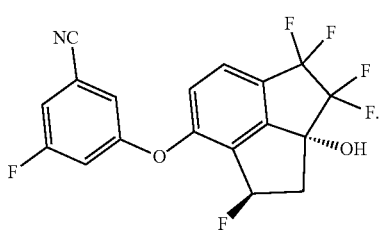 [SMILES: N#Cc1cc(F)cc(Oc2ccc3c4c2[C@H](F)C[C@]4(O)C(F)(F)C3(F)F)c1]

8. The method of claim 2, wherein the compound is 3-fluoro-5-((1,3,3,4,4-pentafluoro-2a-hydroxy-2,2a,3,4-tetrahydro-1H-cyclopenta[cd]inden-7-yl)oxy)benzonitrile, according to the following structure:

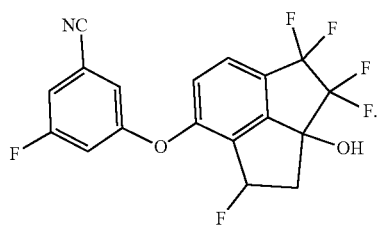 [SMILES: N#Cc1cc(F)cc(Oc2ccc3c4c2C(F)CC4(O)C(F)(F)C3(F)F)c1]

9. The method of claim 3, wherein the compound is 3-fluoro-5-(((1S,2aR)-1,3,3,4,4-pentafluoro-2a-hydroxy-2,2a,3,4-tetrahydro-1H-cyclopenta[cd]-inden-7-yl)oxy)benzonitrile, according to the following structure:

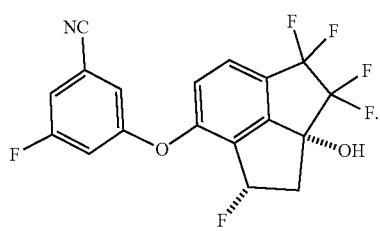

10. The method of claim 4, wherein the compound is 3-fluoro-5-(((1R,2aR)-1,3,3,4,4-pentafluoro-2a-hydroxy-2,2a,3,4-tetrahydro-1H-cyclopenta[cd]-inden-7-yl)oxy)benzonitrile, according to the following structure:

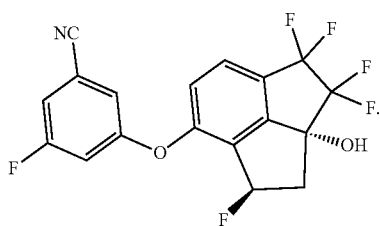 [SMILES: N#Cc1cc(F)cc(Oc2ccc3c4c2[C@H](F)C[C@]4(O)C(F)(F)C3(F)F)c1]

11. The method of claim 1, wherein the compound is administered in combination with at least one other anticancer agent.

12. The method of claim 2, wherein the compound is administered in combination with at least one other anticancer agent.

13. The method of claim 9, wherein the compound is administered in combination with at least one other anticancer agent.

14. The method of claim 2, wherein the cancer is renal cancer.

15. The method of claim 9, wherein the cancer is renal cancer.

16. The method of claim 13, wherein the cancer is renal cancer.

17. The method of claim 14, wherein the cancer is clear cell renal cell carcinoma.

18. The method of claim 15, wherein the cancer is clear cell renal cell carcinoma.

19. The method of claim 16, wherein the at least one other anticancer agent is cabozantinib or palbociclib.

* * * * *